US012742202B2

(12) United States Patent
Georgiou et al.

(10) Patent No.: US 12,742,202 B2
(45) Date of Patent: Sep. 22, 2026

(54) POLYMORPHISM (SNP) USING LAMP AND BLOCKING PRIMERS

(71) Applicant: IMPERIAL COLLEGE OF SCIENCE, TECHNOLOGY AND MEDICINE, London (GB)

(72) Inventors: Pantelis Georgiou, London (GB); Kenny Malpartida Cardenas, London (GB); Ling-Shan Yu, London (GB); Jake Baum, London (GB); Nicholas Miscourides, London (GB); Jesus Rodriguez Manzano, London (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 895 days.

(21) Appl. No.: 16/973,415

(22) PCT Filed: Jun. 7, 2019

(86) PCT No.: PCT/EP2019/065046
§ 371 (c)(1),
(2) Date: Dec. 8, 2020

(87) PCT Pub. No.: WO2019/234251
PCT Pub. Date: Dec. 12, 2019

(65) Prior Publication Data

US 2021/0238667 A1 Aug. 5, 2021

(30) Foreign Application Priority Data

Jun. 8, 2018 (GB) ..................................... 1809449

(51) Int. Cl.
*C12Q 1/6858* (2018.01)
*C12Q 1/6876* (2018.01)

(52) U.S. Cl.
CPC ......... *C12Q 1/6858* (2013.01); *C12Q 1/6876* (2013.01)

(58) Field of Classification Search
None
See application file for complete search history.

(56) References Cited

U.S. PATENT DOCUMENTS

| | | | | |
|---|---|---|---|---|
| 4,683,202 | A * | 7/1987 | Mullis .................... | C12Q 1/686 435/317.1 |
| 7,680,060 | B2 | 3/2010 | Jennings | |
| 7,680,868 | B2 | 3/2010 | Kurnik et al. | |
| 2006/0127934 | A1 | 6/2006 | Trama et al. | |
| 2007/0073489 | A1 | 3/2007 | Kurnik | |
| 2014/0113357 | A1 | 4/2014 | Russak | |

FOREIGN PATENT DOCUMENTS

| | | | |
|---|---|---|---|
| CN | 105624290 | A | 6/2016 |
| EP | 2272978 | A1 | 1/2011 |
| WO | WO-0015849 | A1 | 3/2000 |
| WO | WO-2008107014 | A1 | 9/2008 |
| WO | WO-2008137715 | A1 | 11/2008 |
| WO | WO-2010040374 | A1 | 4/2010 |
| WO | WO-2010099461 | A1 | 9/2010 |
| WO | WO-2013008042 | A1 | 1/2013 |
| WO | WO-2018027238 | A1 | 2/2018 |
| WO | WO-2018070659 | A1 | 4/2018 |

OTHER PUBLICATIONS

Van Pelt-Verkuil et al., Competitor Primers, in Principles and Technical Aspects of PCR Amplification, Springer Science + Business Media B.V., 2008, 72. (Year: 2008).*

Kubota, Real-Time Duplex Applications of Loop-Mediated Amplification (LAMP) by Assimilating Probes, Int J Mol Sci, 16(3): 4786-4799, 2015. (Year: 2015).*

Abu-Mostafa Y.S., et al., “Learning from Data”, 2012, 215 pages.

Bensimon A., et al., “Alignment and Sensitive Detection of DNA by a Moving Interface”, Sep. 30, 1994, vol. 265 (5181), Retrieved from www.sciencemag.org on Dec. 20, 2014, 3 pages.

Bergveld P., “Short Communications—Development of an Ion-Sensitive Solid-State Device for Neurophysiological Measurements”, IEEE Transactions on Bio-Medical Engineering, Jan. 1970, 2 pages.

Bergveld P., “Thirty Years of ISFETOLOGY: What Happened in the Past 30 Years and What May Happen in the Next 30 Years”, Jan. 1, 2003, vol. 88 (1), pp. 1-20.

Berlinet A., et al., “Reproducing Kernel Hilbert Spaces in Probability and Statistics,” 2004, 368 pages.

Boyd S., et al., “Convex Optimization,” Cambridge University Press, Retrieved from Internet URL: https://www.cambridge.org/in/academic/subjects/statistics-probability/optimization-or-and-risk/convex-optimization?format=HB&isbn=9780521833783, Retrieved on Mar. 2004, 730 pages.

Bustin S.A., “Quantification of mRNA Using Real-time Reverse Transcription PCR (RT-PCR): Trends and Problems,” Journal of Molecular Endocrinology, 2002, vol. 29, No. 23-39, 17 pages.

Caliendo A.M., et al., “Better Tests, Better Care: Improved Diagnostics for Infectious Diseases,” Clinical Infectious Diseases, 2013, vol. 57, Supplementary. 03, 32 pages.

Carmeli Y., et al., “Controlling the Spread of Carbapenemase-Producing Gram-Negatives: Therapeutic Approach and Infection Control,” Clinical Microbiology and Infection, vol. 16, No. 02, Feb. 2010, 10 pages.

Cero'n-Carrasco J.P., et al., “Electric Field Induced DNA Damage: An Open Door for Selective Mutations”, May 14, 2013, vol. 49 (69), 3 pages.

Chan E.Y., et al., “DNA Mapping Using Microfluidic Stretching and Single-Molecule Detection of Fluorescent Site-Specific Tags,” Jun. 2004, vol. 14 (6), 11 pages.

(Continued)

*Primary Examiner* — Carolyn L Greene
(74) *Attorney, Agent, or Firm* — Merchant & Gould P.C.

(57) ABSTRACT

The present application relates to methods for detecting a first allele of a single nucleotide polymorphism (SNP) in a nucleic acid sequence under isothermal conditions using primers specific for said first allele, in particular using Loop mediated isothermal amplification (LAMP), wherein the amplification of a second allele is prevented by using blocking primers.

20 Claims, 7 Drawing Sheets

Specification includes a Sequence Listing.

(56) References Cited

OTHER PUBLICATIONS

Chong G.M., et al., "PCR-Based Detection of Aspergillus Fumigatus Cyp51A Mutations on Bronchoalveolar Lavage: A Multicentre Validation of the AsperGenius Assay in 201 Patients with Haematological Disease Suspected for Invasive Aspergillosis," Journal of Antimicrobial Chemotherapy, Aug. 15, 2016, vol. 71, 8 pages.
Coleman T.F., et al., "An Interior Trust Region Approach for Nonlinear Minimization Subject to Bounds," Computer Science Department, Cornell University, Apr. 28, 1993, 30 pages.
Coleman T.F., et al., "On the Convergence of Reflective Newton Methods for Large-Scale Nonlinear Minimization Subject to Bounds," Cornell University, Dec. 7, 1992, 36 pages.
Combined Search and Examination Report for Great Britain Application No. 1809420.1, mailed on Feb. 28, 2019, 6 pages.
Combined Search and Examination Report for Great Britain Application No. 1809418.5, mailed on Feb. 6, 2019, 5 pages.
Coomans D., et al., "Use of a Microcomputer for the Definition of Multivariate Confidence Regions in Medical Diagnosis Based on Clinical Laboratory Profiles," Computers and Biomedical Research, vol. 17, Jun. 8, 1983, 14 pages.
Einstein A., "Investigations on the Theory of, The Brownian Movement", Dover Publications, Inc., 1956, 11 pages.
"Electronics Letters—Special Supplement: Semiconductors in Personalised Medicine", IET Journals, Dec. 2011, 8 pages.
Em P.B., "ISFET, Theory and Practice", IEEE Sensor Conference Toronto, Oct. 2003, 26 pages.
Ferre F., et al., "Gene Quantification," Advanced Biomedical Technologies, 1998, 379 pages.
Fischler M.A., et al., "Random Sample Consensus: A Paradigm for Model Fitting with Applications to Image Analysis and Automated Cartography," Communications of the ACM, Jun. 1981, vol. 24, No. 06, 15 pages.
Freeman W.M., et al., "Quantitative RT-PCR: Pitfalls and Potential," Biotechniques, vol. 26, Jan. 1999, 12 pages.
Friedman J., et al., "The Elements of Statistical Learning, Data Mining, Inference and Prediction," Second Edition, Springer, 2001, 764 pages.
Georgiou P., et al., "ISFET Characteristics in CMOS and their Application to Weak Inversion Operation," Sensors and Actuators B, vol. 143, 2009, 7 pages.
Ghani A.C., et al., "Expanding the Role of Diagnostic and Prognostic Tools for Infectious Diseases in Resource-Poor Settings," NATURE, vol. 528, Dec. 3, 2015, 3 pages.
Gingeras T.R., et al., "Fifty Years of Molecular (DNA/RNA) Diagnostics," Clinical Chemistry, vol. 51, No. 03, 2005, 11 pages.
Girones R., et al., "Molecular Detection of Pathogens in Water—The Pros and Cons of Molecular Techniques," Water Research, vol. 44, Jun. 19, 2010, 15 pages.
GOV.UK., "Carbapenemase-Producing Enterobacteriaceae: Laboratory Confirmed Cases, 2003 to 2015," Oct. 10, 2016, 3 pages.
Guescini M., et al., "A New Real-time PCR Method to Overcome Significant Quantitative Inaccuracy due to Slight Amplification Inhibition," BMC Bioinformatics, vol. 09, No. 326, Jul. 30, 2008, 12 pages.
Guescini M., et al., "Accurate and Precise DNA Quantification in the Presence of Different Amplification Efficiencies Using an Improved Cy0 Method," PLOS ONE, vol. 08, Issue. 07, Jul. 2013, 11 pages.
Heid C.A., et al., "Real Time Quantitative PCR," Genome Research, vol. 06, May 18, 2021, 10 pages.
Higuchi R., et al., "Kinetic PCR Analysis: Real-time Monitoring of DNA Amplification Reactions," BIO/TECHNOLOGY, vol. 11, Sep. 1993, 5 pages.
"HIV Drug Resistance Database", Stanford University, Retrieved from Internet URL: https://hivdb.stanford.edu/page/wh0-sdm-list, Retrieved on May 24, 2018, 2 pages.
Hogg R.V., et al., "Probability and Statistical Inference", Ninth Edition, 2006, 557 pages.
Hotelling H., "Analysis of a Complex of Statistical Variables Into Principal Components," Columbia University, 1933, 25 pages.
Hsieh C.C., et al., "Simulation Guided Design of a Microfluidic Device for Electrophoretic Stretching of DNA", AIP Biomicrofluidics, Oct. 24, 2012, vol. 6 (4), 13 pages.
Hu Y., "A Robust ISFET pH-Measuring Front-End for Chemical Reaction Monitoring," IEEE Transactions on Biomedical Circuits and Systems, Apr. 2014, vol. 8 (2), 9 pages.
Hud N.V., "Nucleic Acid-Metal Ion Interactions," RSC Publishing, 2009, 448 pages.
International Preliminary Report on Patentability for Application No. PCT/EP2019/065039 mailed on Dec. 8, 2020, 9 pages.
International Preliminary Report on Patentability for Application No. PCT/EP2019/065046, mailed on Dec. 8, 2020, 9 pages.
International Preliminary Report on Patentability for Application No. PCT/EP2019/065047 mailed on Dec. 8, 2020, 8 pages.
International Preliminary Report on Patentability for Application No. PCT/GB2019/051597 mailed on Dec. 8, 2020, 7 pages.
International Search Report and Written Opinion for Application No. PCT/EP2019/065039 mailed on Oct. 1, 2019, 17 pages.
International Search Report and Written Opinion for Application No. PCT/EP2019/065046, mailed on Jul. 24, 2019, 15 pages.
International Search Report and Written Opinion for Application No. PCT/EP2019/065047 mailed on Sep. 10, 2019, 12 pages.
International Search Report and Written Opinion for Application No. PCT/GB2019/051597 mailed on Sep. 9, 2019, 15 pages.
Jakobson C.G., et al., "1/f Noise in Ion Sensitive Field Effect Transistors from Subthreshold to Saturation", IEEE Transactions on Electron Devices, Jan. 1999, vol. 46 (1), 2 pages.
Kanderian S., et al., "Automated Classification and Cluster Visualization of Genotypes Derived from High Resolution Melt Curves," PLOS ONE, Nov. 25, 2015, vol. 10, No. 11, 14 pages.
Klein D., "Quantification Using Real-time PCR Technology: Applications and Limitations," TRENDS in Molecular Medicine, vol. 08, No. 06, Jun. 2002, 4 pages.
Lagarias J.C., et al., "Convergence Properties of the Nelder-Mead Simplex Method in Low Dimensions," Society for Industrial and Applied Mathematics, vol. 09, No. 01, Dec. 2, 1998, 36 pages.
Lee C.H., et al., "Stretching DNA by Electric Field and Flow Field in Microfluidic Devices: An Experimental Validation to the Devices Designed with Computer Simulations," Feb. 8, 2013, vol. 7 (1), 14 pages.
Lee Y., et al., "Single-Channel Multiplexing Without Melting Curve Analysis in Real-Time PCR," Scientific Reports, Dec. 11, 2014, vol. 4, 6 pages.
Lenseigne B., et al., "Support Vector Machines for Automatic Detection of Tuberculosis Bacteria in Confocal Microscopy Images," Biomedical Imaging: From Nano to Macro, 2007, pp. 85-88.
Levenberg K., "A Method for the Solution of Certain Non-Linear Problems in Least Squares," Quarterly of Applied Mathematics, Jul. 1944, vol. 2, No. 2, pp. 164-168.
Lim S.F., et al., "DNA Methylation Profiling in Nanochannels", Jul. 25, 2011, vol. 5 (3), 8 pages.
Liu C., et al., "Nuclemeter: A Reaction-Diffusion Based Method for Quantifying Nucleic Acids Undergoing Enzymatic Amplification", Dec. 5, 2014, 7 pages.
Lowe D.G., "Object Recognition from Local Scale-Invariant Features", Sep. 1999, 8 pages.
Lu Y., et al., "Visualized Detection of Single-Base Difference in Multiplexed Loop-Mediated Isothermal Amplification Amplicons by Invasive Reaction Coupled With Oligonucleotide Probe-Modified Gold Nanoparticles," Biosensors and Bioelectronics, Apr. 15, 2017, vol. 90, pp. 388-393.
Ma D., et al., "Adapting ISFETs for Epigenetics: An Overview," IEEE Transactions on Biomedical Circuits and Systems, vol. 12, No. 05, Oct. 2018, 8 pages.
Mackay I.M., et al., "Survey And Summary Real-Time PCR in Virology," Nucleic Acids Research, 2002, vol. 30, No. 6, pp. 1292-1305.
Maesschalck R.D., et al., "The Mahalanobis Distance," Chemometrics and Intelligent Laboratory Systems, vol. 50, 2000, 18 pages.

(56) References Cited

OTHER PUBLICATIONS

Malpartida-Cardenas K., et al., "Allele-Specific Isothermal Amplification Method Using Unmodified Self-Stabilizing Competitive Primers," Analytical Chemistry, Sep. 18, 2018, vol. 90, pp. 11972-11980.
Malpartida-Cardenas K., et al., "Quantitative and Rapid Plasmodium Falciparum Malaria Diagnosis and Artemisinin-Resistance Detection Using a CMOS Lab-On-Chip Platform," Biosensors and Bioelectronics, Aug. 1, 2019, vol. 145, 16 pages.
Manzano J.R., et al., "Reading Out Single-Molecule Digital RNA and DNA Isothermal Amplification in Nanoliter Volumes with Unmodified Camera Phones," ACSNANO, Retrieved from Internet URL: https://pubs.acs.org/doi/abs/10.1021/acsnano.5b07338, Retrieved on Feb. 3, 2016, 12 pages.
Marquardt D.W., "An Algorithm for Least-Squares Estimation of Nonlinear Parameters," Journal of the Society for Industrial and Applied Mathematics, Jun. 1963, vol. 11, No. 2, pp. 431-441.
Mclachlan G.J., "Mahalanobis Distance," RESONANCE, Jun. 1999, pp. 20-26.
Michalet X., et al., "Dynamic Molecular Combing: Stretching the Whole Human Genome for High-Resolution Studies", Sep. 5, 1997, vol. 277 (5331), 7 pages.
Misyura M., et al., "Improving Validation Methods for Molecular Diagnostics: Application of Bland-Altman, Deming and Simple Linear Regression Analyses in Assay Comparison and Evaluation for Next-Generation Sequencing," Journal of Clinical Pathology (2018), Jul. 26, 2017, vol. 71, pp. 117-124.
Mohon A.N., et al., "A Novel Single-Nucleotide Polymorphism Loop Mediated Isothermal Amplification Assay for Detection of Artemisinin-Resistant Plasmodium falciparum Malaria," Open Forum Infectious disease, Jan. 9, 2018, vol. 4, No. 4, 8 pages.
Moniri A., et al., "Framework for DNA Quantification and Outlier Detection Using Multidimensional Standard Curves," Analytical Chemistry, May 6, 2019, vol. 91, No. 11, pp. 7426-7434.
Monterio., et al., "Rapid Detection of Carbapenemase Genes by Multiplex Real-Time PCR," Journal of Antimicrobial Chemotheraphy, Jan. 9, 2012, vol. 67, No. 4, pp. 906-909.
Moore J.W., et al., "The Molecular Science," Chemistry 3rd Edition, 2005, 1287 pages.
Moreno A.C., et al., "Azole-resistant Aspergillus Fumigatus Harboring TR34/L98H,, TR46/Y121F/T289A and TR53 Mutations Related to Flower Fields in Colombia," Scientific Reports, vol. 07, No. 45631, Retrieved from Internet URL: https://www.nature.com/articles/srep45631, Retrieved on Mar. 30, 2017, 8 pages.
Mori Y., et al., "Real-Time Turbidimetry of LAMP Reaction for Quantifying Template DNA", Journal of Biochemical and Biophysical Methods, May 31, 2004, vol. 59 (2), pp. 145-157.
Moser N., et al., "A Scalable ISFET Sensing and Memory Array With Sensor Auto-Calibration for On-Chip Real-Time DNA Detection," IEEE Transactions on Biomedical Circuits and Systems, Apr. 1, 2018, vol. 12, No. 2, XP855617882, ISSN: 1932-4545, DOI:18.1109/TBCAS.2017.2789161, pp. 390-401.
Moser N., et al., "An lon Imaging ISFET Array for Potassium and Sodium Detection," Retrieved on Jun. 26, 2021, 4 pages.
Moser N., et al., "ISFETs in CMOS and Emergent Trends in Instrumentation: A Review," IEEE Sensors Journal, vol. 16, No. 17, Sep. 1, 2016, 19 pages.
Nelder J.A., et al., "A Simplex Method for Function Minimization," The Computer Journal, vol. 7, Issue 4, Jan. 1965, pp. 308-313.
Nolan T., et al., "Quantification of mRNA using Real-Time RT-PCR," Nature Protocols, Nov. 9, 2006, vol. 1, No. 3, pp. 1559-1582.
Notomi T., et al., "Loop-Meditated Isothermal Amplification of DNA", Nucleic Acid Research, Jun. 15, 2000, vol. 28 (12), 7 pages.
Orou A., et al., "Allele-Specific Competitive Blocker PCR: A One-Step Method with Applicability to Pool Screening," Human Mutation, 1995, vol. 6, No. 2, pp. 163-169.
Otter J.A., et al., "Counting the Cost of an Outbreak of Carbapenemase-Producing Enterobacteriaceae: An Economic Evaluation From a Hospital Perspective," Clinical Microbiology and Infection, Oct. 13, 2016, vol. 23, vol. 3, pp. 188-196.
Otter J.O., et al., "Emergence and Clonal Spread of Colistin Resistance Due to Multiple Mutational Mechanisms in Carbapenemase-Producing Klebsiella Pneumoniae in London," Scientific Reports, Oct. 5, 2017, vol. 7, 8 pages.
Parida M., et al., "Loop Mediated Isothermal Amplification (LAMP): A New Generation of Innovative Gene Amplification Technique; Perspectives in Clinical Diagnosis of Infectious Diseases", 2008, vol. 18 (6), pp. 407-421.
Pearson K., "LIII. On Lines and Planes of Closest Fit to Systems of Points in Space," The London, Edinburgh, and Dublin Philosophical Magazine and Journal of Science, Jun. 8, 2010, vol. 2,Issue 11, pp. 559-572.
Phillips K.M., et al., "Application of Single Molecule Technology to Rapidly Map Long DNA and Study the Conformation of Stretched DNA," Nucleic Acids Research, Oct. 20, 2005, vol. 33 (18), pp. 5829-5837.
Purushothaman S., et al., "Protons and Single Nucleotide Polymorphism Detection: A Simple Use for the Ion Sensitive Field Effect Transistor," Apr. 2006, vol. 114 (2), 5 pages.
Randall G.C., et al., "DNA Deformation in Electric Fields: DNA Driven Past a Cylindrical Obstruction", Macromolecules, 2005, vol. 38 (6), pp. 2410-2418.
Randall G.C., et al., "Methods to Electrophoretically Stretch DNA: Microcontractions, Gels, and Hybrid Gel-Microcontraction Devices", Mar. 7, 2006, 10 pages.
Rao X., et al., "A New Method for Quantitative Real-Time Polymerase Chain Reaction Data Analysis," Journal of Computational Biology, 2013, vol. 20, No. 9, pp. 703-711.
Regmi S.M., et al., "Polymorphisms In Drug-Resistant-Related Genes shared Among Drug-Resistant and Pan-Susceptible Strains of Sequence Type 10, Beijing Family Of Mycobacterium Tuberculosis," International Journal of Mycobacteriology, vol. 4, Issue.1, Jan. 9, 2015, pp. 67-72.
Reisner W., et al., "Statics and Dynamics of Single DNA Molecules Confined in Nanochannels", May 20, 2005, vol. 94 (19), 4 pages.
Rutledge R.G., "Sigmoidal curve-fitting redefines quantitative real-time PCR with the prospective of developing automated high-throughput applications," Nucleic Acids Research, Dec. 15, 2004, vol. 32, No. 22, 8 pages.
Saiki R.K., et al., "Enzymatic Amplification of β-Globin Genomic Sequences and Restriction Site Analysis for Diagnosis of Sickle Cell Anemia", Dec. 20, 1985, Retrieved from http://science.sciencemag.org/ on Jun. 23, 2021, vol. 230 (4732), pp. 1350-1354.
Salant H., "The Development of a Loop-Mediated Isothermal Amplification Method (LAMP) for Echinococcus Granulosis Coprodetection," Am J Trop Med Hyg, Sep. 17, 2012, vol. 87 (5), pp. 883-837.
Salm E., et al., "Electrical Detection of Nucleic Acid Amplification Using an On-Chip Quasi-Reference Electrode and a PVC REFET," Analytical Chemistry, Jul. 15, 2014, vol. 86, No. 14, XP055329876, ISSN: 0003-2700, DOI:10.1021/ac500897t, pp. 6968-6975.
Sekyere J.O., et al., "Review of Established and Innovative Detection Methods for Carbapenemase-Producing Gram-Negative Bacteria," Journal of Applied Microbiology, Jul. 23, 2015, 15 pages.
Sisti D., et al., Shape based Kinetic Outlier Detection in Real-Time PCR, BMC Bioinformatics, 2010, vol. 11, No. 186, 12 pages.
Song J., et al., "Molecular Detection of Schistosome Infections with a Disposable Microfluidic Cassette," PLOS Neglected Tropical Diseases, Dec. 31, 2015, 18 pages.
Spiess A., et al., "Highly accurate sigmoidal fitting of real-time PCR data by introducing a parameter for asymmetry," BMC Bioinformatics, Apr. 29, 2008, vol. 9, No. 221, 12 pages.
Subramanian S., et al., "An Empirical Approach for Quantifying Loop-Mediated Isothermal Amplification (LAMP) Using *Escherichia coli* as a Model System", Jun. 2014, vol. 9 (6), 10 pages.
Tegenfeldt J.O., et al., "The Dynamics of Genomic-Length DNA Molecules in 100-nm Channels," Jul. 27, 2004, vol. 101 (30), pp. 10979-10983.
Toumazou C., et al., "A New Era of Semiconductor Genetics Using lon-Sensitive Field-Effect Transistors: The Gene-Sensitive Integrated Cell," Mar. 28, 2014, Retrieved from https://royalsocietypublishing.org/ on Jun. 23, 2021, 12 pages.

(56) References Cited

OTHER PUBLICATIONS

Toumazou C., et al., "Simultaneous DNA Amplification and Detection using a pH-Sensing Semiconductor System," Nature Methods, Jul. 1, 2013, vol. 10, No. 7, XP055329877, ISSN: 15487091, DOI:10.1038/nmeth.2520, pp. 641-646.
Van Der Maaten L., et al., "Dimensionality Reduction: A Comparative Review," TiCC TR 2009-005, Oct. 26, 2009, 36 pages.
Van Duin D., et al., "The Global Epidemiology of Carbapenemase-Producing Enterobacteriaceae," VIRULENCE, 2017, vol. 8, No. 4, Retrieved from the Internet: https://doi.org/10.1080/21505594.2016.1222343, pp. 460-469.
Viau R., et al., "Intestinal Carriage of Carbapenemase-Producing Organisms: Current Status of Surveillance Methods," Clinical Microbiology Reviews, Jan. 2016, vol. 29, No. 1, pp. 1-27.
WHO, "Dengue Guidelines for Diagnosis, Treatment, Prevention and Control," New Edition 2009, 160 pages.
Wittwer C.T., et al., "Continuous Fluorescence Monitoring of Rapid Cycle DNA Amplification," Bio Techniques, Jan. 1997, vol. 22, No. 1, pp. 130-138 (7pages).
Wold S., et al., "PLS-Regression: A Basic Tool of Chemometrics," Chemometrics and Intelligent Laboratory Systems, 2001, vol. 58, pp. 109-130.
Young S.S., et al., "Deming, Data and Observational Studies—A Process Out of Control and Needing Fixing", Aug. 25, 2011, 5 pages.
Yu L.S., et al., "Rapid and Sensitive Detection of Azole-Resistant Aspergillus Fumigatus by Tandem Repeat Loop-Mediated Isothermal Amplification," The Journal of Molecular Diagnostics, Mar. 2019, vol. 21, No. 2, pp. 286-295.
Zhang C., et al., "Establishment and Application of a Real-Time Loop-Mediated Isothermal Amplification System for the Detection of CYP2C19 Polymorphisms," Scientific Reports, vol. 06, No. 26533, Jun. 1, 2016, 7 pages.
BIOFIRE Respiratory 2.1 Plus Oanel :BIOFIRE FILMARRAY Respiratory Panel, Retrieved from Internet URL: https://www.biofiredx.com/products/the-filmarray-panels/filmarrayrp/, 2016, 9 page.
Alere E. "ID NOW INELLIENZA A & B 2—There is No Time ID Now", Retrieved from Internet URL: https://www.globalpointofcare.abbott/us/en/product-details/id-now-influenza-ab-2.html, 2016, 1 page.
BIOFIRE Respiratory 2.1 Plus Panel :BIOFIRE FILMARRAY Respiratory Panel, Retrieved from Internet URL: https://www.biofiredx.com/products/the-filmarray-panels/filmarrayrp/, 2016, 9 page.
CEPHEID "Xpert Xpress Flu/RSV, https://www.cepheid.com/en-AU/tests/respiratory/xpert-xpress-flu-rsv.html, "2016, 1 page.
Cobas, Liat, System, Roche Diagnostics Website, Retrieved from Internet URL: https://diagnosties.roche.com/gloabal/on/products/instruments/oobas.liat.html, retrieved on Mar. 25, 2022, 1 page.
ENZOKLOP "File: Polymerase Chain Reaction.svg, Polymerase Chain Reaction-PCR," 2016, 1 page.
MATHWORKS, "Supervised Learning Workflow and Algorithms," 2021, 1 page.
Moser., et al. "Live Demonstraction: A CMOS-Based ISFET Array for Rapid Diagnosis of the Zika Virus," 2017 IEEE International Sysmposium on Circuits and Systems (ISCAS), 28, May 31, 2017, 1 page.

* cited by examiner

A
B
WT sp. rxn
MT sp. rxn
y = -3.60x + 30.45
R² = 0.989
y = -3.33x + 31.74
R² = 0.975
y = -4.14x + 39.59
R² = 0.994
y = -3.38x + 33.29
R² = 0.996
C_T (min)
DNA (cp/rxn)
5x10¹
5x10²
5x10³
5x10⁴

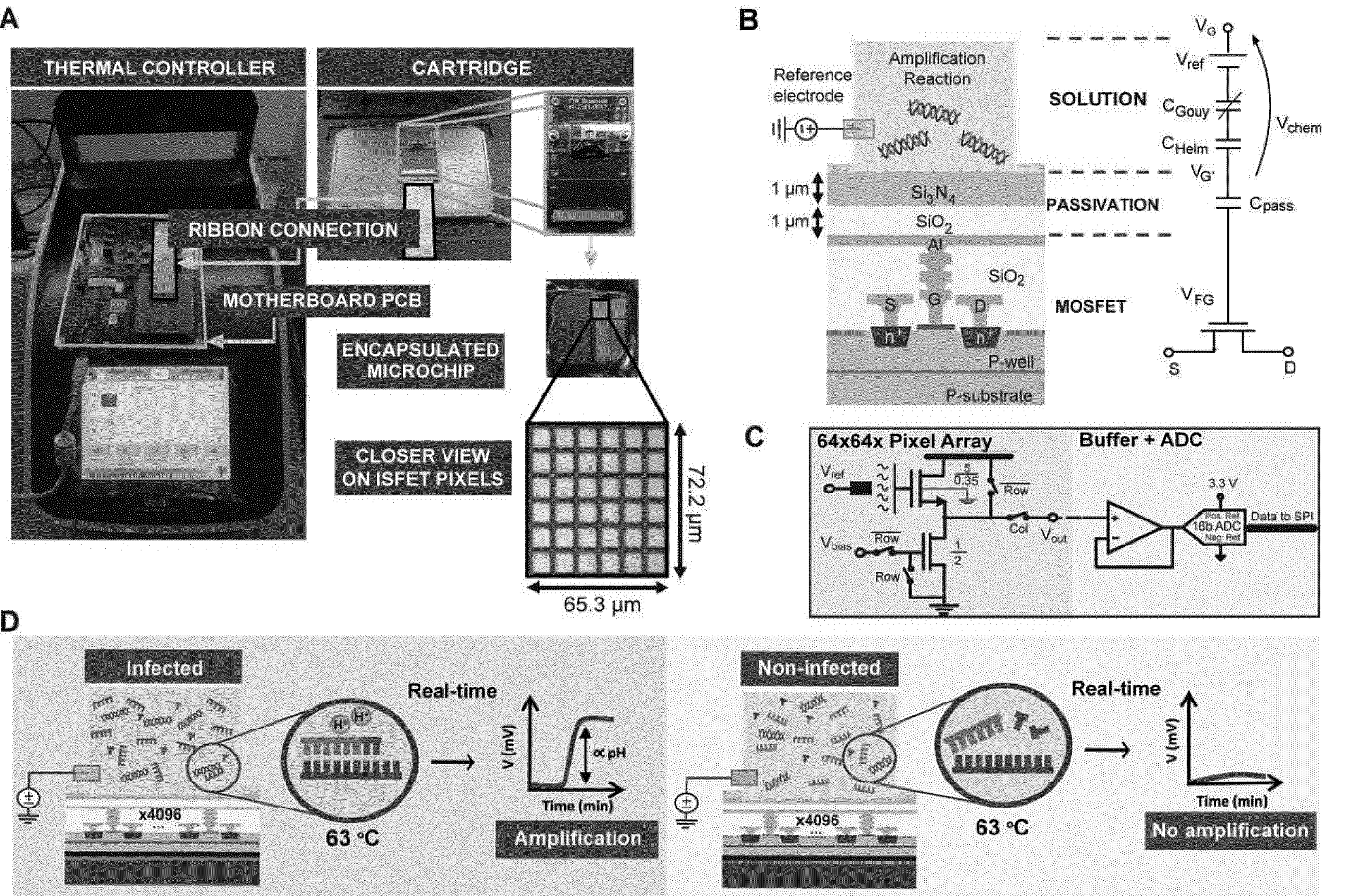
Figure 6
A
THERMAL CONTROLLER
CARTRIDGE
RIBBON CONNECTION
MOTHERBOARD PCB
ENCAPSULATED MICROCHIP
CLOSER VIEW ON ISFET PIXELS
72.2 µm
65.3 µm
B
Reference electrode
Amplification Reaction
1 µm
1 µm
$Si_3N_4$
$SiO_2$
Al
$SiO_2$
S
G
D
$n^+$
$n^+$
P-well
P-substrate
SOLUTION
PASSIVATION
MOSFET
$V_G$
$V_{ref}$
$C_{Gouy}$
$C_{Helm}$
$V_{G'}$
$V_{chem}$
$C_{pass}$
$V_{FG}$
S
D
C
64x64x Pixel Array
$V_{ref}$
$V_{bias}$
Row
Row
Row
Col
$V_{out}$
Buffer + ADC
3.3 V
Pos. Ref
16b ADC
Neg. Ref
Data to SPI
D
Infected
x4096
Real-time
63 °C
V (mV)
∝ pH
Time (min)
Amplification
Non-infected
x4096
Real-time
63 °C
V (mV)
Time (min)
No amplification

SEQUENCE LISTING

```
<160> NUMBER OF SEQ ID NOS: 102

<210> SEQ ID NO 1
<211> LENGTH: 40
<212> TYPE: DNA
<213> ORGANISM: Artificial Sequence
<220> FEATURE:
<223> OTHER INFORMATION: Primer

<400> SEQUENCE: 1

tacatagctg atgatcttat gatcatcgta tgaaagcatg                    40


<210> SEQ ID NO 2
<211> LENGTH: 49
<212> TYPE: DNA
<213> ORGANISM: Artificial Sequence
<220> FEATURE:
<223> OTHER INFORMATION: Primer

<400> SEQUENCE: 2

atgttgcttt tgataataaa atttatgcta ataaggcata tggaaattg          49


<210> SEQ ID NO 3
<211> LENGTH: 28
<212> TYPE: DNA
<213> ORGANISM: Artificial Sequence
<220> FEATURE:
<223> OTHER INFORMATION: Primer
```

```
<400> SEQUENCE: 3

tgtgttgctt ttgataataa aatttatg                                        28


<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4

cacacatagc tgatgatcta ggg                                             23


<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5

ctattatacc gaatgtagaa gca                                             23


<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6

tgctcctgaa cttctagc                                                   18


<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7

tcaaaggtgc cacctctacc                                                 20


<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8

ggtggaacta atggtgagag attaa                                           25


<210> SEQ ID NO 9
<211> LENGTH: 46
<212> TYPE: DNA
<213> ORGANISM: Artificial Sequence
<220> FEATURE:
<223> OTHER INFORMATION: Primer

<400> SEQUENCE: 9

gtaagaaatt attcaataca gattagatat tagtcaacaa tgctgg                    46


<210> SEQ ID NO 10
<211> LENGTH: 38
```

<212> TYPE: DNA
<213> ORGANISM: Artificial Sequence
<220> FEATURE:
<223> OTHER INFORMATION: Primer

<400> SEQUENCE: 10
cacgtttttg gtggtaaaaa cgatcataca cctcagtt 38

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
atacgttttt ggtggtaata actat 25

<210> SEQ ID NO 12
<211> LENGTH: 26
<212> TYPE: DNA
<213> ORGANISM: Artificial Sequence
<220> FEATURE:
<223> OTHER INFORMATION: Primer

<400> SEQUENCE: 12
ataagaaatt attcaataca gcactt 26

<210> SEQ ID NO 13
<211> LENGTH: 25
<212> TYPE: DNA
<213> ORGANISM: Artificial Sequence
<220> FEATURE:
<223> OTHER INFORMATION: Primer

<400> SEQUENCE: 13
ggtgtagaat atttaaattc gatgg 25

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
ttgaaacata ccatacatct ctt 23

<210> SEQ ID NO 15
<211> LENGTH: 25
<212> TYPE: DNA
<213> ORGANISM: Artificial Sequence
<220> FEATURE:
<223> OTHER INFORMATION: Primer

<400> SEQUENCE: 15
tggtagacat aggtgtacac atacg 25

<210> SEQ ID NO 16
<211> LENGTH: 19
<212> TYPE: DNA
<213> ORGANISM: Artificial Sequence
<220> FEATURE:
<223> OTHER INFORMATION: Primer

<400> SEQUENCE: 16
attataaggc tttatttga 19

<210> SEQ ID NO 17
<211> LENGTH: 44
<212> TYPE: DNA
<213> ORGANISM: Artificial Sequence
<220> FEATURE:
<223> OTHER INFORMATION: Primer

<400> SEQUENCE: 17
gtaccatttg acgtaacact aagagatgta tggtatgttt caag 44

<210> SEQ ID NO 18
<211> LENGTH: 43
<212> TYPE: DNA
<213> ORGANISM: Artificial Sequence
<220> FEATURE:
<223> OTHER INFORMATION: Primer

<400> SEQUENCE: 18
caatttattg tattggggga tcatatgctt ctacattcgg tat 43

<210> SEQ ID NO 19
<211> LENGTH: 25
<212> TYPE: DNA
<213> ORGANISM: Artificial Sequence
<220> FEATURE:
<223> OTHER INFORMATION: Primer

<400> SEQUENCE: 19
tagaatttat tgtattgggg gatat 25

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
ctaccatttg acgtaacacc ac 22

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
aactgaggtg tatgatcgtt 20

<210> SEQ ID NO 22
<211> LENGTH: 18
<212> TYPE: DNA
<213> ORGANISM: Artificial Sequence
<220> FEATURE:
<223> OTHER INFORMATION: Primer

<400> SEQUENCE: 22
acccatgctt tcatacga 18

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
ttatttcttc taggtatatt t 21

<210> SEQ ID NO 24
<211> LENGTH: 17
<212> TYPE: DNA
<213> ORGANISM: Artificial Sequence
<220> FEATURE:
<223> OTHER INFORMATION: Primer

<400> SEQUENCE: 24
atgatggctc ttctatt 17

<210> SEQ ID NO 25
<211> LENGTH: 40
<212> TYPE: DNA
<213> ORGANISM: Artificial Sequence
<220> FEATURE:
<223> OTHER INFORMATION: Primer

<400> SEQUENCE: 25
tacatagctg atgatcttat gatcatcgta tgaaagcatg 40

<210> SEQ ID NO 26
<211> LENGTH: 49
<212> TYPE: DNA
<213> ORGANISM: Artificial Sequence
<220> FEATURE:
<223> OTHER INFORMATION: Primer

<400> SEQUENCE: 26
atgttgcttt tgataataaa atttatgcta ataaggcata tggaaattg 49

<210> SEQ ID NO 27
<211> LENGTH: 28
<212> TYPE: DNA
<213> ORGANISM: Artificial Sequence
<220> FEATURE:
<223> OTHER INFORMATION: Primer

<400> SEQUENCE: 27
tgtgttgctt ttgataataa aatttatg 28

<210> SEQ ID NO 28
<211> LENGTH: 23
<212> TYPE: DNA
<213> ORGANISM: Artificial Sequence
<220> FEATURE:
<223> OTHER INFORMATION: Primer

<400> SEQUENCE: 28
cacacatagc tgatgatcta ggg 23

<210> SEQ ID NO 29
<211> LENGTH: 40
<212> TYPE: DNA
<213> ORGANISM: Artificial Sequence
<220> FEATURE:
<223> OTHER INFORMATION: Primer

<400> SEQUENCE: 29
cacatagctg atgatcttat gatcatcgta tgaaagcatg 40

<210> SEQ ID NO 30
<211> LENGTH: 49
<212> TYPE: DNA
<213> ORGANISM: Artificial Sequence
<220> FEATURE:
<223> OTHER INFORMATION: Primer

<400> SEQUENCE: 30
gtgttgcttt tgataataaa atttatgcta ataaggcata tggaaattg 49

<210> SEQ ID NO 31
<211> LENGTH: 35
<212> TYPE: DNA
<213> ORGANISM: Artificial Sequence
<220> FEATURE:
<223> OTHER INFORMATION: Primer

<400> SEQUENCE: 31
gtatgttgct tttgataata aaatttatgt cattg 35

<210> SEQ ID NO 32
<211> LENGTH: 22
<212> TYPE: DNA
<213> ORGANISM: Artificial Sequence
<220> FEATURE:
<223> OTHER INFORMATION: Primer

<400> SEQUENCE: 32
atacatagct gatgatctag gg 22

<210> SEQ ID NO 33
<211> LENGTH: 23
<212> TYPE: DNA
<213> ORGANISM: Artificial Sequence
<220> FEATURE:
<223> OTHER INFORMATION: Primer

<400> SEQUENCE: 33
ctattatacc gaatgtagaa gca 23

<210> SEQ ID NO 34
<211> LENGTH: 18
<212> TYPE: DNA
<213> ORGANISM: Artificial Sequence
<220> FEATURE:
<223> OTHER INFORMATION: Primer

<400> SEQUENCE: 34
tgctcctgaa cttctagc 18

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
tcaaaggtgc cacctctacc 20

<210> SEQ ID NO 36
<211> LENGTH: 25
<212> TYPE: DNA
<213> ORGANISM: Artificial Sequence
<220> FEATURE:
<223> OTHER INFORMATION: Primer

<400> SEQUENCE: 36
ggtggaacta atggtgagag attaa 25

<210> SEQ ID NO 37
<211> LENGTH: 46
<212> TYPE: DNA
<213> ORGANISM: Artificial Sequence
<220> FEATURE:
<223> OTHER INFORMATION: Primer

<400> SEQUENCE: 37
gtaagaaatt attcaataca gattagatat tagtcaacaa tgctgg 46

<210> SEQ ID NO 38
<211> LENGTH: 38
<212> TYPE: DNA
<213> ORGANISM: Artificial Sequence
<220> FEATURE:
<223> OTHER INFORMATION: Primer

<400> SEQUENCE: 38
cacgtttttg gtggtaaaaa cgatcataca cctcagtt 38

<210> SEQ ID NO 39
<211> LENGTH: 25
<212> TYPE: DNA
<213> ORGANISM: Artificial Sequence
<220> FEATURE:
<223> OTHER INFORMATION: Primer

<400> SEQUENCE: 39
atacgttttt ggtggtaata actat 25

<210> SEQ ID NO 40
<211> LENGTH: 26
<212> TYPE: DNA
<213> ORGANISM: Artificial Sequence
<220> FEATURE:
<223> OTHER INFORMATION: Primer

<400> SEQUENCE: 40
ataagaaatt attcaataca gcactt 26

<210> SEQ ID NO 41
<211> LENGTH: 46
<212> TYPE: DNA
<213> ORGANISM: Artificial Sequence
<220> FEATURE:
<223> OTHER INFORMATION: Primer

<400> SEQUENCE: 41
ataagaaatt attcaataca gattagatat tagtcaacaa tgctgg 46

<210> SEQ ID NO 42
<211> LENGTH: 38
<212> TYPE: DNA
<213> ORGANISM: Artificial Sequence
<220> FEATURE:
<223> OTHER INFORMATION: Primer

<400> SEQUENCE: 42
tacgtttttg gtggtaaaaa cgatcataca cctcagtt 38

<210> SEQ ID NO 43

<211> LENGTH: 26
<212> TYPE: DNA
<213> ORGANISM: Artificial Sequence
<220> FEATURE:
<223> OTHER INFORMATION: Primer

<400> SEQUENCE: 43
tacacgtttt tggtggtaat aactat 26

<210> SEQ ID NO 44
<211> LENGTH: 27
<212> TYPE: DNA
<213> ORGANISM: Artificial Sequence
<220> FEATURE:
<223> OTHER INFORMATION: Primer

<400> SEQUENCE: 44
tgtaagaaat tattcaatac agcactt 27

<210> SEQ ID NO 45
<211> LENGTH: 25
<212> TYPE: DNA
<213> ORGANISM: Artificial Sequence
<220> FEATURE:
<223> OTHER INFORMATION: Primer

<400> SEQUENCE: 45
ggtgtagaat atttaaattc gatgg 25

<210> SEQ ID NO 46
<211> LENGTH: 23
<212> TYPE: DNA
<213> ORGANISM: Artificial Sequence
<220> FEATURE:
<223> OTHER INFORMATION: Primer

<400> SEQUENCE: 46
ttgaaacata ccatacatct ctt 23

<210> SEQ ID NO 47
<211> LENGTH: 25
<212> TYPE: DNA
<213> ORGANISM: Artificial Sequence
<220> FEATURE:
<223> OTHER INFORMATION: Primer

<400> SEQUENCE: 47
tggtagacat aggtgtacac atacg 25

<210> SEQ ID NO 48
<211> LENGTH: 19
<212> TYPE: DNA
<213> ORGANISM: Artificial Sequence
<220> FEATURE:
<223> OTHER INFORMATION: Primer

<400> SEQUENCE: 48
attataaggc tttatttga 19

<210> SEQ ID NO 49
<211> LENGTH: 44
<212> TYPE: DNA
<213> ORGANISM: Artificial Sequence
<220> FEATURE:
<223> OTHER INFORMATION: Primer

<400> SEQUENCE: 49
gtaccatttg acgtaacact aagagatgta tggtatgttt caag 44

<210> SEQ ID NO 50
<211> LENGTH: 43
<212> TYPE: DNA
<213> ORGANISM: Artificial Sequence
<220> FEATURE:
<223> OTHER INFORMATION: Primer

<400> SEQUENCE: 50
caatttattg tattggggga tcatatgctt ctacattcgg tat 43

<210> SEQ ID NO 51
<211> LENGTH: 25
<212> TYPE: DNA
<213> ORGANISM: Artificial Sequence
<220> FEATURE:
<223> OTHER INFORMATION: Primer

<400> SEQUENCE: 51
tagaatttat tgtattgggg gatat 25

<210> SEQ ID NO 52
<211> LENGTH: 22
<212> TYPE: DNA
<213> ORGANISM: Artificial Sequence
<220> FEATURE:
<223> OTHER INFORMATION: Primer

<400> SEQUENCE: 52
ctaccatttg acgtaacacc ac 22

<210> SEQ ID NO 53
<211> LENGTH: 42
<212> TYPE: DNA
<213> ORGANISM: Artificial Sequence
<220> FEATURE:
<223> OTHER INFORMATION: Primer

<400> SEQUENCE: 53
ctaccatttg acgtaactaa gagatgtatg gtatgtttca ag 42

<210> SEQ ID NO 54
<211> LENGTH: 44
<212> TYPE: DNA
<213> ORGANISM: Artificial Sequence
<220> FEATURE:
<223> OTHER INFORMATION: Primer

<400> SEQUENCE: 54
agaatttatt gtattggggg atcatatgct tctacattcg gtat 44

<210> SEQ ID NO 55
<211> LENGTH: 25
<212> TYPE: DNA
<213> ORGANISM: Artificial Sequence
<220> FEATURE:
<223> OTHER INFORMATION: Primer

<400> SEQUENCE: 55
tacaatttat tgtattgggg gatat 25

<210> SEQ ID NO 56
<211> LENGTH: 23
<212> TYPE: DNA

<213> ORGANISM: Artificial Sequence
<220> FEATURE:
<223> OTHER INFORMATION: Primer

<400> SEQUENCE: 56
tgtaccattt gacgtaacac cac 23

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
aactgaggtg tatgatcgtt 20

<210> SEQ ID NO 58
<211> LENGTH: 18
<212> TYPE: DNA
<213> ORGANISM: Artificial Sequence
<220> FEATURE:
<223> OTHER INFORMATION: Primer

<400> SEQUENCE: 58
acccatgctt tcatacga 18

<210> SEQ ID NO 59
<211> LENGTH: 21
<212> TYPE: DNA
<213> ORGANISM: Artificial Sequence
<220> FEATURE:
<223> OTHER INFORMATION: Primer

<400> SEQUENCE: 59
ttatttcttc taggtatatt t 21

<210> SEQ ID NO 60
<211> LENGTH: 17
<212> TYPE: DNA
<213> ORGANISM: Artificial Sequence
<220> FEATURE:
<223> OTHER INFORMATION: Primer

<400> SEQUENCE: 60
atgatggctc ttctatt 17

<210> SEQ ID NO 61
<211> LENGTH: 23
<212> TYPE: DNA
<213> ORGANISM: Artificial Sequence
<220> FEATURE:
<223> OTHER INFORMATION: Primer

<400> SEQUENCE: 61
ctattatacc gaatgtagaa gca 23

<210> SEQ ID NO 62
<211> LENGTH: 18
<212> TYPE: DNA
<213> ORGANISM: Artificial Sequence
<220> FEATURE:
<223> OTHER INFORMATION: Primer

<400> SEQUENCE: 62
tgctcctgaa cttctagc 18

<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
tcaaaggtgc cacctctacc 20

<210> SEQ ID NO 64
<211> LENGTH: 25
<212> TYPE: DNA
<213> ORGANISM: Artificial Sequence
<220> FEATURE:
<223> OTHER INFORMATION: Primer

<400> SEQUENCE: 64
ggtggaacta atggtgagag attaa 25

<210> SEQ ID NO 65
<211> LENGTH: 40
<212> TYPE: DNA
<213> ORGANISM: Artificial Sequence
<220> FEATURE:
<223> OTHER INFORMATION: Primer

<400> SEQUENCE: 65
cacatagctg atgatcttat gatcatcgta tgaaagcatg 40

<210> SEQ ID NO 66
<211> LENGTH: 49
<212> TYPE: DNA
<213> ORGANISM: Artificial Sequence
<220> FEATURE:
<223> OTHER INFORMATION: Primer

<400> SEQUENCE: 66
gtgttgcttt tgataataaa atttatgcta ataaggcata tggaaattg 49

<210> SEQ ID NO 67
<211> LENGTH: 40
<212> TYPE: DNA
<213> ORGANISM: Artificial Sequence
<220> FEATURE:
<223> OTHER INFORMATION: Primer

<400> SEQUENCE: 67
tacatagctg atgatcttat gatcatcgta tgaaagcatg 40

<210> SEQ ID NO 68
<211> LENGTH: 49
<212> TYPE: DNA
<213> ORGANISM: Artificial Sequence
<220> FEATURE:
<223> OTHER INFORMATION: Primer

<400> SEQUENCE: 68
atgttgcttt tgataataaa atttatgcta ataaggcata tggaaattg 49

<210> SEQ ID NO 69
<211> LENGTH: 35
<212> TYPE: DNA
<213> ORGANISM: Artificial Sequence
<220> FEATURE:

<223> OTHER INFORMATION: Primer

<400> SEQUENCE: 69
gtatgttgct tttgataata aaatttatgt cattg 35

<210> SEQ ID NO 70
<211> LENGTH: 22
<212> TYPE: DNA
<213> ORGANISM: Artificial Sequence
<220> FEATURE:
<223> OTHER INFORMATION: Primer

<400> SEQUENCE: 70
atacatagct gatgatctag gg 22

<210> SEQ ID NO 71
<211> LENGTH: 28
<212> TYPE: DNA
<213> ORGANISM: Artificial Sequence
<220> FEATURE:
<223> OTHER INFORMATION: Primer

<400> SEQUENCE: 71
tgtgttgctt ttgataataa aatttatg 28

<210> SEQ ID NO 72
<211> LENGTH: 23
<212> TYPE: DNA
<213> ORGANISM: Artificial Sequence
<220> FEATURE:
<223> OTHER INFORMATION: Primer

<400> SEQUENCE: 72
cacacatagc tgatgatcta ggg 23

<210> SEQ ID NO 73
<211> LENGTH: 25
<212> TYPE: DNA
<213> ORGANISM: Artificial Sequence
<220> FEATURE:
<223> OTHER INFORMATION: Primer

<400> SEQUENCE: 73
ggtgtagaat atttaaattc gatgg 25

<210> SEQ ID NO 74
<211> LENGTH: 23
<212> TYPE: DNA
<213> ORGANISM: Artificial Sequence
<220> FEATURE:
<223> OTHER INFORMATION: Primer

<400> SEQUENCE: 74
ttgaaacata ccatacatct ctt 23

<210> SEQ ID NO 75
<211> LENGTH: 25
<212> TYPE: DNA
<213> ORGANISM: Artificial Sequence
<220> FEATURE:
<223> OTHER INFORMATION: Primer

<400> SEQUENCE: 75
tggtagacat aggtgtacac atacg 25

<210> SEQ ID NO 76
<211> LENGTH: 19
<212> TYPE: DNA
<213> ORGANISM: Artificial Sequence
<220> FEATURE:
<223> OTHER INFORMATION: Primer

<400> SEQUENCE: 76
attataaggc tttatttga 19

<210> SEQ ID NO 77
<211> LENGTH: 46
<212> TYPE: DNA
<213> ORGANISM: Artificial Sequence
<220> FEATURE:
<223> OTHER INFORMATION: Primer

<400> SEQUENCE: 77
ataagaaatt attcaataca gattagatat tagtcaacaa tgctgg 46

<210> SEQ ID NO 78
<211> LENGTH: 38
<212> TYPE: DNA
<213> ORGANISM: Artificial Sequence
<220> FEATURE:
<223> OTHER INFORMATION: Primer

<400> SEQUENCE: 78
tacgtttttg gtggtaaaaa cgatcataca cctcagtt 38

<210> SEQ ID NO 79
<211> LENGTH: 46
<212> TYPE: DNA
<213> ORGANISM: Artificial Sequence
<220> FEATURE:
<223> OTHER INFORMATION: Primer

<400> SEQUENCE: 79
gtaagaaatt attcaataca gattagatat tagtcaacaa tgctgg 46

<210> SEQ ID NO 80
<211> LENGTH: 38
<212> TYPE: DNA
<213> ORGANISM: Artificial Sequence
<220> FEATURE:
<223> OTHER INFORMATION: Primer

<400> SEQUENCE: 80
cacgtttttg gtggtaaaaa cgatcataca cctcagtt 38

<210> SEQ ID NO 81
<211> LENGTH: 26
<212> TYPE: DNA
<213> ORGANISM: Artificial Sequence
<220> FEATURE:
<223> OTHER INFORMATION: Primer

<400> SEQUENCE: 81
tacacgtttt tggtggtaat aactat 26

<210> SEQ ID NO 82
<211> LENGTH: 27
<212> TYPE: DNA
<213> ORGANISM: Artificial Sequence
<220> FEATURE:
<223> OTHER INFORMATION: Primer

<400> SEQUENCE: 82
tgtaagaaat tattcaatac agcactt 27

<210> SEQ ID NO 83
<211> LENGTH: 25
<212> TYPE: DNA
<213> ORGANISM: Artificial Sequence
<220> FEATURE:
<223> OTHER INFORMATION: Primer

<400> SEQUENCE: 83
atacgttttt ggtggtaata actat 25

<210> SEQ ID NO 84
<211> LENGTH: 26
<212> TYPE: DNA
<213> ORGANISM: Artificial Sequence
<220> FEATURE:
<223> OTHER INFORMATION: Primer

<400> SEQUENCE: 84
ataagaaatt attcaataca gcactt 26

<210> SEQ ID NO 85
<211> LENGTH: 20
<212> TYPE: DNA
<213> ORGANISM: Artificial Sequence
<220> FEATURE:
<223> OTHER INFORMATION: Primer

<400> SEQUENCE: 85
aactgaggtg tatgatcgtt 20

<210> SEQ ID NO 86
<211> LENGTH: 18
<212> TYPE: DNA
<213> ORGANISM: Artificial Sequence
<220> FEATURE:
<223> OTHER INFORMATION: Primer

<400> SEQUENCE: 86
acccatgctt tcatacga 18

<210> SEQ ID NO 87
<211> LENGTH: 21
<212> TYPE: DNA
<213> ORGANISM: Artificial Sequence
<220> FEATURE:
<223> OTHER INFORMATION: Primer

<400> SEQUENCE: 87
ttatttcttc taggtatatt t 21

<210> SEQ ID NO 88
<211> LENGTH: 17
<212> TYPE: DNA
<213> ORGANISM: Artificial Sequence
<220> FEATURE:
<223> OTHER INFORMATION: Primer

<400> SEQUENCE: 88
atgatggctc ttctatt 17

<210> SEQ ID NO 89
<211> LENGTH: 44

<212> TYPE: DNA
<213> ORGANISM: Artificial Sequence
<220> FEATURE:
<223> OTHER INFORMATION: Primer

<400> SEQUENCE: 89
ctaccatttg acgtaacact aagagatgta tggtatgttt caag 44

<210> SEQ ID NO 90
<211> LENGTH: 43
<212> TYPE: DNA
<213> ORGANISM: Artificial Sequence
<220> FEATURE:
<223> OTHER INFORMATION: Primer

<400> SEQUENCE: 90
gaatttattg tattggggga tcatatgctt ctacattcgg tat 43

<210> SEQ ID NO 91
<211> LENGTH: 44
<212> TYPE: DNA
<213> ORGANISM: Artificial Sequence
<220> FEATURE:
<223> OTHER INFORMATION: Primer

<400> SEQUENCE: 91
agaatttatt gtattggggg atcatatgct tctacattcg gtat 44

<210> SEQ ID NO 92
<211> LENGTH: 44
<212> TYPE: DNA
<213> ORGANISM: Artificial Sequence
<220> FEATURE:
<223> OTHER INFORMATION: Primer

<400> SEQUENCE: 92
gtaccatttg acgtaacact aagagatgta tggtatgttt caag 44

<210> SEQ ID NO 93
<211> LENGTH: 43
<212> TYPE: DNA
<213> ORGANISM: Artificial Sequence
<220> FEATURE:
<223> OTHER INFORMATION: Primer

<400> SEQUENCE: 93
caatttattg tattggggga tcatatgctt ctacattcgg tat 43

<210> SEQ ID NO 94
<211> LENGTH: 44
<212> TYPE: DNA
<213> ORGANISM: Artificial Sequence
<220> FEATURE:
<223> OTHER INFORMATION: Primer

<400> SEQUENCE: 94
acaatttatt gtattggggg atcatatgct tctacattcg gtat 44

<210> SEQ ID NO 95
<211> LENGTH: 25
<212> TYPE: DNA
<213> ORGANISM: Artificial Sequence
<220> FEATURE:
<223> OTHER INFORMATION: Primer

<400> SEQUENCE: 95
tagaatttat tgtattgggg gatat 25

<210> SEQ ID NO 96
<211> LENGTH: 26
<212> TYPE: DNA
<213> ORGANISM: Artificial Sequence
<220> FEATURE:
<223> OTHER INFORMATION: Primer

<400> SEQUENCE: 96
gtagaattta ttgtattggg ggatat 26

<210> SEQ ID NO 97
<211> LENGTH: 25
<212> TYPE: DNA
<213> ORGANISM: Artificial Sequence
<220> FEATURE:
<223> OTHER INFORMATION: Primer

<400> SEQUENCE: 97
tacaatttat tgtattgggg gatat 25

<210> SEQ ID NO 98
<211> LENGTH: 26
<212> TYPE: DNA
<213> ORGANISM: Artificial Sequence
<220> FEATURE:
<223> OTHER INFORMATION: Primer

<400> SEQUENCE: 98
gtacaattta ttgtattggg ggatat 26

<210> SEQ ID NO 99
<211> LENGTH: 22
<212> TYPE: DNA
<213> ORGANISM: Artificial Sequence
<220> FEATURE:
<223> OTHER INFORMATION: Primer

<400> SEQUENCE: 99
ctaccatttg acgtaacacc ac 22

<210> SEQ ID NO 100
<211> LENGTH: 23
<212> TYPE: DNA
<213> ORGANISM: Artificial Sequence
<220> FEATURE:
<223> OTHER INFORMATION: Primer

<400> SEQUENCE: 100
tctaccattt gacgtaacac cac 23

<210> SEQ ID NO 101
<211> LENGTH: 23
<212> TYPE: DNA
<213> ORGANISM: Artificial Sequence
<220> FEATURE:
<223> OTHER INFORMATION: Primer

<400> SEQUENCE: 101
tgtaccattt gacgtaacac cac 23

<210> SEQ ID NO 102
<211> LENGTH: 42
<212> TYPE: DNA
<213> ORGANISM: Artificial Sequence -continued

```
<220> FEATURE:
<223> OTHER INFORMATION: Primer

<400> SEQUENCE: 102

ctaccatttg acgtaactaa gagatgtatg gtatgtttca ag                    42
```

POLYMORPHISM (SNP) USING LAMP AND BLOCKING PRIMERS

RELATED APPLICATIONS

The present application is a National Phase entry of PCT Application No. PCT/EP2019/065046, filed Jun. 7, 2019, which claims priority from Great Britain Application No. 1809449.0 filed Jun. 8, 2018, all of these disclosures being hereby incorporated by reference in their entirety.

TECHNICAL FIELD

The present application relates to methods for detecting a first allele of a single nucleotide polymorphism (SNP) in a nucleic acid sequence under isothermal conditions using primers.

BACKGROUND OF THE INVENTION

The emergence of drug resistance is a constant threat to global public health limiting the ability to treat infectious diseases effectively and compromising medical procedures. Rapid detection of single nucleotide polymorphisms (SNPs) that are linked with resistance phenotypes in infectious pathogens is, therefore, key to improving treatment efficacy and guiding clinical usage of drugs towards development of personalized medicine. However, the detection of genetic markers is still a major challenge for molecular-based diagnostic technologies, especially for those aiming to be deployed at point-of-care (PoC).

Currently, high-throughput methods such as Next Generation Sequencing or Sanger sequencing are considered the gold standard for low frequency allele detection. Despite their advancement in the last decade, their high cost and time to report results limits their use outside specialized laboratories. A variety of PCR-based methods have been developed to enhance detection of genetic markers. These allele-specific PCR (AS-PCR) techniques can be classified into two main groups: major allele suppression methods and minor allele enrichment methods. Within the first group, competitive blocking primers have been designed to suppress the amplification of the major allele, enabling minor allele amplification by allele-specific primers. Different approaches have been reported such as (i) PCR blocking primers with a poly-A tail of 4 nucleotides (Wu et al. *Nat. Biomed. Eng.* 1, 714-723 (2017)) or with 3'-end modifications (ddNTPs, carbon-spacer, or inverted DNA nucleotides (Dobosy et al *BMC Biotechnol.* 11, 80 (2011); Orou et al. *Hum. Mutat.* 6, 163-169 (1995); Vestheim et al. *Front. Zool.* 5, 12 (2008): Wang et al. *J. Mol. Diagnostics* 15, 62-69 (2013)), (ii) PCR clamping (Vestheim et al. *Front. Zool.* 5, 12 (2008)) based on the incorporation of peptide nucleic acids (Chiou et al. *Nat. Protoc.* 1, 2604-2612 (2007)), bridged nucleic acids (Sekiguchi et al. *Nucleosides. Nucleotides Nucleic Acids* 24, 1097-100 (2005)) or locked nucleic acids (Morandi et al. *PLOS One* 7, e36084 (2012)), and (iii) PCR amplification of previously treated dsDNA with lambda exonuclease (Wu et al. *Nucleic Acids Res.* 46, e24-e24 (2018)). Within the second group, AS-PCR techniques have focused on enhancing the amplification of the minor allele (Ugozzoli & Wallace *Methods* 2, 42-48 (1991)) by the incorporation of (i) primers specific to the SNP at their 3'-end (Wang et al. *Biotechniques* 39, 885-893 (2005)) (ii) primers with mismatches within the 4 bases from the 3'-end (Stadhouders et al. *J. Mol. Diagnostics* 12, 109-117 (2010); Kwok et al. *Nucleic Acids Res.* 18, 999-1005 (1990): Ayyadevara et al. *Anal. Biochem.* 284, 11-18 (2000)), (iii) primers of different lengths for $T_m$ analysis (Chen et al. *PLOS One* 11, e0153593 (2016)). However, the need of thermal cycling, electrophoresis and/or modified oligonucleotides for validation elevates the time and cost per sample preventing these PCR-based methods from being widespread to decentralized areas.

An alternative to PCR is isothermal DNA amplification techniques, which offer nucleic acid synthesis at constant temperature using simpler and less complex equipment better suited to applications at PoC. Several isothermal techniques have been reported, each one with its own innovative characteristics and temperature requirements in the range of 30-65° C., depending on the enzyme used in the reaction. The most popular techniques are: (i) recombinase polymerase amplification, (ii) nucleic acid sequence-based amplification, (iii) loop-mediated isothermal amplification (LAMP) and (iv) helicase-dependent amplification. Among them, LAMP has become popular due to advantages such as its high efficiency, high amplification yield, high specificity due to four to six primers in the reaction, strand displacement DNA synthesis between 60-65° C., and the capability of visual detection of products due to precipitation of magnesium pyrophosphate. Allele-specific LAMP (AS-LAMP), has been previously described for minor allele amplification. Several approaches have been reported such as (i) placing the SNP at the 5'-end of overlapped FIP and BIP primers (Zhang et al. *Sci. Rep.* 6, 26533 (2016)) (ii) placing the SNP at the 3'-end of B2 or LB primer (Badolo et al. *Malar. J.* 11, 227 (2012)), or (iii) introducing additional mismatches (Wang *Biotechnol. Biotechnol. Equip.* 30, 314-318 (2016); Duan et al. *Sci. Rep.* 5, 17278 (2015)). Although these methods either delay the onset of the unspecific reaction or only amplify the desired target, each design is unique and dependent on the target, preventing their standardization across other relevant SNPs. The addition of universal QProbe (Ayukawa et al. *Sci. Rep.* 7, 4253 (2017)) or the utilization of the Taq Mut enzyme (Lezhava, A. & Hayashizaki, Y. in 437-451 (2009). doi: 10.1007/978-1-60327-411-1_28) have addressed this to an extent, however, the need of melting analysis or low specificity prevent the use of these methods at the PoC.

SUMMARY OF THE INVENTION

Described herein is a new method for enhanced SNP detection at isothermal conditions. In a specific embodiment the method is based on (i) SNP-based loop-mediated isothermal amplification (sbLAMP) primers, which consist of six primers targeting eight different regions, with two of them responsible for AS-LAMP amplification, and (ii) the novel unmodified self-stabilizing (USS) primers, which consist of one forward blocking primer (FB) and one backward blocking primer (BB) complementary to the SNP at their 5' end, which are responsible for preventing unspecific sbLAMP amplification. Also described herein are universal primer design guidelines.

The inventors have also demonstrated successful application of the method of the invention defining universal primer design guidelines based on the detection of the SNP C580Y located in the gene kelch 13 (K13) of the AT-rich genome of *P. falciparum* responsible for resistance to artemisinin-based drug treatment of malaria. As validation, the same principles were used to develop USS-sbLAMP primers for detection of another antimalarial-resistant K13 SNP, Y493H. The general methodology achieves high sensitivity, efficiency, specificity and rapid time to positive (<35 min) for SNP detection and is also applicable to mixed infections. The broad principles of primer design described herein allow for the design of other USS-sbLAMP primer sets for the detection of other relevant targets. Diagnostic tests incorporating the proposed isothermal chemistry will greatly expand the capability of rapid SNP screening, including in limited-resource settings (LRS) where rapid, sensitive and specific diagnostics of infectious diseases are of vital importance.

According to a first aspect, the invention provides a method for detecting a first allele of a SNP in a nucleic acid sequence.

According to a second aspect, the invention provides a method for detecting drug resistance in an organism comprising detecting a first allele of a SNP in a nucleic acid sequence.

According to a third aspect, the invention provides a method for the diagnosis of an infectious disease or a drug resistant infection comprising detecting a first allele of a SNP in a nucleic acid sequence.

According to a fourth aspect, the invention provides a method for the treatment of an infectious disease or a drug resistant infection in a subject in need thereof comprising detecting a first allele of a SNP in a nucleic acid sequence.

According to a fifth aspect, the invention provides a kit comprising primers used in the first to the fourth aspects of the invention.

According to a sixth aspect, the invention provides a reaction mixture comprising the components of the kit according to the fifth aspect of the invention in a liquid medium.

USS primers may be formed from DNA, RNA, peptide nucleic acid (PNA), Morpholino and locked nucleic acid (LNA), glycol nucleic acid (GNA), threose nucleic acid (TNA) or any synthetic nucleic acid analogue.

The above summary is not intended to describe each illustrated embodiment or every implementation of the subject matter hereof. The figures and the detailed description that follow more particularly exemplify various embodiments.

SEQUENCE LISTING

The Sequence Listing is submitted as an ΔSCII text file in the form of the file named "SequenceListing.txt.", (~18.100 bytes) which was created on Dec. 8, 2020, which is incorporated by reference herein.

BRIEF DESCRIPTION OF THE DRAWINGS

Subject matter hereof may be more completely understood in consideration of the following detailed description of various embodiments in connection with the accompanying figures, in which:

FIG. 6 illustrates experimental configurations using the Lab-on-Chip platform. Schematic (A) illustrates a setup showing the Lab-on-Chip (LoC) platform including a motherboard PCB that facilitates data readout, a cartridge PCB hosing the microchip and microfluidic chamber, the microchip including an array of 4096 ISFET sensors and an external thermal controller. Furthermore, a microphotograph shows a 6×6 subset of the ISFET array. Schematic (B) shows a cross-section of an ISFET fabricated in unmodified CMOS technology and equivalent circuit macromodel. Schematic (C) is a schematic of a pixel configuration implemented as a source follower configuration where changes in Vout reflect changes in pH [37]. Schematic (D) is a cross-section illustration of the LoC platform showing the reaction interface. Amplification at 63° C. only occurs if the specific target is present in the loaded sample. Results are displayed in real-time.

DETAILED DESCRIPTION OF THE INVENTION

Figure 1:
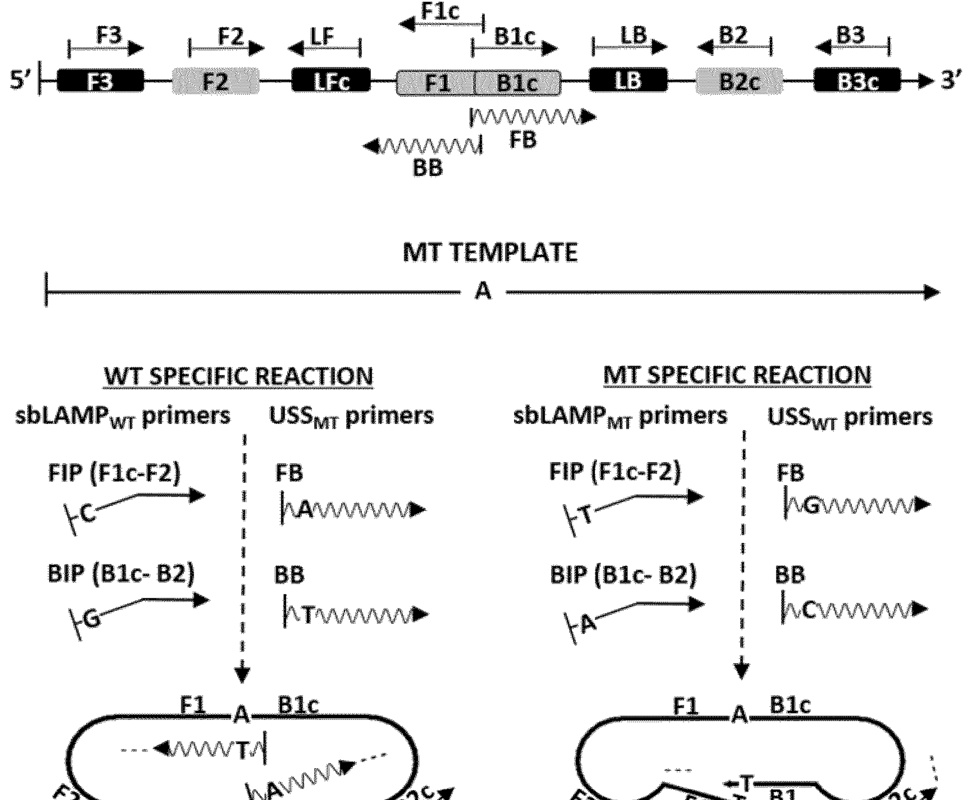
FIG. 1 illustrates a theoretical mechanism of USS-sbLAMP allele-specific amplification in the presence of MT template. As an example, MT template presents allele A and it is uniquely amplified within the MT specific reaction ($sbLAMP_{MT}$ and $USS_{WT}$ primers). Amplification of the MT template within the WT specific reaction ($sbLAMP_{WT}$ and $USS_{MT}$ primers) is prevented by the annealing of complementary $USS_{MT}$ primers.

According to a first aspect, the invention provides a method for detecting a first allele of a single nucleotide polymorphism (SNP) in a nucleic acid sequence, wherein the method comprises

- (a) amplifying under isothermal conditions and stringent conditions a nucleic acid sequence from a sample, in a reaction mixture comprising
  - (i) the nucleic acid sequence,
  - (ii) a nucleic acid polymerase,
  - (iii) a nucleoside triphosphate mixture,
  - (iv) a forward inner primer targeting the first allele (FIPa1), comprising a F1c region which anneals to a F1 region of the nucleic acid sequence in the presence of the first allele and a F2 region which anneals to a F2c region of the nucleic acid sequence,
  - (v) a backward inner primer targeting the first allele (BIPa1), comprising a B1c region which anneals to a B1 region of the nucleic acid sequence in the presence of the first allele and a B2 region which anneals to a B2c region of the nucleic acid sequence,
  - (vi) a forward blocking primer targeting a second allele of the SNP (FBa2), comprising a B1c region which anneals to a B1 region of the nucleic acid sequence in the presence of the second allele, and
  - (vii) a backward blocking primer targeting the second allele (BBa2), comprising a F1c region which anneals to a F1 region of the nucleic acid sequence in the presence of the second allele, wherein the F1 region of the nucleic acid sequence and the B1 region of the nucleic acid sequence both contain the SNP, and
- (b) detecting an amplified nucleic acid sequence, wherein the detection of an amplified nucleic acid sequence indicates the presence the first allele of the SNP.

Nucleic acid amplification occurs under isothermal conditions. Accordingly, the method may also comprise a step of holding the reaction mixture under isothermal conditions. The isothermal conditions may be any suitable conditions for DNA amplification without the need for cycling between different temperatures for different steps in the amplification reaction, in contrast to traditional polymerase chain reaction (PCR). Isothermal conditions may be maintained using a laboratory water bath or heat block. The temperature selected may be from 30 to 95° C. The temperature may be 50 to 70° C. The temperature may be around 50, 51, 52, 53, 54, 55, 56, 57, 58, 59, 60, 61, 62, 63, 64, 65, 66, 67, 68, 69 or 70° C. The temperature may be 60 to 65° C. For example, the temperature may be around 63° C.

The duration of the amplifying step may be around 1 to 150 minutes. The duration of the amplifying step may be around 5 to 60 minutes. The duration of the amplifying step may be around 20 to 40 minutes. The duration of the amplifying step may be around 20, 21, 22, 23, 24, 25, 26, 27, 28, 29, 30, 31, 32, 33, 34, 35, 36, 37, 38, 39 or 40 minutes. For example, the amplification step may be around 30 minutes. The amplification step may be at least around 30 minutes.

Any duration of the amplification step as defined above may be combined with any reaction temperature as defined above as long as the reaction conditions allow for amplification and an amplification product can be detected. The temperature and duration may be optimized by comparison with a positive and/or a negative control. For example, a reaction temperature and duration may be selected to allow for detectable amplification of product in a positive control and/or with the nucleic acid from the sample but not to allow for detectable amplification in another sample and/or a negative control.

The amplifying may comprise an annealing step and an extension step. Accordingly, the amplifying may comprise annealing FIP and BIP to the nucleic acid sequence and extending FIP and BIP to produce an amplified nucleic acid sequence. The amplifying may comprise an initiation phase comprising the annealing step and the extension step. The initiation phase may comprise the F2 region of FIP annealing to the F2c region of the nucleic acid sequence and the B2 region of BIP annealing to the B2c region of the nucleic acid sequence. The amplifying may also comprise annealing additional primers to the nucleic acid sequence as further described below.

The amplifying may be loop mediated isothermal amplification (LAMP). Since the method relates to a modified LAMP assay that detects an allele of a SNP, the method may be described as "SNP based LAMP" or sbLAMP.

When the amplifying is LAMP, the temperature may be 50 to 70° C. When the amplifying is LAMP, the temperature may be 60 to 65° C.

When the amplifying is LAMP, the amplifying step may be around 5 to 60 minutes.

When the nucleic acid sequence is RNA or cDNA, the amplifying may be reverse transcription loop mediated isothermal amplification (RT-LAMP). Since the method relates to a modified LAMP assay that detects an allele of a SNP, when the amplifying is RT-LAMP, the method may be described as "SNP based RT-LAMP" or sbRT-LAMP.

Detecting may be by any suitable means. For example, amplification products may be detected by measuring turbidity, by using pH-sensitive dyes, using nucleic acid intercalating agents and by using metal indicators. The reaction mixture may comprise a detection agent. The detection agent may be a pH-sensitive dye, or a metal indicator or a nucleic acid intercalating agent.

Detecting may be colorimetric detection. Colorimetric detection may be by the naked eye, or by use of a cell phone. Detecting may be colorimetric detection compatible with the naked eye or a cell phone. The cell phone may detect amplification using a camera and/or an app. The app may be an app designed for use with the method of the invention. The app may be supplied by a third party. The app may be software supplied with the cell phone. The app may be an image processing app. A phone or other suitable camera device may capture an image for detection. The image may then be processed on another device or on the same device.

Detecting may be pH-based detection. For example, the reaction mixture may comprise a pH-sensitive indicator, such as a dye. The pH sensitive indicator may be a phenol red pH indicator. The phenol red pH indicator may allow visual detection of the accumulation of protons during the amplification reaction, providing a change in solution color from pink (negative) to yellow (positive).

Detecting may be by one or more ion sensors. For example, the detecting may be by one or more semiconductor-based ion sensors. Detection using semiconductor-based ion sensors may be particularly advantageous at the point-of-care. The use of ion sensors, in particular semiconductor-based ion sensors for example the ion-sensitive field-effect transistor (ISFET), provide a cheap and easy-to-use diagnostic platform for chemical sensing which is suitable for point-of-care applications. The ion-sensitive field-effect transistor (ISFET) is a chemically sensitive transistor. An IFSET can be used to measure ion concentrations in solution. An array of such sensors can create a platform for chemical sensing. The detecting may therefore be performed in accordance with a method of UK application no. 1809420.1 or International application no. PCT/GB2019/051597, which are hereby incorporated by reference in their entirety.

Detecting may be by one or more complementary metal-oxide-semiconductor (CMOS) based ion sensors. The detecting may therefore be by a CMOS based detection system. CMOS based detection systems employ label free amplification-coupled detection methods for measuring released hydrogen ions during nucleotide incorporation rather than relying on indirect measurements such as fluorescent dyes. CMOS technology therefore reduces the cost of the assay and size/price of instrumentation as there is no need for bulky equipment. Also, CMOS technology integrates thousands of sensors per microchips, enabling machine learning and analytical methods to reduce time-to-positive reaction, increasing sensitivity/specificity and enhancing quantification. These effects may be achieved in combination with a method of UK application no. 1809418.5 or International application no. PCT/EP2019/065039, which are hereby incorporated by reference in their entirety.

Detecting may therefore be a method for detecting an amplification reaction in a biological sample using an array of ion sensors, the amplification reaction being indicative of the presence of a first allele of a SNP, and/or the presence of a second allele of a SNP. The method may comprise monitoring a signal from each respective sensor of the array of ion sensors. The method may further comprise detecting a change in the signal from a first sensor of the array of ion sensors. The method may further comprise comparing the signal from the first sensor with the signal of at least one neighboring sensor, the neighboring sensor being adjacent to the first sensor in the array. Even further, the method may comprise determining, based on the comparing, that an amplification event has occurred in the vicinity of the first sensor.

Detecting may be detecting using a nucleic acid intercalating agent. The nucleic acid intercalating agent may be a fluorescent intercalating agent. The fluorescent intercalating agent may, for example, be a cyanine dye such as SYBR® Green (IUPAC ID: N',N'-dimethyl-N-[4-[(E)-(3-methyl-1,3-benzothiazol-2-ylidene)methyl]-1-phenylquinolin-1-ium-2-yl]-N-propylpropane-1,3-diamine), EvaGreen® (CAS number: 913830-62-3), SYTO™-9 (CBN number: CB6328526), SYTO™-13 (CAS number: 173080-69-8), SYTO™-82 and SYBR® Gold (CAS number: 163795-75-3).

Detecting may be detecting using a metal indicator. The metal indicator may, for example, be hydroxynaphthol blue, eriochrome black t, calmagite, curcumin, fast sulphon black, hematoxylin, murexide or xylenon orange.

Detecting may be performed in real time or at an end-point. Detecting in real time may be for example by using the LC96 System (LightCycler® 96 System, Roche, Switzerland). End-point detection may be, for example by using an end-point PCR machine, such as the Veriti™ Dx 96-well Fast Thermal Cycler (Thermo Fisher Scientific, USA), following by the colorimetric or fluorescent detection.

Detecting may be performed with reference to or by comparison with one or more controls. The control may be a positive and/or a negative control. Detecting may be performed with reference to or by comparison with a positive and/or a negative control. No amplification may be detected in the negative control. Amplification may be detected in the positive control. In the presence of a positive and/or negative control, the reaction mixture may be referred to as the test reaction mixture. Detecting may be performed by the finding of a significant difference in amplification compared to a positive and/or a negative control. The significant difference in amplification may be a significant difference in the time taken for an amplification product to be detected. Alternatively, the significant difference in amplification may be a significant difference in the time taken for a threshold level of an amplification product to be detected. The threshold level may be any suitable threshold level to permit a finding of a significant difference in amplification. The significant difference in amplification may be a significant difference in color of the reaction mixture after a defined time.

The negative control may use a reaction mixture corresponding to the test reaction mixture except for the absence of the nucleic acid sequence. Alternatively, the negative control may use a reaction mixture corresponding to the test reaction mixture except the nucleic acid sequence is replaced with a different nucleic acid sequence known not to be amplified by the primers in the reaction mixture; in this situation, the nucleic acid sequence in the test reaction mixture may be termed the test nucleic acid sequence and the nucleic acid sequence in the negative control reaction mixture may be termed the negative control nucleic acid sequence.

The positive control may use a reaction mixture corresponding to the test reaction mixture except the nucleic acid sequence is replaced with a different nucleic acid sequence known to be amplified by the primers in the reaction mixture: in this situation, the nucleic acid sequence in the test reaction mixture may be termed the test nucleic acid sequence and the nucleic acid sequence in the positive control reaction mixture may be termed the positive control nucleic acid sequence. The positive control nucleic acid sequence may for example be a chemically synthesized nucleic acid sequence comprising the SNP.

In an alternative definition, the detection step may not involve the detection of an amplified nucleic acid sequence which indicates the presence the SNP. Accordingly, step (b) of the method above may alternatively be stated as:

(b) detecting an amplified nucleic acid sequence.

The nucleic acid sequence may be DNA or RNA. When the nucleic acid sequence is DNA, the nucleic acid polymerase is a DNA polymerase. For example, the DNA polymerase may be Bst polymerase, Bst 2.0 DNA Polymerase, Bst 3.0 DNA Polymerase or Large fragment Bst DNA polymerase. Accordingly, when the nucleic acid polymerase is a DNA polymerase, the nucleoside triphosphate mixture comprises dNTPs. dNTPs comprise dATP, dGTP, dCTP, and dTTP.

When the nucleic acid sequence is RNA the method may also comprise reverse transcription of the RNA to produce cDNA, for example by addition of a reverse transcriptase such as AMV Reverse Transcriptase. The nucleic acid sequence may therefore also be cDNA. When the nucleic acid is cDNA, the nucleic acid polymerase is a DNA polymerase and the nucleoside triphosphate mixture comprises dNTPs.

The reaction mixture may be any suitable medium in which amplification of a nucleic acid may take place. The reaction mixture may comprise deionized water. The reaction medium may comprise isothermal buffer, $MgSO_4$, BSA, Betaine and/or Syto9. The reaction mixture may be of any suitable volume.

The reaction mixture may be in a vessel. The vessel may be referred to as a reaction vessel. The vessel may be any suitable container. The vessel may be open topped. For example, the vessel may be a test tube or a plate, such as a 96-well plate. The vessel may be closed, for example by the addition of a lid. The lid may be integral or separate. For example, the vessel may be a microcentrifuge tube such as an Eppendorf tube. The vessel may be of any suitable volume.

The optimal volume of reaction mixture may be determined by the skilled person, accounting for example for the size of the vessel. For instance, when the vessel is a 96-well plate the reaction volume may be from 5 to 50 μL. For example, the reaction volume may be 5 μL.

The method of the invention may be performed in a number of repeats. For example, the method may be performed in duplicate or triplicate.

As used herein, "stringent conditions" are known to those skilled in the art and can be found in Current Protocols in Molecular Biology, John Wiley & Sons, N.Y., 6.3.1-6.3.6, 1991. The stringent conditions may be stringent conditions for hybridization. The stringent conditions may be stringent conditions for annealing. Stringent conditions may be defined as equivalent to annealing in isothermal buffer. Isothermal buffer (1×) may comprise 20 mM Tris-HCl: 10 mM $(NH_4)_2SO_4$: 50 mM KCl: 8 mM $MgSO_4$: Betaine 0.8M: 0.1% Tween® 20; and may have pH 8.8 at 25° C.

As used herein, "nucleic acid sequence" may refer to either a double stranded or to a single stranded nucleic acid molecule. The nucleic acid sequence may therefore alternatively be defined as a nucleic acid molecule. The nucleic acid molecule comprises two or more nucleotides. The nucleic acid sequence may be synthetic. The nucleic acid sequence may refer to a nucleic acid sequence that was present in the sample on collection. Alternatively, the nucleic acid sequence may be an amplified nucleic acid sequence or an intermediate in the amplification of a nucleic acid sequence, such as a dumbbell shaped intermediate or a stem-loop intermediate, which are described further below. In particular, without being bound by theory, it is thought that the forward and backward blocking primers function by annealing to the nucleic acid sequence that would otherwise form the dumbbell shaped intermediate. The forward and backward blocking primers may function by preventing the formation of the dumbbell shaped intermediate or preventing the formation of the stem-loop intermediate which implies the closing of the dumbbell structure, the elongation through 3' and the annealing of FIP and/or BIP. Therefore, where, for example, FBa2 is defined as "comprising a B1c region which anneals to a B1 region of the nucleic acid sequence in the presence of the second allele" the B1 region to which FBa2 anneals may be a B1 region of the dumbbell shaped intermediate. Likewise, where BBa2 is defined as "comprising a F1c region which anneals to a F1 region of the nucleic acid sequence in the presence of the second allele", the F1 region to which BBa1 anneals may be a F1 region of the dumbbell shaped intermediate.

As used herein, "anneal", "annealing", "hybridize" and "hybridizing" refer to complementary sequences of single-stranded regions of a nucleic acid pairing via hydrogen bonds to form a double-stranded polynucleotide. As used herein, "anneal", "anneals", "hybridize" and "hybridizes" may refer to an active step. Alternatively, as used herein, "anneal", "anneals", "hybridize" and "hybridizes" may refer to a capacity to anneal or hybridize: for example, that a primer is configured to anneal or hybridize and/or that the primer is complementary to a target. Accordingly, for example, a reference to a primer or a region of a primer which anneals to a nucleic acid sequence or a region of a nucleic acid sequence may in a method of the invention mean either that the annealing is a required step of the method: that the primer or region of the primer is complementary to the nucleic acid sequence or region of the nucleic acid sequence: or that the primer or region of the primer is configured to anneal to the nucleic acid sequence or region of the nucleic acid sequence.

As used herein, the term "energetically favorable" refers generally to the amount of free energy (G) released by a reaction, process or event. Energetically favorable reactions, for example, are those that release a large quantity of free energy, or in other words may have a negative Gibbs free energy (AG). AG in general terms measures the amount of disorder created in the universe when a reaction, process or event takes place. Energetically favorable reactions, processes or events have a strong tendency to occur spontaneously. However, for example, the reaction rate of an energetically favorable reaction will depend on other factors, such as the availability of enzymes. In contrast, energetically unfavorable reactions, processes or events may have a positive AG or might be termed unfavorable with respect to another reaction that is more energetically favored meaning the AG of the unfavorable reaction is higher (negative but closer to zero, or above zero). Accordingly, energetically unfavorable reactions, for example, may not occur spontaneously, and may require coupling to a second reaction with a negative AG sufficiently large to offset the positive AG of the energetically favorable reaction to the extent that the total AG of the two coupled reactions is negative.

The term "primer" as used herein refers to a nucleic acid, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e. in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, depending on the complexity of the target sequence, the nucleic acid primer typically contains 15 to 25 or more nucleotides, although it may contain fewer or more nucleotides. According to the present invention a nucleic acid primer typically contains 13 to 30 or more nucleotides.

Two primers that anneal to opposite strands of a template nucleic acid molecule and may each initiate synthesis of the nucleic acid sequence between their two target sites may be referred to as a primer set. FIP and BIP may be referred to as a primer set since they may initiate synthesis of the nucleic acid sequence between F1/F1c and B1/B1c.

Since DNA synthesis occurs in the 5' to 3' direction, the 3' ends of a primer set generally point towards each other, when they are annealed to their template nucleic acid strand, and the primers anneal on opposite strands of the template nucleic acid strand. For example, the forward blocking primer may anneal to the template (−) strand and is identical to (a part of) the template (+) strand. Likewise, the backward blocking primer may anneal to the template (+) strand and is identical to (a part of) the template (−) strand. Forward, reverse (backward), (+) and (−) refer to transcription of genes: the (+) DNA strand has the same orientation as a messenger RNA, transcribed from the DNA. Alternatively stated, the forward orientation is pointing towards the end of a gene. However, the 3' ends of FIP and BIP point in opposite directions.

FIPa1 may comprise a F1c region and a F2 region. The FIPa1 may consist of a F1c region and a F2 region. The F2 region may be displaced in the 3' direction with respect to the F1c region of FIPa1. The F1c region of FIPa1 may comprise a nucleic acid that is complementary to the first allele of the SNP. The F1c region may be complementary to a target region comprising the SNP. The target region comprising the SNP may therefore be referred to as F1.

The F2 region of FIPa1 is not complementary to the target region comprising the SNP. Accordingly, the F2 region of FIPa1 will not anneal to the target region comprising the SNP under stringent conditions. Rather, the F2 region of FIPa1 comprises a sequence that is the reverse complement of an F2c region of the nucleic acid. The F2c region of the nucleic acid is displaced from the F1c region of the nucleic acid in the 3' direction. The F2 region of FIPa1 will therefore anneal to the F2c region of the nucleic acid under stringent conditions.

BIPa1 may comprise a B1c region and a B2 region. The BIPa1 may consist of an B1c region and an B2 region. The B2 region may be displaced in the 3' direction with respect to the B1c region of BIPa1. The B1c region of BIPa1 may comprise a nucleic acid that is complementary to the first allele of the SNP. The B1c region may be complementary to a target region comprising the SNP. The target region comprising the SNP may therefore be referred to as B1.

The B2 region of BIPa1 is not complementary to the target region comprising the SNP. Accordingly, the B2 region of BIPa1 will not anneal to the target region comprising the SNP under stringent conditions. Rather, the B2 region of BIPa1 comprises a sequence that is the reverse complement of an B2c region of the nucleic acid. The B2c region of the nucleic acid is displaced from the B1c region of the nucleic acid in the 3' direction. The B1c region of BIPa1 will therefore anneal to the B1 region of the nucleic acid under stringent conditions.

FBa2 and BBa2 are described as "blocking" primers since they block amplification in the presence of the second allele of the SNP. FBa2 is referred to as the "forward" blocking primer because its orientation in the 5' to 3' direction is the same as that of the template (+) strand. Reciprocally, BBa2 is referred to as the "backward" blocking primer because its orientation is the same as that of the template (−) strand.

FBa2 and BBa2 may also be described as "competitive blocking" primers since they compete with other primers and/or complementary regions of the nucleic acid sequence to block amplification in the presence of the second allele of the SNP. FBa2 may thus be referred to as the "forward" competitive blocking primer because its orientation in the 5' to 3' direction is the same as that of the template (+) strand. Reciprocally, BBa2 may be referred to as the "backward" competitive blocking primer because its orientation is the same as that of the template (−) strand.

FBa2 comprises a B1c region which anneals to a B1 region of the nucleic acid sequence in the presence of the second allele. Specifically, the B1c region of FBa2 may anneal to a B1 region of the nucleic acid sequence of the dumbbell shaped intermediate, thereby preventing the formation of the dumbbell shaped secondary structure in the presence of the second allele. The B1c region of FBa2 is therefore complementary to the B1 region of the nucleic acid sequence. The B1 region of the nucleic acid sequence comprises the SNP. The B1c region of FBa2 may be complementary to a target region comprising the SNP. The B1c region of FBa2 therefore comprises a nucleotide corresponding to the second allele of the SNP. Typically, the sequence of the B1c region of FBa2 is 100% complementary to the sequence of the B1 region of the nucleic acid sequence in the presence of the second allele. In other words, the sequence of the B1c region of FBa2 is typically identical to the sequence of the B1 region of the nucleic acid sequence in the presence of the second allele. FBa2 may therefore be described as an "unmodified" primer. Without being bound by theory, the 100% complementarity between the sequence of B1c region of FBa2 and the sequence of the B1 region of the nucleic acid sequence contributes to the ability of FBa2 to anneal to the nucleic acid sequence in the presence of the second allele.

Since FBa2 contains a nucleotide that is complementary to the second allele of the SNP, it does not contain a nucleotide that is complementary to the first allele of the SNP. Accordingly, without being bound by theory, it will be more energetically favorable for FBa2 to anneal to the nucleic acid sequence in the presence of the second allele of the SNP than in the presence of the first allele of the SNP. Stated another way, the AG of FBa2 annealing to the nucleic acid in the presence of the second allele of the SNP may be less than the AG of FBa2 annealing to the nucleic acid in the presence of the first allele of the SNP.

BBa2 comprises a F1c region which anneals to a F1 region of the nucleic acid sequence in the presence of the second allele. Specifically, the F1c region of BBa2 may anneal to a F1 region of the nucleic acid sequence of the dumbbell shaped intermediate, thereby preventing the formation of the dumbbell shaped secondary structure in the presence of the second allele. The F1c region of BBa2 is therefore complementary to the F1 region of the nucleic acid sequence. The F1 region of the nucleic acid sequence comprises the SNP. The F1c region of BBa2 may be complementary to a target region comprising the SNP. The F1c region of BBa2 therefore comprises a nucleotide corresponding to the second allele of the SNP. Typically, the sequence of the F1c region of BBa2 is 100% complementary to the sequence of the F1 region of the nucleic acid sequence in the presence of the second allele. In other words, the sequence of the F1c region of BBa2 is typically identical to the sequence of the F1 region of the nucleic acid sequence in the presence of the second allele. BBa2 may therefore be described as an "unmodified" primer. Without being bound by theory, the 100% complementarity between the sequence of F1c region of BBa2 and the sequence of the F1 region of the nucleic acid sequence contributes to the ability of BBa2 to anneal to the nucleic acid sequence in the presence of the second allele.

Since BBa2 contains a nucleotide that is complementary to the second allele of the SNP, it does not contain a nucleotide that is complementary to the first allele of the SNP. Accordingly, without being bound by theory, it will be more energetically favorable for BBa2 to anneal to the nucleic acid sequence in the presence of the second allele of the SNP than in the presence of the first allele of the SNP. Stated another way, the AG of BBa2 annealing to the nucleic acid in the presence of the second allele of the SNP may be less than the AG of BBa2 annealing to the nucleic acid in the presence of the first allele of the SNP.

The F1 region of the nucleic acid sequence and the B1 region of the nucleic acid sequence both contain the SNP. The F1 region and the B1 region of the nucleic acid sequence may therefore be described as overlapping at the SNP. Accordingly, the F1c region of FIPa1 and the B1c region of FIPa1 both contain the SNP and/or overlap at the SNP. Similarly, the F1c region of BBa2 and the B1c region of FBa2 both contain the SNP and/or overlap at the SNP.

The amplification may comprise formation of a "dumbbell shape" intermediate. The dumbbell shape intermediate is a nucleic acid sequence. The dumbbell shape intermediate may be a single nucleic acid molecule. The term "dumbbell shape" refers to a possible secondary structure of the intermediate. The single nucleic acid molecule may comprise one or more stem-loop structures.

The dumbbell shape intermediate may comprise, in the 5' to 3' direction a B1c region, a B2 region, a LBc region, a B1 region, a F1c region, a LF region, a F2c region and a F1 region. Since the B1c region and B1 region are complementary they may form a stem-loop structure, wherein the B1c and B1 regions anneal to form the stem and the B2 and LBc regions form the loop. The B2 and LBc regions forming the loop are single stranded. Likewise, Since the F1c region and F1 region are complementary they may form a stem-loop structure, wherein the F1c and F1 regions anneal to form the stem and the F2c and LF regions form the loop. The F2c and LF regions forming the loop are single stranded.

Similarly, the dumbbell shape intermediate may comprise, in the 5' to 3' direction a F1c region, a F2 region, a LFc region, a F1 region, a B1c region, a LB region, a B2c region and a B1 region. Since the B1c region and B1 region are complementary they may form a stem-loop structure, wherein the B1c and B1 regions anneal to form the stem and the B2c and LB regions form the loop. The B2c and LB regions forming the loop are single stranded. Likewise, Since the F1c region and F1 region are complementary they may form a stem-loop structure, wherein the F1c and F1 regions anneal to form the stem and the F2 and LFc regions form the loop. The F2 and LFc regions forming the loop are single stranded.

The amplification may further comprise formation of a stem-loop intermediate. The stem-loop intermediate is a nucleic acid sequence. The stem-loop intermediate may be a single nucleic acid molecule. The term "stem-loop" refers to a possible secondary structure of the intermediate. The single nucleic acid molecule may comprise one or more stem-loop structures.

The stem-loop intermediate may comprise, in the 5' to 3' direction a B1c region, a B2 region, a LBc region, a B1 region, a F1c region, a LF region, a F2c region and a F1 region. Since the F1c region and F1 region are complementary they may form a stem-loop structure, wherein the F1c and F1 regions anneal to form part of the stem and the F2c and LF regions forms the loop. The F2c and LF regions forming the loop are single stranded. Since the B1c region and B1 region are complementary they may form a stem-loop structure, wherein the B1c and B1 regions anneal to form part of the stem and the B2 and LBc regions forms the loop. The B2 and LBc regions forming the loop are single stranded.

Similarly, the stem-loop intermediate may comprise, in the 5' to 3' direction a F1c region, a F2 region, a LFc region, a F1 region, a B1c region, a LB region, a B2c region and a B1 region. Since the B1c region and B1 region are complementary they may form a stem-loop structure, wherein the B1c and B1 regions anneal to form part of the stem and the B2c and LB regions forms the loop. The B2c and LB regions forming the loop are single stranded. Since the F1c region and F1 region are complementary they may form a stem-loop structure, wherein the F1c and F1 regions anneal to form part of the stem and the F2 and LFc regions forms the loop. The F2 and LFc regions forming the loop are single stranded.

Without being bound by theory, the stem-loop intermediate may be formed by the addition of nucleotides to the 3' end of the dumbbell shape intermediate. The dumbbell shape intermediate may therefore be extended from the 3' end. Extension from the 3' end of the dumbbell shape intermediate opens up the loop at the 5' end of the dumbbell shape structure, thereby converting the dumbbell shape intermediate into a stem-loop intermediate.

The amplification may further comprise LAMP cycling. The LAMP cycling may be initiated by FIP and optionally LB hybridizing to the loop of the stem-loop intermediate. The F2 region of FIP may hybridize to the F2c region of the loop of the stem-loop intermediate and optionally LB may hybridize to the LBc region of the loop of the stem-loop intermediate. Extension from the F2 region of FIP may displace the 3' end of the stem-loop intermediate (a new B1c and B1 region has been synthesized: the new B1 region will displace the B1 region of the stem-loop intermediate).

Nucleotides may then be added to the 3' end of the F1 region of the stem-loop intermediate. The extension of the F1 region of the stem-loop intermediate will displace the regions newly synthesized by the extension from the F2 region of FIP. This extension may then displace the strand extended from FIP. Once displaced, the stand extended from FIP may form a dumbbell shaped intermediate. This is because the strand extended from FIP may comprise, in the 5' to 3' direction a F1c region, a F2 region, a LFc region, a F1 region, a B1c region, a LB region, a B2c region and a B1 region. In addition, the addition of nucleotides to the 3' end of the F1 region of the 3' extended stem-loop intermediate may form another stem-loop intermediate.

Both the newly synthesized dumbbell shaped intermediate (i.e. the stand extended from FIP) and the new stem-loop intermediate may serve as templates for a BIP primed strand displacement reaction in a subsequent LAMP cycle.

Similarly, the LAMP cycling may be initiated by BIP and optionally LF hybridizing to the loop of the stem-loop intermediate comprising, in the 5' to 3' direction a F1c region, a F2 region, a LFc region, a F1 region, a B1c region, a LB region, a B2c region and a B1 region. In this case, both the newly synthesized dumbbell shaped intermediate (i.e. the stand extended from BIP) and the new stem-loop intermediate may serve as templates for a FIP primed strand displacement reaction in a subsequent LAMP cycle. Possible mechanisms of action are described further below.

(a)

Without being bound by theory, the FBa2 may anneal to the B1 region of the dumbbell shaped intermediate when the nucleic acid sequence comprises the second allele. Specifically, the B1c region of FBa2 may anneal to the B1 region of the dumbbell shaped intermediate. The annealing of FBa2 to the B1 region of the dumbbell shaped intermediate may prevent the formation of the loop of the dumbbell shaped intermediate. For example, the annealing of FBa2 to the B1 region of the dumbbell shaped intermediate may prevent the formation of the LB and B2c containing loop of the dumbbell shaped intermediate. The B2c region in the loop of the dumbbell shaped intermediate is the region to which the B2 region of BIPa1 anneals. The annealing of the B2 region of BIP to the B2c region of the loop of the dumbbell structure is thought to be essential for the BIP primed strand displacement reaction in a subsequent LAMP cycle, described above. Therefore, FBa2 will block BIPa1 mediated amplification of the nucleic acid sequence.

Similarly, BBa2 may anneal to the F1 region of the dumbbell shaped intermediate when the nucleic acid comprises the second allele. Specifically, the F1c region of BBa2 may anneal to the F1 region of the dumbbell shaped intermediate. The annealing of BBa2 to the F1 region of the dumbbell shaped intermediate may prevent the formation of the other loop of the dumbbell shaped intermediate. For example, the annealing of BBa2 to the F1 region of the dumbbell shaped intermediate may prevent the formation of the LFc and F2 containing loop of the dumbbell shaped intermediate.

The BBa2 may prime extension from their 3' end. This may result in the introduction of a double stranded region into the nucleic acid sequence comprising, in the 5' to 3' direction a F1c region, a LF region, a F2c region and a F1 region. This nucleic acid sequence may become single stranded and may be not capable of further amplification. This nucleic acid sequence may be not capable of further amplification because its self-complementarity between F1c and F1 regions forming a closed double stranded nucleic acid sequence where either FIP and/or BIP may not anneal. This nucleic acid sequence may become single stranded by the 3' end primed extension by FBa2.

The FBa2 may prime extension from their 3' end. This may result in the introduction of a double stranded region into the nucleic acid sequence. The dumbbell shaped intermediate may thus be converted into an at least partially double stranded nucleic acid sequence. The at least partially double stranded nucleic acid sequence may lack the single stranded loops containing the B2c region, LB region, the F2 region and LFc region. The double stranded nucleic acid sequence may therefore not be capable of further amplification.

(b)

Likewise, in connection with the reference strand, without being bound by theory, BBa2 may anneal to the F1 region of the dumbbell shaped intermediate when the nucleic acid sequence comprises the second allele. Specifically, the F1c region of BBa2 may anneal to the F1 region of the dumbbell shaped intermediate. The annealing of BBa2 to the F1 region of the dumbbell shaped intermediate may prevent the formation of the loop of the dumbbell shaped intermediate. For example, the annealing of FBa2 to the B1 region of the dumbbell shaped intermediate may prevent the formation of the LF and F2c containing loop of the dumbbell shaped intermediate. The F2c region in the loop of the dumbbell shaped intermediate is the region to which the F2 region of FIPa1 anneals. The annealing of the F2 region of FIP to the F2c region of the loop of the dumbbell structure is thought to be essential for FIP primed strand displacement reaction in a subsequent LAMP cycle. Therefore, BBa2 will block FIPa1 mediated amplification of the nucleic acid sequence.

Similarly, FBa2 may anneal to the B1 region of the dumbbell shaped intermediate when the nucleic acid comprises the second allele. Specifically, the B1c region of FBa2 may anneal to the B1 region of the dumbbell shaped intermediate. The annealing of FBa2 to the B1 region of the dumbbell shaped intermediate may prevent the formation of the other loop of the dumbbell shaped intermediate. For example, the annealing of FBa2 to the B1 region of the dumbbell shaped intermediate may prevent the formation of the LBc and B2 containing loop of the dumbbell shaped intermediate.

The FBa2 may prime extension from their 3' end. This may result in the introduction of a double stranded region into the nucleic acid sequence comprising, in the 5' to 3' direction a B1c region, a LB region, aB2 region and a B1 region. This nucleic acid sequence may become single stranded and may be not capable of further amplification. This nucleic acid sequence may be not capable of further amplification because its self-complementarity between B1c and B1 regions forming a closed double stranded nucleic acid sequence where neither FIP and/or BIP may anneal. This nucleic acid sequence may become single stranded by the 3' end primed extension by BBa2.

The BBa2 may prime extension from their 3' end. This may result in the introduction of a double stranded region into the nucleic acid sequence. The dumbbell shaped intermediate may thus be converted into an at least partially double stranded nucleic acid sequence. The at least partially double stranded nucleic acid sequence may lack the single stranded loops containing the F2c region, LF region, the B2 region and LBc region. The double stranded nucleic acid sequence may therefore not be capable of further amplification.

FBa2 and BIPa1 may compete for annealing to the dumbbell shaped intermediate. Since FBa2 targets the second allele and BIPa1 targets the first allele, FBa2 may anneal when the nucleic acid sequence comprises the second allele, while BIPa1 may anneal when the nucleic acid sequence comprises the first allele.

Likewise, BBa2 and FIPa1 may compete for annealing to the dumbbell shaped intermediate. Since BBa2 targets the second allele and FIPa1 targets the first allele, BBa2 may anneal when the nucleic acid sequence comprises the second allele, while FIPa1 may anneal when the nucleic acid sequence comprises the first allele.

FIPa1 or BIPa1 may bind to the nucleic acid sequence in the presence of the second allele before BBa2 and/or FBa2 do. Accordingly, the 3' end primed extension may be the nucleic acid sequences described in either (a) or (b) above.

The amplification may be selective amplification of the first allele. Without being bound by theory, the selective amplification of the first allele may be because in the presence of the first allele, the annealing of the F1c region of FIPa1 and the B1c region of BIPa1 to the nucleic acid sequence is more energetically favorable than the annealing of FBa2 and BBa2 to the nucleic acid sequence and, in the presence of the second allele, the annealing of the F1c region of FIPa1 and the B1c region of BIPa1 to the nucleic acid sequence is less energetically favorable than the annealing of FBa2 and BBa2 to the nucleic acid sequence. Accordingly, the amplifying may be further characterized as wherein in the presence of the first allele, the annealing of the F1c region of FIPa1 and the B1c region of BIPa1 to the nucleic acid sequence is more energetically favorable than the annealing of FBa2 and BBa2 to the nucleic acid sequence and in the presence of the second allele, the annealing of the F1c region of FIPa1 and the B1c region of BIPa1 to the nucleic acid sequence is less energetically favorable than the annealing of FBa2 and BBa2 to the nucleic acid sequence, resulting in selective amplification of the first allele.

Accordingly, the relationships between the annealing of the F1c region of FIPa1, the B1c region of BIPa1, FBa2 and BBa2 to the nucleic acid sequence may be described in terms of a change in Gibbs free energy (AG):

When the nucleic acid sequence comprises the first allele:

$\Delta G$ F1c region of FIPa1 annealing $<$ BBa2 annealing $\Delta G$ B1c region of BIPa1 annealing $<$ FBa2 annealing When the nucleic acid sequence comprises the second allele:

$\Delta G$ F1c region of FIPa1 annealing $>$ BBa2 annealing $\Delta G$ B1c region of BIPa1 annealing $>$ FBa2 annealing Accordingly, it may be that $\Delta G$ (F1c/B1c) $>$ $\Delta G$ (FB/BB), for example because FB/BB have been designed to be longer than F1c/B1c.

Without being bound by theory, a number of features of FIPa1, BIPa1, FBa2 and BBa2 may, alone or in any combination, contribute to the selective amplification of the first allele. The selective amplification of the first allele may be related to:

- Complementarity to the SNP i.e. in which alleles presence each primer anneals to the nucleic acid,
- The location of the SNP within the sequence of BBa2,
- The location of the SNP within the sequence of FBa2,
- The relative lengths of the F1c region of FIPa1 and of BBa2,
- The relative lengths of the B1c region of BIPa1 and of FBa2,
- The relative concentrations of FIPa1 and BBa2 in the reaction mixture, and/or
- The relative concentrations of BIPa1 and FBa2 in the reaction mixture.

The SNP may be located proximal to the 5' end of BBa2 and/or FBa2. The SNP may be located proximal to the 5' end of the F1c region of BBa2 and/or B1c region of FBa2. The SNP may be in the 5' half of BBa2 and/or FBa2. Proximal to the 5' end may be at any point closer to the 5' end of BBa2 and/or FBa2 than the 3' end of BBa2 and/or FBa2. For example, the SNP may be in the 5' half of BBa2 and/or FBa2, the 5' third of BBa2 and/or FBa2, the 5' quarter of BBa2 and/or FBa2, the 5' fifth of BBa2 and/or FBa2, the 5' sixth of BBa2 and/or FBa2, the 5' seventh of BBa2 and/or FBa2, the 5' eighth of BBa2 and/or FBa2, the 5' ninth of BBa2 and/or FBa2 or the 5' tenth of BBa2 and/or FBa2. The SNP may be the first to the fifth nucleotide from the 5' end of BBa2 and/or FBa2. Accordingly, the SNP may be the first, second, third, fourth or fifth nucleotide from the 5' end of BBa2 and/or FBa2. The SNP may be the first to the third nucleotide from the 5' end of BBa2 and/or FBa2. Accordingly, the SNP may be the first, second or third nucleotide from the 5' end of BBa2 and/or FBa2. When the SNP is not the first nucleotide from the 5' end of BBa2 and/or FBa2, the SNP may be described as being "displaced" from the 5' end of BBa2 and/or FBa2.

BBa2 may be equal to or longer than the F1c region of FIPa1. BBa2 may be 0 to 10 nucleotides longer than the F1c region of FIPa1. BBa2 may therefore be 0, 1, 2, 3, 4, 5, 6, 7, 8, 9 or 10 nucleotides longer than the F1c region of FIPa1. BBa2 may be 0 to 6 nucleotides longer than the F1c region of FIPa1. BBa2 may be 0 to 3 nucleotides longer than the F1c region of FIPa1. BBa2 may be longer that the F1c region of FIPa1 at the 5' end and/or the 3" end. BBa2 may be longer than the F1c region of FIPa1 at the 3' end of BBa2. Accordingly, the 3' end of BBa2 may be 1 to 10 nucleotides longer than the 3' end of the F1c region of FIPa1. The 3' end of BBa2 may be 1 to 6 nucleotides longer than the 3' end of the F1c region of FIPa1. The 3' end of BBa2 may be 1, 2, 3, 4, 5 or 6 nucleotides longer than the 3' end of the F1c region of FIPa1. The 3' end of BBa2 may be 1 to 3 nucleotides longer than the 3' end of the F1c region of FIPa1. The 3' end of BBa2 may be 1, 2 or 3 nucleotides longer than the 3' end of the F1c region of FIPa1. BBa2 may be longer than the F1c region of FIPa1 at the 5' end of BBa2. Accordingly, the 5' end of BBa2 may be 1 to 10 nucleotides longer than the 5' end of the F1c region of FIPa1. The 5' end of BBa2 may be 1 to 6 nucleotides longer than the 5' end of the F1c region of FIPa1. The 5' end of BBa2 may be 1, 2, 3, 4, 5 or 6 nucleotides longer than the 5' end of the F1c region of FIPa1. The 5' end of BBa2 may be 1 to 3 nucleotides longer than the 5' end of the F1c region of FIPa1. The 5' end of BBa2 may be 1, 2 or 3 nucleotides longer than the 5' end of the F1c region of FIPa1.

FBa2 may be equal to or longer than the B1c region of BIPa1. FBa2 may be 0 to 10 nucleotides longer than the B1c region of BIPa1. FBa2 may therefore be 0, 1, 2, 3, 4, 5, 6, 7, 8, 9 or 10 nucleotides longer than the B1c region of BIPa1. FBa2 may be 0 to 6 nucleotides longer than the B1c region of BIPa1. FBa2 may be 0 to 3 nucleotides longer than the B1c region of BIPa1. FBa2 may be longer that the B1c region of BIPa1 at the 5' end and/or the 3' end. FBa2 may be longer than the B1c region of BIPa1 at the 3' end of FBa2. Accordingly, the 3' end of FBa2 may be 1 to 10 nucleotides longer than the 3' end of the B1c region of BIPa1. The 3' end of FBa2 may be 1 to 6 nucleotides longer than the 3' end of the B1c region of BIPa1. FBa2 may be 1, 2, 3, 4, 5 or 6 nucleotides longer than the 3' end of the B1c region of BIPa1. FBa2 may be 1 to 3 nucleotides longer than the 3' end of the B1c region of BIPa1. FBa2 may be 1, 2 or 3 nucleotides longer than the 3' end of the B1c region of BIPa1. FBa2 may be longer than the B1c region of BIPa1 at the 5' end of FBa2. Accordingly, the 5' end of FBa2 may be 1 to 10 nucleotides longer than the 5' end of the B1c region of BIPa1. Accordingly, the 5' end of FBa2 may be 1 to 6 nucleotides longer than the 5' end of the B1c region of BIPa1. FBa2 may be 1, 2, 3, 4, 5 or 6 nucleotides longer than the 5' end of the B1c region of BIPa1. FBa2 may be 1 to 3 nucleotides longer than the 5' end of the B1c region of BIPa1. FBa2 may be 1, 2 or 3 nucleotides longer than the 5' end of the B1c region of BIPa1.

The concentration of FIPa1 and/or BIPa1 in the reaction mixture may be about 0.5 μM to about 10 μM. The concentration of FIPa1 and/or BIPa1 in the reaction mixture may be about 1 μM to about 5 μM. For example, the concentration of FIPa1 and/or BIPa1 in the reaction mixture may be about 1 μM, about 1.5 μM, about 2 μM, about 2.5 μM, about 3 μM, about 3.5 μM, about 4 μM, about 4.5 μM or about 5 μM. The concentration of FIPa1 and/or BIPa1 in the reaction mixture may be about 1.5 μM to about 2.5 μM. For example, the concentration of FIPa1 and/or BIPa1 in the reaction mixture may be about 1.5 μM, about 1.75 μM, about 2.0 μM, about 2.25 μM or about 2.5 μM. The concentration of FIPa1 and/or BIPa1 in the reaction mixture may be about 2 μM.

The concentration of FIPa1 in the reaction mixture may be equal to the concentration of BIPa1 in the reaction mixture. Alternatively, the concentration of FIPa1 may be different to the concentration of BIPa1. Any concentration of FIPa1 described herein may be combined with any concentration of BIPa1 described herein.

The concentration of FBa2 and/or BBa2 in the reaction mixture may be about 0.5 μM to about 10 μM. The concentration of FBa2 and/or BBa2 in the reaction mixture may be about 1 μM to about 5 μM. For example, the concentration of FBa2 and/or BBa2 in the reaction mixture may be about 1 μM, about 1.5 μM, about 2 μM, about 2.5 μM, about 3 μM, about 3.5 μM, about 4 μM, about 4.5 μM or about 5 μM. The concentration of FBa2 and/or BBa2 in the reaction mixture may be about 3 μM to about 4 μM. For example, the concentration of FBa2 and/or BBa2 in the reaction mixture may be about 3 μM, about 3.25 μM, about 3.5 μM, about 3.75 μM or about 4 μM.

The concentration of FBa2 in the reaction mixture may be equal to the concentration of BBa2 in the reaction mixture. Alternatively, the concentration of FBa2 may be different to the concentration of BBa2. Any concentration of FBa2 described herein may be combined with any concentration of BBa2 described herein.

The concentration of BBa2 in the reaction mixture may be less than, equal to, or higher than the concentration of FIPa1. Likewise, the concentration of FBa2 in the reaction mixture may be less than, equal to, or higher than the concentration of BIPa1. The concentration of BBa2 in the reaction mixture may be higher than the concentration of FIPa1. Likewise, the concentration of FBa2 in the reaction mixture may be higher than the concentration of BIPa1.

The concentration of BBa2 in the reaction mixture may be up to 6 μM higher than the concentration of FIPa1. The concentration of BBa2 in the reaction mixture may be up to 3 μM higher than the concentration of FIPa1. For example, the concentration of BBa2 in the reaction mixture may be up to 3 μM higher, up to 2 μM higher, or up to 1 μM higher, than the concentration of FIPa1. The concentration of BBa2 in the reaction mixture may be up to 4 times higher than the concentration of FIPa1. The concentration of BBa2 in the reaction mixture may be up to 2.5 times higher than the concentration of FIPa1. For example, the concentration of BBa2 in the reaction mixture may be up to 2.5 times higher, up to 2 times higher, or up to 1.5 times higher, than the concentration of FIPa1.

The concentration of FBa2 in the reaction mixture may be up to 6 μM higher than the concentration of BIPa1. The concentration of FBa2 in the reaction mixture may be up to 3 μM higher than the concentration of BIPa1. For example, the concentration of FBa2 in the reaction mixture may be up to 3 μM higher, up to 2 μM higher, or up to 1 μM higher, than the concentration of BIPa1. The concentration of FBa2 in the reaction mixture may be up to 4 times higher than the concentration of BIPa1. The concentration of FBa2 in the reaction mixture may be up to 2.5 times higher than the concentration of BIPa1. For example, the concentration of FBa2 in the reaction mixture may be up to 2.5 times higher, up to 2 times higher, or up to 1.5 times higher, than the concentration of BIPa1.

The reaction mixture may further comprise a forward outer primer (F3, also known as FOP) and/or a backward outer primer (B3, also known as BOP).

F3 comprises a sequence that is complementary to an F3c region of the nucleic acid. F3 is configured to anneal under stringent conditions to an F3c region of the nucleic acid. The F3c region of the nucleic acid is displaced from the F2c region of the nucleic acid in the 3' direction.

B3 comprises a sequence that is complementary to a B3c region of the nucleic acid. B3 is configured to anneal under stringent conditions to a B3c region of the nucleic acid. The B3c region of the nucleic acid is displaced from the B2c region of the nucleic acid in the 3' direction.

The distance between F2c and F3c, from 3' to 3', may be around 20 to 40 base pairs. The distance between B2c and B3c, from 3' to 3', may be around 20 to 40 base pairs.

The present inventors have determined that detectable amplification of the nucleic acid can occur in the absence of F3 and/or B3. Without being bound by theory this is thought to be possible due to stochastic dissociation of a 5' portion of a FIP (for example the FIPa1 described above), such as the F2 region of FIP, after it has been extended by the nucleic acid polymerase. Stochastic dissociation of a 5' portion of extended FIP may allow for annealing of a non-extended FIP. The non-extended FIP may then be extended, displacing the previously extended FIP. Likewise, without being bound by theory, a 5' portion of BIP (for example the BIPa1 described above), such as the B2 region of BIP may also undergo stochastic dissociation after it has been extended by the nucleic acid polymerase. Stochastic dissociation of a 5' portion of extended BIP may allow for annealing of a non-extended BIP. The non-extended BIP may then be extended, displacing the previously extended BIP. However, the inclusion of F3 and/or B3 enhances the efficiency of amplification. This is because F3 does not need to compete with FIP for binding to the nucleic acid. Likewise, B3 does not need to compete with BIP for binding to the nucleic acid.

The reaction mixture may further comprise a forward loop primer (LF) and/or a backward loop primer (LB).

LF comprises a sequence that corresponds to a LF region of the nucleic acid. The LF region of the nucleic acid is displaced from the F2c region in the 5' direction and is displaced from the F1c region in the 3' direction. Thus, the LF region lies between the F1c and the F2c regions of the nucleic acid. LF is complementary to an LFc region, which is formed by extension of FIP and/or BIP (for example the FIPa1 and/or BIPa1 described above) that has annealed to the F2 region and/or B2 region of the nucleic acid. LF therefore anneals to the LFc region of the extended FIP and/or BIP under stringent conditions. LF therefore primes extension of extended FIP and/or BIP from an additional site.

LB comprises a sequence that corresponds to a LB region of the nucleic acid. The LB region of the nucleic acid is displaced from the B2c region in the 5' direction and is displaced from the B1c region in the 3' direction. Thus, the LB region lies between the B1c and the B2c regions of the nucleic acid. LB is complementary to an LBc region, which is formed by extension of BIP and/or FIP (for example the BIPa1 and/or FIPa1 described above) that has annealed to the B2 region and/or F2 region of the nucleic acid. LB therefore anneals to the LBc region of the extended BIP and/or FIP under stringent conditions. LB therefore primes extension of extended BIP and/or FIP from an additional site.

Detectable amplification may occur in the absence of LF and LB. However, the inclusion of LF and LB enhances the efficiency of amplification. This may be because LF does not need to compete with the other primers for binding to the nucleic acid. Likewise, LB may not need to compete with the other primers for binding to the nucleic acid. Moreover, LF and LB may interact with FIP and BIP in the same way that F3 and B3 do with FIP and BIP.

The primers FIPa1, BIPa1, BBa2, FBa2 F3, B3, LF and/or LB may be stored as a primer mixture and may therefore be added to the reaction mixture together.

The sample may be any suitable sample comprising a nucleic acid. For example, the sample may be an environmental sample or a clinical sample. The sample may also be a sample of synthetic DNA (such as gBlocks) or a sample of a plasmid. The plasmid may include a gene or gene fragment of interest.

The environmental sample may be a sample from air, water, animal matter, plant matter or a surface. An environmental sample from water may be salt water, brackish water or fresh water. For example, an environmental sample from salt water may be from an ocean, sea or salt marsh. An environmental sample from brackish water may be from an estuary. An environmental sample from fresh water may be from a natural source such as a puddle, pond, stream, river, lake. An environmental sample from fresh water may also be from a man-made source such as a water supply system, a storage tank, a canal or a reservoir. An environmental sample from animal matter may, for example, be from a dead animal or a biopsy of a live animal. An environmental sample from plant matter may, for example, be from a foodstock, a plant bulb or a plant seed. An environmental sample from a surface may be from an indoor or an outdoor surface. For example, the outdoor surface be soil or compost. The indoor surface may, for example, be from a hospital, such as an operating theatre or surgical equipment, or from a dwelling, such as a food preparation area, food preparation equipment or utensils. The environmental sample may contain or be suspected of containing a pathogen. Accordingly, the nucleic acid may be a nucleic acid from the pathogen.

The clinical sample may be a sample from a patient. The nucleic acid may be a nucleic acid from the patient. The clinical sample may be a sample from a bodily fluid. The clinical sample may be from blood, serum, lymph, urine, faeces, semen, sweat, tears, amniotic fluid, wound exudate or any other bodily fluid or secretion in a state of heath or disease. The clinical sample may be a sample of cells or a cellular sample. The clinical sample may be a sample of cells or a cellular sample. The clinical sample may comprise cells. The clinical sample may be a tissue sample. The clinical sample may be a biopsy.

The clinical sample may be from a tumor. The clinical sample may comprise cancer cells. Accordingly, the nucleic acid may be a nucleic acid from a cancer cell.

The sample may be obtained by any suitable method. Accordingly, the method of the invention may comprise a step of obtaining the sample. For example, the environmental air sample may be obtained by impingement in liquids, impaction on solid surfaces, sedimentation, filtration, centrifugation, electrostatic precipitation, or thermal precipitation. The water sample may be obtained by containment, by using pour plates, spread plates or membrane filtration. The surface sample may be obtained by a sample/rinse method, by direct immersion, by containment, or by replicate organism direct agar contact (RODAC).

The sample from a patient may contain or be suspected of containing a pathogen. Accordingly, the nucleic acid may be a nucleic acid from the pathogen. Alternatively, the nucleic acid may be a nucleic acid from the host.

The method of the invention may be an in vitro method or an ex vivo method.

The pathogen may be any entity comprising a nucleic acid comprising a SNP. The pathogen may be a eukaryote, a prokaryote or a virus. The pathogen may be an animal, a plant, a fungus, a protozoan, a chromist, a bacterium or an archaeum.

The pathogen may be from the pylum Apicomplexa. The pathogen may be from the class Aconoidasida. The pathogen may be from the order Haemosporida. The pathogen may be from the Family Plasmodiidae. The pathogen may be from the genus *Plasmodium*. The pathogen may be selected from the group consisting of *Plasmodium falciparum, Plasmodium ovale, Plasmodium ovale* wallikeri, *Plasmodium ovale curtisi, Plasmodium vivax, Plasmodium malariae* and *Plasmodium knowlesi*. The pathogen may be *Plasmodium falciparum.*

The pathogen may be a malaria causing pathogen. The pathogen may be associated with malaria. The malaria may be human-infective malaria.

The pathogen may be from the pylum Ascomycota. The pathogen may be from the class Eurotiomycetes. The pathogen may be from the order Eurotiales. The pathogen may be from the Family Trichocomaceae. The pathogen may be from the genus *Aspergillus*. The pathogen may be *Aspergillus fumigatus.*

The nucleic acid may be isolated, extracted and/or purified from the sample prior to use in the method of the invention. The isolation, extraction and/or purification may be performed by any suitable technique. For example, the nucleic acid isolation, extraction and/or purification may be performed using a nucleic acid isolation kit, a nucleic acid extraction kit or a nucleic acid purification kit, respectively.

The method of the invention may further comprise an initial step of isolating, extracting and/or purifying the nucleic acid from the sample. The method may therefore further comprise isolating the nucleic acid from the sample. The method may further comprise extracting the nucleic acid from the sample. The method may further comprise purifying the nucleic acid from the sample. Alternatively, the method may comprise direct amplification from the sample without an initial step of isolating, extracting and/or purifying the nucleic acid from the sample. Accordingly, the method may comprise lysing cells in the sample or amplifying free circulating DNA.

Following isolation, extraction and/or purification, the nucleic acid may be used immediately or may be stored under suitable conditions prior to use. Accordingly, the method of the invention may further comprise a step of storing the nucleic acid after the extracting step and before the amplifying step.

The step of obtaining the sample and/or the step of isolating, extracting and/or purifying the nucleic acid from the sample may occur in a different location to the subsequent steps of the method. Accordingly, the method may further comprise a step of transporting the sample and/or transporting the nucleic acid.

It is possible for the method to be performed at the point-of-care. As used herein "at the point-of-care" means in the same or a nearby location to the place where the sample originates. In other words, it may not be necessary to transport the sample, or the nucleic acid, and/or to perform any of the method steps in a location remote from the location at which the sample was obtained. When the sample is a clinical sample, the point-of-care may be the location of the patient from whom the clinical sample was obtained, or a location nearby. When the sample is an environmental sample, the point-of-care may be the location of the air, water, animal matter, plant matter or a surface from whom the environmental sample was obtained, or a location nearby. The method of the invention may be suitable for use at the point-of-care. Accordingly, the method may be described as a method for detecting a SNP in a nucleic acid sequence at the point-of-care. One, more or all of the method steps may be described as being performed at the point-of-care. The amplifying step may be performed at the point-of-care. The detecting step may be performed at the point-of-care. The step of obtaining the sample and/or the step of isolating, extracting and/or purifying the nucleic acid from the sample may be performed at the point-of-care. However, the method can be performed at any location (such as a clinical site, hospital etc) and not necessarily at the point of care.

Accordingly, the method may be performed extemporaneously. As used herein "extemporaneously" means as soon as the sample is obtained, without delay after the sample is obtained, without transporting the sample, in the same or nearby location to the place where the sample originates and/or at the point-of-care. The method may be performed extemporaneously on the sample. The method may be performed extemporaneously by the same individual who took the sample. For example, the method may be performed extemporaneously by the medical practitioner who took the sample.

A SNP is a variation in a single nucleotide that occurs at a specific position in a nucleic acid sequence, where each variation is present to some appreciable degree within a population. If more than 1% of a population does not carry the same nucleotide at a specific position in the nucleic acid sequence, then this variation can be classified as a SNP. If a SNP occurs within a gene, then the gene is described as having more than one allele. In these cases. SNPs may lead to variations in the amino acid sequence. A SNP that leads to a variation in amino acid sequence may be described as "non-synonymous" or "nonsynonymous". Alternatively, SNPs may not lead to variation in amino acid sequence. In this case, the SNP may be described as "synonymous" or "synonymous": SNPs, however, are not just associated with genes; they can also occur in noncoding regions of DNA. For the purposes of this disclosure the term "allele" may also refer to variation at a SNP in a noncoding region of DNA For example, at a specific base position in a nucleic acid sequence, the C nucleotide may appear in most individuals, but in a minority of individuals, the position is occupied by an A. This means that there is a SNP at this specific position, and the two possible nucleotide variations—C or A—are said to be alleles for this position.

Some SNPs have more than two alleles. Further reactions may be added to the method of the invention (with any necessary additional primer sets) to distinguish three, or four alleles at a SNP. Each reaction may be specific to an allele. Alternatively, a single primer set may be designed to amplify more than one allele, such as two alleles. For example, a first primer set may be designed to detect a first allele and a second primer set may be designed to detect a second, third and/or fourth allele.

The SNP may contribute to and/or define drug resistance in the pathogen. For example, when the pathogen is a *Plasmodium falciparum*, the SNP may contribute to and/or define artemisinin resistance. Artemisinin resistance may be resistance to an artemisinin-based combination therapy. When the pathogen is a *Plasmodium falciparum*, the SNP may contribute to and/or define artemisinin resistance.

As used herein, the term "drug" refers to a therapeutic or prophylactic agent. The drug may therefore be an active ingredient in a pharmaceutical composition or in a pharmaceutical formulation. The drug may be a pharmaceutical composition or in a pharmaceutical formulation. The drug may be a combination therapy.

As used herein the term "drug resistance" refers to the ability of an organism, such as a pathogen, to survive treatment with a drug. An organism exhibiting "drug resistance" may be described as "drug resistant". Drug resistance may be measured by comparison with a control organism which has undergone the same treatment with the same drug. When compared with a control organism the organism suspected of being drug resistant may be described as the "test" organism. A sample of the test organism and a sample of the control organism may be compared. Any suitable measure may be used. For example, the drug resistant organism may survive longer, grow at a faster rate, divide or proliferate at a faster rate and/or die at a slower rate than the control organism. Drug resistance may be defined by DNA sequence and/or gene expression. For example, when a DNA sequence is known to contribute to and/or define drug resistance the presence or absence of the DNA sequence may be determined by any suitable technique. Likewise, when gene expression is known to contribute to and/or define drug resistance, the gene expression may be determined by any suitable technique.

An infection may also be described as drug resistant if it has the ability to survive treatment with a drug. A drug resistant infection may comprise a drug resistant organism, such as a drug resistant pathogen. The test sample may be from the infection by any suitable means, such as a swab or a biopsy or any means described herein in connection with a clinical sample.

When the pathogen is *Plasmodium falciparum*, the SNP may be in the *Plasmodium falciparum* kelch 13 gene. For example, the SNP may be C580Y in the *Plasmodium falciparum* kelch 13 gene; F446I in the *Plasmodium falciparum* kelch 13 gene; Y493H in the *Plasmodium falciparum* kelch 13 gene; R539T in the *Plasmodium falciparum* kelch 13 gene; 1543T in the *Plasmodium falciparum* kelch 13 gene; or P553L in the *Plasmodium falciparum* kelch 13 gene.

When the SNP is C580Y in the *Plasmodium falciparum* kelch 13 gene, the primer sequences may comprise one or more the following primer sequences (written in the 5' to 3' direction):

(i) FIPa1 may comprise (SEQ ID NO: 1)
TACATAGCTGATGATCTTATGATCATCGTATGAAAGCATG (ii) BIPa1 may comprise (SEQ ID NO: 2)
ATGTTGCTTTTGATAATAAAATTTATGCTAATAAGGCATATGGAAATTG (iii) FBa2 may comprise TGTGTTGCTTTTGATAATAAAATTTATG (SEQ ID NO: 3)

(iv) BBa2 may comprise CACACATAGCTGATGATCTAGGG (SEQ ID NO: 4)

(v) F3 may comprise CTATTATACCGAATGTAGAAGCA (SEQ ID NO: 5)

(vi) B3 may comprise TGCTCCTGAACTTCTAGC (SEQ ID NO: 6)

(vii) LF may comprise TCAAAGGTGCCACCTCTACC (SEQ ID NO: 7)

(viii) LB may comprise GGTGGAACTAATGGTGAGAGATTAA (SEQ ID NO: 8).

When the SNP is Y493H in the *Plasmodium falciparum* kelch 13 gene, the primer sequences may comprise one or more the following primer sequences (written in the 5' to 3' direction):

(i) FIPa1 may comprise (SEQ ID NO: 9)
GTAAGAAATTATTCAATACAGATTAGATATTAGTCAACAATGCTGG (ii) BIPa1 may comprise (SEQ ID NO: 10)
CACGTTTTTGGTGGTAAAAACGATCATACACCTCAGTT (iii) FBa2 may comprise ATACGTTTTTGGTGGTAATAACTAT (SEQ ID NO: 11)

(iv) BBa2 may comprise ATAAGAAATTATTCAATACAGCACTT (SEQ ID NO: 12)

(v) F3 may comprise GGTGTAGAATATTTAAATTCGATGG (SEQ ID NO: 13)

(vi) B3 may comprise TTGAAACATACCATACATCTCTT (SEQ ID NO: 14)

(vii) LF may comprise TGGTAGACATAGGTGTACACATACG (SEQ ID NO: 15)

(viii) LB may comprise ATTATAAGGCTTTATTGA (SEQ ID NO: 16).

When the SNP is R539T in the *Plasmodium falciparum* kelch 13 gene, the primer sequences may comprise one or more the following primer sequences (written in the 5' to 3' direction):

(i) FIPa1 may comprise

```
                                    (SEQ ID NO: 17)
GTACCATTTGACGTAACACTAAGAGATGTATGGTATGTTTCAAG
```

(ii) BIPa1 may comprise

```
                                    (SEQ ID NO: 18)
CAATTTATTGTATTGGGGGATCATATGCTTCTACATTCGGTAT
```

(iii) FBa2 may comprise TAGAATTTATTGTATTGGGGGATAT (SEQ ID NO: 19)

(iv) BBa2 may comprise CTACCATTTGACGTAACACCAC (SEQ ID NO: 20)

(v) F3 may comprise AACTGAGGTGTATGATCGTT (SEQ ID NO: 21)

(vi) B3 may comprise ACCCATGCTTTCATACGA (SEQ ID NO: 22)

(vii) LF may comprise TTATTTCTTCTAGGTATATTT (SEQ ID NO: 23)

(viii) LB may comprise ATGATGGCTCTTCTATT (SEQ ID NO: 24).

When the pathogen is HIV, the SNP may contribute to and/or define drug resistance in HIV. For example, the SNP may contribute to and/or define resistance to non-nucleoside reverse transcriptase inhibitors (NNRTIs), nucleoside reverse transcriptase inhibitors (NRTIs or 'nukes') and/or protease inhibitors (PI). Accordingly, the SNP may be a SNP that results in any one of the following mutations associated with HIV drug resistance (as defined in the World Health Organization 2009 list of mutations for surveillance of transmitted drug resistant HIV strains from Drug Resistance Mutations for Surveillance of Transmitted HIV-1 Drug-Resistance: 2009 Update, Bennett et al), in Table 1 below.

TABLE 1

Mutations for surveillance of transmitted drug resistant HIV strains

| NNRTIs | | NRTIs | | PI | |
|---|---|---|---|---|---|
| M41 | L | L100 | I | L23 | I |
| K65 | R | K101 | E, P | L24 | I |
| D67 | N, G, E | K103 | N, S | D30 | N |
| T69 | D, Ins | V106 | M, A | V32 | I |
| K70 | R, E | V179 | F | M46 | I, L |
| L74 | V, I | Y181 | C, I, V | I47 | V, A |
| V75 | M, T, A, S | Y188 | L, H, C | G48 | V, M |
| F77 | L | G190 | A, S, E | I50 | V, L |
| Y115 | F | P225 | H | F53 | L, Y |
| F116 | Y | M230 | L | I54 | V, L, M, A, T, S |
| Q151 | M | | | G73 | S, T, C, A |
| M184 | V, I | | | L76 | V |
| L210 | W | | | V82 | A, T, F, S, C, M, L |
| T215 | Y, F, I, S, C, D, V, E | | | N83 | D |
| K219 | Q, E, N, R | | | I84 | V, A, C |
| F77 | L | | | I85 | V |
| | | | | N88 | D, S |
| | | | | L90 | M |

When the pathogen is *Mycobacterium tuberculosis* (TB), the SNP may contribute to and/or define drug resistance in TB. For example, the SNP may contribute to and/or define resistance to Quinolones, Isoniazid, Ethionamide, Ethionamide/Isoniazid, Streptomycin, Rifampicin, Ethambutol, Thiacetazone, Pyrazinamide, Capreomycin, Cycloserine, PA-824 and/or Benzothiazinones (BTZ043). Accordingly, the SNP may be a SNP that results in any one of the following mutations associated with TB drug resistance (as defined in Regmi et al International Journal of Mycobacteriology, Volume 4, Issue 1, 2015, Pages 67-72), in Table 2 below:

TABLE 2

Mutations associated with TB drug resistance

| Drugs | Genes | Locus | Annotations | Positions (of H37Rv reference) | Base change | Amino acid change | Comments |
|---|---|---|---|---|---|---|---|
| Quinolones | gyrA | Rv0006 | DNA gyrase subunit A | 7362 | G > C | E21Q | Nonsynonymous |
| | | | | 7585 | G > C | S95T | Nonsynonymous |
| | | | | 9304 | G > A | G668D | Nonsynonymous |
| Isoniazid | Rv1592c | Rv1592c | Conserved hypothetical protein | 1,792,777 | T > C | I322V | Nonsynonymous |
| | | | | 1,792,778 | T > C | E321E | Synonymous |
| | kat | Rv1908c | Catalase-peroxidase-peroxy-nitrilase T katG | 2,154,724 | C > A | R463L | Nonsynonymous |
| | accD6 | Rv2247 | Acetyl/propionyl-CoA carboxylase beta subunit | 2,521,342 | T > C | D200D | Synonymous |
| | | | | 2,521,428 | A > G | D229G | Nonsynonymous |
| Ethionamide/ | mshA | Rv0486 | Mannosyltransferase | 575,907 | C > T | A187V | Nonsynonymous |
| Isoniazid | nudC | Rv3199c | NADH pyrophosphatase | 3,571,828 | G > C | P239R | Nonsynonymous |
| Streptomycin | tap | Rv1258c | Conserved membrane transport protein | 1,406,760 | AG > ACG | InsC580-581 | Frame shift |
| | gidB | Rv3919c | Probable glucose-inhibited division protein B | 4,407,588 | T > C | A205A | Synonymous |
| | | | | 4,407,927 | T > G | E92D | Nonsynonymous |

TABLE 2-continued

Mutations associated with TB drug resistance

| Drugs | Genes | Locus | Annotations | Positions (of H37Rv reference) | Base change | Amino acid change | Comments |
|---|---|---|---|---|---|---|---|
| Rifampicin | rpoB | Rv0667 | DNA-directed RNA polymerase beta chain | 763,031 | T > C | A1075A | Synonymous |
| Ethambutol | embC | Rv3793 | Membrane indolylacetylinositol arabinosyltransferase embC | 4,242,643 | C > T | R927R | Synonymous |
| | embA | Rv3794 | Membrane indolylacetylinositol arabinosyltransferase embA | 4,243,460 | C > T | C76C | Synonymous |
| Thiacetazone | mmaA2 | Rv0644c | Methoxy mycolic acid synthase 2 | 738,522 | T > G | E213D | Nonsynonymous |
| Pyrazinamide | rpsA | Rv1630 | 30S ribosomal protein S1 | 1,834,177 | A > C | R212R | Synonymous |
| Capreomycin | tlyA[ | Rv1694 | Cytotoxin/haemolysin homologue | 1,917,972 | A > G | L11L | Synonymous |
| Cycloserine | cycA | Rv1704c | D-serine/alanine/glycine transporter protein | 1,931,179 | C > A | R93L | Nonsynonymous |
| Cycloserine | ddlA | Rv2981c | D-alanine-D-alanine ligase | 3,336,825 | T > C | T365A | Nonsynonymous |
| PA-824 | fgd1 | Rv0407 | F420-dependent glucose-6-phosphate dehydrogenase | 491,742 | T > C | F320F | Synonymous |
| Benzothiazin ones (BTZ043) | dprE1 | Rv3790 | Probable oxidoreductase | 4,236,237 | C > T | T153T | Synonymous |

Alternatively, when the nucleic acid is a nucleic acid from the host, the SNP may contribute to or define a characteristic of the host. The characteristic of the host may be susceptibility to infection.

Accordingly, the method may alternatively be defined as a method of screening for susceptibility to infection by detecting a first allele of a SNP in a nucleic acid sequence: a method of diagnosing susceptibility to infection by detecting a first allele of a SNP in a nucleic acid sequence; and/or a method for prophylactically treating infection comprising detecting a first allele of a SNP in a nucleic acid sequence and prophylactically treating an infection when the first allele of the SNP is present.

When the nucleic acid is from a clinical sample, the SNP may contribute to or define disease, disorder or trait risk. The disease disorder or trait may be any disease disorder or trait to which a SNP is known to contribute or define risk. For example, the SNP may contribute to or define risk of an autoimmune disease, a cancer, a cardiovascular disease, a digestive disease or disorder, a female-specific disorder, a genetic disease, a neurodegenerative disease, a neuro-psychological condition or disorder, a neuro-psychological trait, an addiction or substance dependence.

The SNP may contribute to or define risk of an autoimmune disease selected from the group consisting of allergies, ankylosing spondylitis, asthma, Celiac disease, Crohn's disease, type-1 diabetes, type-2 diabetes, Graves' disease, inflammatory bowel disease, multiple sclerosis, psoriasis, rheumatoid arthritis, Sjögren's syndrome, systemic lupus erythematosis (lupus), and ulcerative colitis.

The SNP may contribute to or define risk of a cancer selected from the group consisting of bladder cancer, brain cancer, breast cancer, cervical cancer, collorectal cancer, endometrial (uterus) cancer, gallbladder cancer, gastric (stomach) cancer, leukemia (blood cancer), liver cancer, lung cancer, neuroblastoma, non-Hodgkin lymphoma, oral and larynx cancer, ovarian cancer, pancreatic cancer, prostate cancer, skin cancer (basal cell carcinoma), skin cancer (melanoma), testicular cancer and thyroid cancer. The SNP may also contribute to and or define general cancer risk or be a preventive allele.

The SNP may contribute to or define risk of a cardiovascular disease selected from the group consisting of aneurysm (abdominal aortic), aneurysm (intracranial), atherosclerosis (hyperlipidemia), atrial fibrillation, cardiovascular disease (general), cardiovascular disease (cholesterol level), myocardial infarction (heart attack), peripheral arterial disease pre-eclampsia, stroke and venous thromboembolism.

The SNP may contribute to or define risk of a digestive disease or disorder selected from the group consisting of acid reflux disease (GERD), acid reflux disease (eosinophilic esophagitis), Celiac disease, Crohn's disease, gallstones, inflammatory bowel disease, kidney disease, kidney stones (hypercalcaemia), non-alcoholic fatty liver disease and ulcerative colitis.

The SNP may contribute to or define risk of a female-specific disorder selected from the group consisting of breast cancer, endometrial (uterus) cancer, endometriosis, gestational diabetes, intrahepatic cholestasis of pregnancy, neural tube defects, ovarian cancer, placental abruption, polycystic ovary syndrome, pre-eclampsia and uterine fibroids.

The SNP may contribute to or define risk of a genetic disease selected from the group consisting of acute intermittent porphyria, congenital erythropoietic porphyria (Gunther disease), cystic fibrosis, G6PD deficiency, haemochromatosis, haemophilia (F8, F9, F11), Huntington's disease, nonsyndromic deafness (congenital hearing loss), neurofibromatosis type II, polycystic kidney disease, sickle-cell anemia, Tay-Sachs disease, variegate porphyria and Wilson's disease.

The SNP may contribute to or define risk of a neurodegenerative disease selected from the group consisting of Alzheimer's Disease (AD), Amyotrophic Lateral Sclerosis (ALS), Creutzfeldt-Jakob Disease (CJD), Parkinson's Disease (PD), Primary Progressive Aphasia (PPA) and Progressive Supranuclear Palsy (PSP).

The SNP may contribute to or define risk of a neuro-psychological condition or disorder selected from the group consisting of attention deficit hyperactivity disorder (ADHD), Asperger's syndrome, autism, anxiety, bipolar disorder, depression, dyslexia, epilepsy, obsessive-compulsive disorder, schizophrenia and social phobia.

The SNP may contribute to or define risk of a neuro-psychological trait selected from the group consisting of emotional commitment, faithfulness, handedness, happiness, hyperactivity, intelligence/IQ, intelligence (learning from errors), intelligence (less cognitive decline with age), memory (verbal), memory (long-term: logical), memory (episodic), memory (traumatic), migratory behavior, novelty-seeking behavior, optimism, ruthlessness, sexual desire and sleeping time.

The SNP may contribute to or define risk of an addiction or substance dependence selected from the group consisting of addictive behaviors (gambling, alcoholism, smoking), alcoholism (alcohol cravings), alcoholism (alcohol dependence), alcoholism (withdrawal seizures), alcoholism (general), cannabis dependence, cocaine dependence, cocaine-induced paranoia, heroine dependence and nicotine dependence.

The SNP may contribute to or define risk of a disease or disorder selected from the group consisting of age-related macular degeneration, glaucoma, gout, hearing loss (noise-induced), hearing loss (age-related), hyperparathyroidism, hypothyroidism, Hirschprung's disease, osteoarthritis, osteoporosis, otitis, sarcoidosis, sciatica and Tourette's syndrome.

Accordingly, the method may alternatively be defined as a method of screening for susceptibility to disease disorder or trait by detecting a first allele of a SNP in a nucleic acid sequence: a method of diagnosing susceptibility to disease by detecting a first allele of a SNP in a nucleic acid sequence; and/or a method for prophylactically treating disease comprising detecting a first allele of a SNP in a nucleic acid sequence and prophylactically treating the disease when the first allele of the SNP is present.

When the nucleic acid is from a clinical sample, the SNP may contribute to or define disease progression. The disease may be any disease, the progression of which a SNP is known to contribute to or define, such as any disease described herein.

Accordingly, the method may alternatively be defined as a method of determining prognosis of a disease by detecting a first allele of a SNP in a nucleic acid sequence; and/or a method for treating a disease comprising determining prognosis by detecting a first allele of a SNP in a nucleic acid sequence, selecting a therapeutic agent and administering the therapeutic agent.

One embodiment of the invention provides a method for detecting a first allele of a single nucleotide polymorphism (SNP) in a nucleic acid sequence, wherein the method comprises (a) amplifying under isothermal conditions and stringent conditions a nucleic acid sequence from a sample, in a reaction mixture comprising
   (i) the nucleic acid sequence,
   (ii) a nucleic acid polymerase,
   (iii) a nucleoside triphosphate mixture,
   (iv) a forward inner primer targeting the first allele (FIPa1), comprising a F1c region which anneals to a F1 region of the nucleic acid sequence in the presence of the first allele and a F2 region which anneals to a F2c region of the nucleic acid sequence, region which anneals to a B1 region of the nucleic acid sequence in the presence of the first allele and a B2 region which anneals to a B2c region of the nucleic acid sequence,
   (vi) a forward blocking primer targeting a second allele of the SNP (FBa2), comprising a B1c region which anneals to a B1 region of the nucleic acid sequence in the presence of the second allele, and
   (vii) a backward blocking primer targeting the second allele (BBa2), comprising a F1c region which anneals to a F1 region of the nucleic acid sequence in the presence of the second allele, wherein the F1 region of the nucleic acid sequence and the B1 region of the nucleic acid sequence both contain the SNP, and wherein
   I. the SNP is the first to the third nucleotide from the 5' end of BBa2 and/or FBa2,
   II. the 3' end of BBa2 may be 1 to 8 nucleotides longer than the 3' end of the F1c region of FIPa1,
   III. the 3' end of FBa2 may be 1 to 8 nucleotides longer than the 3' end of the B1c region of BIPa1,
   IV. The concentration of FBa2 in the reaction mixture may be up to 3 times higher than the concentration of BIPa1, and/or
   V. The concentration of BBa2 in the reaction mixture may be up to 3 times higher than the concentration of FIPa1, and (b) detecting an amplified nucleic acid sequence, wherein the detection of an amplified nucleic acid sequence indicates the presence of the first allele of the SNP.

The method may further comprise a reciprocal reaction resulting in selective amplification of the second allele. The reciprocal reaction will involve use of (i) a forward inner primer targeting the second allele (FIPa2), comprising a F1c region which anneals to a F1 region of the nucleic acid sequence in the presence of the second allele and a F2 region which anneals to a F2c region of the nucleic acid sequence,
(ii) a backward inner primer targeting the second allele (BIPa2), comprising a B1c region which anneals to a B1 region of the nucleic acid sequence in the presence of the second allele and a B2 region which anneals to a B2c region of the nucleic acid sequence,
(iii) a forward blocking primer targeting the first allele of the SNP (FBa1), comprising a B1c region which anneals to a B1 region of the nucleic acid sequence in the presence of the first allele, and
(iv) a backward blocking primer targeting the first allele (BBa1), comprising a F1c region which anneals to a F1 region of the nucleic acid sequence in the presence of the first allele.

Accordingly, in the presence of the second allele, the annealing of FIPa2 and BIPa2 to the nucleic acid sequence may be more energetically favorable than the annealing of FBa1 and BBa1 to the nucleic acid sequence and in the presence of the first allele, the annealing of FIPa2 and BIPa2 to the nucleic acid sequence may be less energetically favorable than the annealing of FBa1 and BBa1 to the nucleic acid sequence, resulting in selective amplification of the second allele.

For example, the method may further comprise amplifying under isothermal conditions and stringent conditions a nucleic acid sequence from a sample, in a reaction mixture comprising
   (viii) the nucleic acid sequence,
   (ix) a nucleic acid polymerase,
   (x) a nucleoside triphosphate mixture,
   (xi) a forward inner primer targeting the second allele (FIPa2), comprising a F1c region which anneals to a F1 region of the nucleic acid sequence in the presence of the second allele and a F2 region which anneals to a F2c region of the nucleic acid sequence,
   (xii) a backward inner primer targeting the second allele (BIPa2), comprising a B1c region which anneals to a B1 region of the nucleic acid sequence in the presence of the second allele and a B2 region which anneals to a B2c region of the nucleic acid sequence, (xiii) a forward blocking primer targeting a first allele of the SNP (FBa1), comprising a B1c region which anneals to a B1 region of the nucleic acid sequence in the presence of the first allele, and (xiv) a backward blocking primer targeting the first allele (BBa1), comprising a F1c region which anneals to a F1 region of the nucleic acid sequence in the presence of the first allele, wherein the F1 region of the nucleic acid sequence and the B1 region of the nucleic acid sequence both contain the SNP.

The method may therefore further comprise detecting an amplified nucleic acid sequence, wherein the detection of an amplified nucleic acid sequence indicates the presence of the second allele of the SNP.

When the reciprocal reaction is performed, the reaction resulting in selective amplification of the first allele may be termed a "first reaction", while the reaction resulting in selective amplification of the second allele may be termed a "second reaction".

The nucleic acid sequence referred to in connection with the reciprocal reaction may be the same nucleic acid sequence as described above. Alternatively stated, the nucleic acid sequence referred to in connection with the second reaction may be the same nucleic acid sequence as referred to in connection with the first reaction. Therefore, the nucleic acid sequence may be referred to as "the nucleic acid sequence" throughout. It is however not necessary for the nucleic acid sequence to be the same single nucleic acid molecule. Typically, more than one nucleic acid molecule will be amplified in each of the first and second reactions. All of the nucleic acid molecules amplified in each of the first and second reactions may comprise the same sequence comprising the SNP.

The sample referred to in connection with the reciprocal reaction may be the same sample as described above. Alternatively stated, the sample referred to in connection with the second reaction may be the same sample referred to in connection with the first reaction. Therefore, the sample may be referred to as "the sample" throughout.

The features and/or functions of FIPa2, BIPa2, BBa1 and FBa1 in the reaction mixture for the reciprocal reaction may correspond mutatis mutandis to the features and/or functions described for FIPa1, BIPa1, BBa2 and FBa2 respectively in connection with the first reaction.

The reaction mixture for the reciprocal reaction may further comprise a forward outer primer (F3, also known as FOP) and/or a backward outer primer (B3, also known as BOP), as described above in connection with the first reaction.

The reaction mixture for the reciprocal reaction may further comprise a forward loop primer (LF) and/or a backward loop primer (LB), as described above in connection with the first reaction.

F3, B3, LF and/or LB for the second reaction may be the same as F3, B3, LF and/or LB for the first reaction. This is because F3, B3, LF and/or LB do not anneal to the nucleic acid the site of the SNP. Therefore, no modification of F3, B3, LF and/or LB is required for the second reaction. The F2 region of FIPa1 may be the same as the F2 region of FIPa2. The B2 region of BIPa1 may be the same as the B2 region of BIPa2.

For example, when the SNP is C580Y in the *Plasmodium falciparum* kelch 13 gene, the primer sequences may comprise one or more the following primer sequences (written in the 5' to 3' direction):

(i) FIPa1 may comprise (SEQ ID NO: 25)
TACATAGCTGATGATCTTATGATCATCGTATGAAAGCATG (ii) BIPa1 may comprise ATGTTGCTTTTGATAATAAAATTTATG CTAATAAGGCATATGGAAATTG (SEQ ID NO: 26)

(iii) FBa2 may comprise TGTGTTGCTTTTGATAATAAAATTTATG (SEQ ID NO: 27)

(iv) BBa2 may comprise CACACATAGCTGATGATCTAGGG (SEQ ID NO: 28)

(v) FIPa2 may comprise (SEQ ID NO: 29)
CACATAGCTGATGATCTTATGATCATCGTATGAAAGCATG (vi) BIPa2 may comprise GTGTTGCTTTTGATAATAAAATTTATG CTAATAAGGCATATGGAAATTG (SEQ ID NO: 30)

(vii) FBa1 may comprise GTATGTTGCTTTTGATAATAAAATTTATGTCATTG (SEQ ID NO: 31)

(viii) BBa1 may comprise ATACATAGCTGATGATCTAGGG (SEQ ID NO: 32)

(ix) F3 may comprise CTATTATACCGAATGTAGAAGCA (SEQ ID NO: 33)

(x) B3 may comprise TGCTCCTGAACTTCTAGC (SEQ ID NO: 34)

(xi) LF may comprise TCAAAGGTGCCACCTCTACC (SEQ ID NO: 35)

(xii) LB may comprise GGTGGAACTAATGGTGAGAGATTAA (SEQ ID NO: 36).

The above set of primer sequences are configured such that the first allele is 580Y (i.e. the "mutant" allele) and the second allele is 580C (i.e. the "wild type" allele).

For example, when the SNP is Y493H in the *Plasmodium falciparum* kelch 13 gene, the primer sequences may comprise one or more the following primer sequences (written in the 5' to 3' direction):

(i) FIPa1 may comprise (SEQ ID NO: 37)
GTAAGAAATTATTCAATACAGATTAGATATTAGTCAACAATGCTGG (ii) BIPa1 may comprise (SEQ ID NO: 38)
CACGTTTTTGGTGGTAAAAACGATCATACACCTCAGTT (iii) FBa2 may comprise ATACGTTTTTGGTGGTAATAACTAT (SEQ ID NO: 39)

(iv) BBa2 may comprise ATAAGAAATTATTCAATACAGCACTT (SEQ ID NO: 40)

(v) FIPa2 may comprise (SEQ ID NO: 41)
ATAAGAAATTATTCAATACAGATTAGATATTAGTCAACAATGCTGG (vi) BIPa2 may comprise (SEQ ID NO: 42)
TACGTTTTTGGTGGTAAAAACGATCATACACCTCAGTT (vii) FBa1 may comprise TACACGTTTTTGGTGGTAATAACTAT (SEQ ID NO: 43)

(viii) BBa1 may comprise TGTAAGAAATTATTCAATACAGCACTT (SEQ ID NO: 44)

(ix) F3 may comprise GGTGTAGAATATTTAAATTCGATGG (SEQ ID NO: 45)

(x) B3 may comprise TTGAAACATACCATACATCTCTT (SEQ ID NO: 46)

(xi) LF may comprise TGGTAGACATAGGTGTACACATACG (SEQ ID NO: 47)

(xii) LB may comprise ATTATAAGGCTTTATTTGA (SEQ ID NO: 48).

The above set of primer sequences are configured such that the first allele is 493H (i.e. the "mutant" allele) and the second allele is 493Y (i.e. the "wild type" allele).

For example, when the SNP is R539T in the *Plasmodium falciparum* kelch 13 gene, the primer sequences may comprise one or more the following primer sequences (written in the 5' to 3' direction):

(i) FIPa1 may comprise (SEQ ID NO: 49)
GTACCATTTGACGTAACACTAAGAGATGTATGGTATGTTTCAAG (ii) BIPa1 may comprise (SEQ ID NO: 50)
CAATTTATTGTATTGGGGGATCATATGCTTCTACATTCGGTAT (iii) FBa2 may comprise TAGAATTTATTGTATTGGGGGATAT (SEQ ID NO: 51)

(iv) BBa2 may comprise CTACCATTTGACGTAACACCAC (SEQ ID NO: 52)

(v) FIPa2 may comprise (SEQ ID NO: 53)
CTACCATTTGACGTAACTAAGAGATGTATGGTATGTTTCAAG (vi) BIPa2 may comprise (SEQ ID NO: 54)
AGAATTTATTGTATTGGGGGATCATATGCTTCTACATTCGGTAT (vii) FBa1 may comprise TACAATTTATTGTATTGGGGGATAT (SEQ ID NO: 55)

(viii) BBa1 may comprise TGTACCATTTGACGTAACACCAC (SEQ ID NO: 56)

(ix) F3 may comprise AACTGAGGTGTATGATCGTT (SEQ ID NO: 57)

(x) B3 may comprise ACCCATGCTTTCATACGA (SEQ ID NO: 58)

(xi) LF may comprise TTATTTCTTCTAGGTATATTT (SEQ ID NO: 59)

(xii) LB may comprise ATGATGGCTCTTCTATT (SEQ ID NO: 60).

The above set of primer sequences are configured such that the first allele is 539T (i.e. the "mutant" allele) and the second allele is 539R (i.e. the "wild type" allele).

The primers FIPa2, BIPa2, BBa1, FBa1, F3, B3, LF and/or LB may be stored as a primer mixture and may therefore be added to the reaction mixture together.

The reciprocal reaction may occur in a different reaction mixture or in the same reaction mixture (i.e. the reaction mixture defined above).

Both reactions may be detected in a single mixture using machine learning. Accordingly, when the first reaction mixture and the second reaction mixture the same reaction mixture, the detecting amplified nucleic acid sequences in the reaction mixture may be by a single fluorescent channel and machine learning may distinguish the amplified nucleic acid sequence that indicates the presence of the first allele of the SNP from the amplified nucleic acid sequence that indicates the presence of the second allele of the SNP. For example, the method may comprise a method of UK application no. 1809418.5 or International application no. PCT/EP2019/065039.

Relating to the field of Machine Learning, the method of UK application no. 1809418.5 or International application no. PCT/EP2019/065039 takes a multidimensional view, combining multiple features (e.g. linear features) in order to take advantage of, and improve on, information and principles behind existing methods to analyze real-time amplification data. The disclosed method involves two new concepts: the multidimensional standard curve and its 'home', the feature space. Together they expand the capabilities of standard curves, allowing for simultaneous absolute quantification, outlier detection and providing insights into amplification kinetics. This disclosure describes a general method which, for the first time, presents a multi-dimensional standard curve, increasing the degrees of freedom in data analysis and thereby being capable of uncovering trends and patterns in real-time amplification data obtained by existing qPCR instruments (such as the LightCycler 96 System from Roche Life Science). It is believed that this disclosure redefines the foundations of analyzing real-time nucleic acid amplification data and enables new applications in the field of nucleic acid research.

A method for use in quantifying a sample comprising a target nucleic acid is provided, the method comprising: obtaining a set of first real-time amplification data for each of a plurality of target concentrations: extracting a plurality of N features from the set of first data, wherein each feature relates the set of first data to the concentration of the target; and fitting a line to a plurality of points defined in an N-dimensional space by the features, each point relating to one of the plurality of target concentrations, wherein the line defines a multidimensional standard curve specific to the nucleic acid target which can be used for quantification of target concentration.

Optionally the method further comprises: obtaining second real-time amplification data relating to an unknown sample: extracting a corresponding plurality of N features from the second data; and calculating a distance measure between the line in N-dimensional space and a point defined in N-dimensional space by the corresponding plurality of N features. Optionally, the method further comprises computing a similarity measure between amplification curves from the distance measure, which can optionally be used to identify outliers or classify targets. Optionally each feature is different to each of the other features, and optionally wherein each feature is linearly related to the concentration of the target, and optionally wherein one or more of the features comprises one of $C_t$, $C_y$ and $-\log_{10}(F_0)$. Optionally the method further comprises mapping the line in N-dimensional space to a unidimensional function, $M_0$, which is related to target concentration, and optionally wherein the unidimensional function is linearly related to target concentration, and/or optionally wherein the unidimensional function defines a standard curve for quantifying target concentration. Optionally, the mapping is performed using a dimensionality reduction technique, and optionally wherein the dimensionality reduction technique comprises at least one of: principal component analysis: random sample consensus: partial-least squares regression; and projecting onto a single feature. Optionally, the mapping comprises applying a respective scalar feature weight to each of the features, and optionally wherein the respective feature weights are determined by an optimization algorithm which optimises an objective function, and optionally wherein the objective function is arranged for optimization of quantization performance. Optionally, calculating the distance measure comprises projecting the point in N-dimensional space onto a plane which is normal to the line in N-dimensional space, and optionally wherein calculating the distance measure further comprises calculating, based on the projected point, a Euclidean distance and/or a Mahalanobis distance. Optionally, the method further comprises calculating a similarity measure based on the distance measure, and optionally wherein calculating a similarity measure comprises applying a threshold to the similarity measure. Optionally, the method further comprises determining whether the point in N-dimensional space is an inlier or an outlier based on the similarity measure. Optionally, the method further comprises: if the point in N-dimensional space is determined to be an outlier then excluding the point from training data upon which the step of fitting a line to a plurality of points defined in N-dimensional space is based, and if the point in N-dimensional space is not determined to be an outlier then re-fitting the line in N-dimensional space based additionally on the point in N-dimensional space. Optionally, the method further comprises determining a target concentration based on the multidimensional standard curve, and optionally further based on the distance measure, and optionally when dependent on claim 4 based on the unidimensional function which defines the standard curve. Optionally, the method further includes displaying the target concentration on a display. Optionally, the method further comprises a step of fitting a curve to the set of first data, wherein the feature extraction is based on the curve-fitted first data, and optionally wherein the curve fitting is performed using one or more of a 5-parameter sigmoid, an exponential model, and linear interpolation. Optionally, the set of first data relating to the melting temperatures is pre-processed, and the curve fitting is carried out on the processed set of first data, and optionally wherein the pre-processing comprises one or more of: subtracting a baseline; and normalization. Optionally, the data relating to the melting temperature is derived from one or more physical measurements taken versus sample temperature, and optionally wherein the one or more physical measurements comprise fluorescence readings.

The use of machine learning enables single fluorescent channel (or single-well pH-based multiplexing) without the need of post-processing manipulations (such as melting curves, gels or sequencing) and enhances quantification. Multiplexing has the following advantages: More information with less sample: Higher throughput: cost effective (fewer dNTPs, enzymes, and other consumables): time saving: less input material required: more data from limited starting materials: increased accuracy of data normalization; fewer pipetting errors: reaction occurs in a closed environment (reduced risk of contamination).

The reciprocal reaction may occur in a different reaction mixture. Accordingly, the reaction mixtures may be termed a "first reaction mixture" and a "second reaction mixture". The first reaction may take place in the first reaction mixture, while the second reaction takes place in the second reaction mixture.

When the reciprocal reaction occurs in a different reaction mixture, the method may be defined as a method for detecting a first allele of a single nucleotide polymorphism (SNP) in a nucleic acid sequence and/or a second allele of the SNP in the nucleic acid sequence, wherein the method comprises (a) amplifying under isothermal conditions and stringent conditions a nucleic acid sequence from a sample, in a first reaction mixture comprising
  (i) the nucleic acid sequence,
  (ii) a nucleic acid polymerase,
  (iii) a nucleoside triphosphate mixture,
  (iv) a forward inner primer targeting the first allele (FIPa1), comprising a F1c region which anneals to a F1 region of the nucleic acid sequence in the presence of the first allele and a F2 region which anneals to a F2c region of the nucleic acid sequence,
  (v) a backward inner primer targeting the first allele (BIPa1), comprising a B1c region which anneals to a B1 region of the nucleic acid sequence in the presence of the first allele and a B2 region which anneals to a B2c region of the nucleic acid sequence,
  (vi) a forward blocking primer targeting the second allele (FBa2), comprising a B1c region which anneals to a B1 region of the nucleic acid sequence in the presence of the second allele, and
  (vii) a backward blocking primer targeting the second allele (BBa2), comprising a F1c region which anneals to a F1 region of the nucleic acid sequence in the presence of the second allele,
  wherein the F1 region of the nucleic acid sequence and the B1 region of the nucleic acid sequence both contain the SNP,
(b) detecting an amplified nucleic acid sequence in the first reaction mixture, wherein the detection of an amplified nucleic acid sequence indicates the presence the first allele of the SNP;
(c) amplifying under isothermal conditions and stringent conditions a nucleic acid sequence from a sample, in a second reaction mixture comprising
  (i) the nucleic acid sequence,
  (ii) a nucleic acid polymerase,
  (iii) a nucleoside triphosphate mixture,
  (iv) a forward inner primer targeting the second allele (FIPa2), comprising a F1c region which anneals to a F1 region of the nucleic acid sequence in the presence of the second allele and a F2 region which anneals to a F2c region of the nucleic acid sequence,
  (v) a backward inner primer targeting the second allele (BIPa2), comprising a B1c region which anneals to a B1 region of the nucleic acid sequence in the presence of the second allele and a B2 region which anneals to a B2c region of the nucleic acid sequence,
  (vi) a forward blocking primer targeting the first allele of the SNP (FBa1), comprising a B1c region which anneals to a B1 region of the nucleic acid sequence in the presence of the first allele, and
  (vii) a backward competitive blocking primer targeting the first allele (BBa1), comprising a F1c region which anneals to a F1 region of the nucleic acid sequence in the presence of the first allele, wherein the F1 region of the nucleic acid sequence and the B1 region of the nucleic acid sequence both contain the SNP, (d) detecting an amplified nucleic acid sequence in the second reaction mixture, wherein the detection of an amplified nucleic acid sequence indicates the presence of the second allele of the SNP.

The primers FIPa1, BIPa1, BBa2, FBa2, FIPa2, BIPa2, BBa1, FBa1, F3, B3, LF and/or LB may be stored as a primer mixture and may therefore be added to the reaction mixture together. The primers FIPa1, BIPa1, BBa2, FBa2, F3, B3, LF and/or LB may be stored as a primer mixture and may therefore be added to the reaction mixture together. The primers FIPa2, BIPa2, BBa1, FBa1, F3, B3, LF and/or LB may be stored as a primer mixture and may therefore be added to the reaction mixture together.

The method of the invention achieves high sensitivity, efficiency, specificity and rapidness (TTP<35 min) for the detection of single nucleotide polymorphisms at isothermal conditions suitable for PoC applications. For the first time here, judiciously designed sbLAMP primers for allele-specific amplification are combined with novel unmodified self-stabilizing (USS) primers specific to the SNP at their 5' end which robustly prevent unspecific sbLAMP amplification. The special design, based on the local GC % content at the SNP position enhanced allele specificity and the superior concentration of USS primers suppressed significantly non-target amplification offering an excellent linear working range with a limit of detection of $5\times10^1$ copies/reaction for the detection of two of the most important artemisinin-resistant SNPs C580Y and Y493H within about 30 and about 35 min, respectively.

This universal isothermal method for allele-specific primer design using chemically unmodified primers totally complementary to the target template except at the SNP position (either wild type or mutant allele) significantly reduces the cost of reagents and equipment avoiding the need of thermal cycling and electrophoresis for product validation. The guidelines disclosed herein enable development of USS-sbLAMP primer sets to detect any kind of SNP related to drug resistance, disease susceptibility or cancer development. Diagnostic platforms such as a CMOS-based ISFETs electrochemical biosensor based on nucleic acid amplification detection will perfectly couple with the USS-sbLAMP method described here. Any diagnostic device that can incorporate the proposed method will greatly expand the capability of rapid SNP screening at PoC, including limited resource settings (LRS) where infectious disease diagnosis and rapid drug resistance screening is urgently needed.

According to a second aspect, the invention provides a method for detecting drug resistance in an organism by detecting a first allele of a single nucleotide polymorphism (SNP) in a nucleic acid sequence, wherein the method comprises (a) amplifying under isothermal conditions and stringent conditions a nucleic acid sequence from a sample, in a reaction mixture comprising
   (i) the nucleic acid sequence,
   (ii) a nucleic acid polymerase,
   (iii) a nucleoside triphosphate mixture,
   (iv) a forward inner primer targeting the first allele (FIPa1), comprising a F1c region which anneals to a F1 region of the nucleic acid sequence in the presence of the first allele and a F2 region which anneals to a F2c region of the nucleic acid sequence,
   (v) a backward inner primer targeting the first allele (BIPa1), comprising a B1c region which anneals to a B1 region of the nucleic acid sequence in the presence of the first allele and a B2 region which anneals to a B2c region of the nucleic acid sequence,
   (vi) a forward blocking primer targeting a second allele of the SNP (FBa2), comprising a B1c region which anneals to a B1 region of the nucleic acid sequence in the presence of the second allele, and
   (vii) a backward blocking primer targeting the second allele (BBa2), comprising a F1c region which anneals to a F1 region of the nucleic acid sequence in the presence of the second allele,
   wherein the F1 region of the nucleic acid sequence and the B1 region of the nucleic acid sequence both contain the SNP, and
(b) detecting an amplified nucleic acid sequence, wherein the detection of an amplified nucleic acid sequence indicates the presence the first allele of the SNP.

The method for detecting drug resistance in an organism may therefore be defined as a method for detecting drug resistance in an organism, the method comprising detecting a first allele of a SNP in a nucleic acid sequence, comprising the method of the first aspect of the invention.

The SNP may define and/or contribute to drug resistance. The SNP may therefore be any SNP known in the art to define and/or contribute to drug resistance. According to a third aspect, the invention provides a method for the diagnosis of an infectious disease or a drug resistant infection by detecting a first allele of a single nucleotide polymorphism (SNP) in a nucleic acid sequence, wherein the method comprises (a) amplifying under isothermal conditions and stringent conditions a nucleic acid sequence from a sample, in a reaction mixture comprising
   (i) the nucleic acid sequence,
   (ii) a nucleic acid polymerase,
   (iii) a nucleoside triphosphate mixture,
   (iv) a forward inner primer targeting the first allele (FIPa1), comprising a F1c region which anneals to a F1 region of the nucleic acid sequence in the presence of the first allele and a F2 region which anneals to a F2c region of the nucleic acid sequence,
   (v) a backward inner primer targeting the first allele (BIPa1), comprising a B1c region which anneals to a B1 region of the nucleic acid sequence in the presence of the first allele and a B2 region which anneals to a B2c region of the nucleic acid sequence,
   (vi) a forward blocking primer targeting a second allele of the SNP (FBa2), comprising a B1c region which anneals to a B1 region of the nucleic acid sequence in the presence of the second allele, and
   (vii) a backward blocking primer targeting the second allele (BBa2), comprising a F1c region which anneals to a F1 region of the nucleic acid sequence in the presence of the second allele,
   wherein the F1 region of the nucleic acid sequence and the B1 region of the nucleic acid sequence both contain the SNP, and
(b) detecting an amplified nucleic acid sequence, wherein the detection of an amplified nucleic acid sequence indicates the presence the first allele of the SNP.

The method for the diagnosis of an infectious disease or a drug resistant infection may therefore be defined as a method for the diagnosis of an infectious disease or a drug resistant infection comprising detecting a first allele of a SNP in a nucleic acid sequence according to the method of the first aspect of the invention.

The first allele of a SNP may contribute to and/or define the infectious disease or the drug resistant infection.

The first allele of a SNP may be a biomarker for the infectious disease or the drug resistant infection. SNPs which are biomarkers for infectious diseases and drug resistant infections are known.

A "biomarker" is a naturally occurring molecule, gene, or characteristic by which a particular pathological or physiological process, disease, etc. can be identified. A biomarker may be a measurable indicator by which a particular pathological or physiological process, disease, etc. can be identified. Accordingly, a biomarker may be a measurable indicator of the presence of an infectious disease or drug resistant infection. The biomarker may increase or decrease in concentration in a sample when the infectious disease or drug resistant infection is present. For example, a first allele of a SNP may be present at a higher concentration when the sample is from a subject with an infectious disease or drug resistant infection than in a control sample. The relevant control sample may be from a different subject. Alternatively, the control sample may a different sample from the same subject, such as a sample from another location or time point. The other location may be, for example, a non-infected region or a different infected region of the same subject. The other time point may for example be an earlier or a later time point when the infectious disease or drug resistant infection was not present and/or not symptomatic.

The method may further comprise diagnosing an infectious disease or a drug resistant infection if the first allele of a SNP is present.

The method of diagnosis may be an in vitro method or an ex vivo method.

According to a fourth aspect, the invention provides a method for the treatment of an infectious disease or a drug resistant infection in a subject in need thereof, the method comprising detecting a first allele of a single nucleotide polymorphism (SNP) in a nucleic acid sequence, wherein the method comprises (a) amplifying under isothermal conditions and stringent conditions a nucleic acid sequence from a sample, in a reaction mixture comprising
  (i) the nucleic acid sequence,
  (ii) a nucleic acid polymerase,
  (iii) a nucleoside triphosphate mixture,
  (iv) a forward inner primer targeting the first allele (FIPa1), comprising a F1c region which anneals to a F1 region of the nucleic acid sequence in the presence of the first allele and a F2 region which anneals to a F2c region of the nucleic acid sequence, region which anneals to a B1 region of the nucleic acid sequence in the presence of the first allele and a B2 region which anneals to a B2c region of the nucleic acid sequence,
  (vi) a forward blocking primer targeting a second allele of the SNP (FBa2), comprising a B1c region which anneals to a B1 region of the nucleic acid sequence in the presence of the second allele, and
  (vii) a backward blocking primer targeting the second allele (BBa2), comprising a F1c region which anneals to a F1 region of the nucleic acid sequence in the presence of the second allele,
  wherein the F1 region of the nucleic acid sequence and the B1 region of the nucleic acid sequence both contain the SNP, and
(b) detecting an amplified nucleic acid sequence, wherein the detection of an amplified nucleic acid sequence indicates the presence the first allele of the SNP, and
(c) administering a drug to the subject in need thereof.

The method for the treatment of an infectious disease or a drug resistant infection may therefore be defined as a method for the treatment of an infectious disease or a drug resistant infection in a subject in need thereof, the method comprising detecting a first allele of a SNP in a nucleic acid sequence according to the method of the first aspect of the invention, further comprising administering a drug to the subject in need thereof.

The method for treatment of an infectious disease or a drug resistant infection may also be defined as a method for the treatment of a drug resistant infection in a subject in need thereof, the method comprising diagnosing a drug resistant infection according the method of the third aspect of the invention, further comprising administering a drug to the subject in need thereof.

Treating the infectious disease or drug resistant infection may comprise administration of a therapeutic agent. The therapeutic agent may be an alternative therapeutic agent, for example a therapeutic agent to which the infection is not resistant. The therapeutic agent may be selected by a medical practitioner on the basis that resistance to the therapeutic agent is not associated with, contributed to and/or defined by the first allele of the SNP.

For example, when the drug resistant infection is an artemisinin resistant infection, for instance when the SNP is a mutation in the *Plasmodium falciparum* kelch 13 gene, then the therapeutic agent may be a non-artemisinin therapeutic agent. For example, when the SNP is e C580Y in the *Plasmodium falciparum* kelch 13 gene: F446I in the *Plasmodium falciparum* kelch 13 gene: Y493H in the *Plasmodium falciparum* kelch 13 gene: R539T in the *Plasmodium falciparum* kelch 13 gene: 1543T in the *Plasmodium falciparum* kelch 13 gene; or P553L in the *Plasmodium falciparum* kelch 13 gene, the therapeutic agent may be a non-artemisinin therapeutic agent. Examples of non-azole therapeutic agents that can be used to treat a *Plasmodium* infection include artesunate-mefloquine, DHA-piperaquine, artesunate-pyronaridine, arterolane-piperquine, triple artemisinin combination therapies such as dihydroartemisinin-piperaquine-mefloquine and artemether-lumefantrine-amodiaquine instead of double artemisinin combinations. Drug rotation may also be used.

The infectious disease may be caused by one or more pathogenic microorganisms, such as bacteria, viruses, parasites or fungi. Infectious diseases can be spread, directly or indirectly, from one person to another. The infectious disease may be a zoonotic diseases, which is an infectious diseases of animals that can cause disease when transmitted to humans.

The infectious disease may be selected from the group consisting of Acute Flaccid Myelitis (AFM), Anaplasmosis, *Anthrax*, Babesiosis, Botulism, Brucellosis, *Burkholderia mallei* (Glanders), *Burkholderia pseudomallei* (Melioidosis), Campylobacteriosis (*Campylobacter*), Carbapenem-resistant Infection (CRE/CRPA), Chancroid, Chikungunya Virus Infection (Chikungunya), *Chlamydia*, Ciguatera, *Clostridium Difficile* Infection, *Clostridium Perfringens* (Epsilon Toxin), Coccidioidomycosis fungal infection (Valley fever), Creutzfeldt-Jacob Disease, transmissible spongiform encephalopathy (CJD), Cryptosporidiosis (Crypto), Cyclosporiasis, Dengue, 1,2,3,4 (Dengue Fever), Diphtheria, *E. coli* infection (*E. coli*), Eastern Equine Encephalitis (EEE), Ebola, Hemorrhagic Fever (Ebola), Ehrlichiosis, Encephalitis, Arboviral or parainfectious, Enterovirus Infection, Non-Polio (Non-Polio Enterovirus), Enterovirus Infection, D68 (EV-D68), Giardiasis (Giardia), Gonococcal Infection (Gonorrhea), Granuloma inguinale, Haemophilus Influenza disease, Type B (Hib or H-flu), Hantavirus Pulmonary Syndrome (HPS), Hemolytic Uremic Syndrome (HUS), Hepatitis A (Hep A), Hepatitis B (Hep B), Hepatitis C (Hep C), Hepatitis D (Hep D), Hepatitis E (Hep E), Herpes, Herpes Zoster, zoster VZV (Shingles), Histoplasmosis infection (Histoplasmosis), Human Immunodeficiency Virus/AIDS (HIV/AIDS), Human Papillomarivus (HPV), Influenza (Flu), Legionellosis (Legionnaires Disease), Leprosy (Hansens Disease), Leptospirosis, Listeriosis (*Listeria*), Lyme Disease, Lymphogranuloma venereum infection (LVG), Malaria, Measles, Meningitis, Viral (Meningitis, viral), Meningococcal Disease, Bacterial (Meningitis, bacterial), Middle East Respiratory Syndrome Coronavirus (MERS-COV), Mumps, Norovirus, Paralytic Shellfish Poisoning (Paralytic Shellfish Poisoning, Ciguatera), Pediculosis (Lice, Head and Body Lice), Pelvic Inflammatory Disease (PID), Pertussis (Whooping Cough), Plague: Bubonic, Septicemic, Pneumonic (Plague), Pneumococcal Disease (Pneumonia), Poliomyelitis (Polio), Powassan, Psittacosis, Pthiriasis (Crabs: Pubic Lice Infestation), Pustular Rash diseases (Small pox, monkeypox, cowpox), Q-Fever, Rabies, Ricin Poisoning, Rickettsiosis (Rocky Mountain Spotted Fever), Rubella, Including congenital (German Measles), *Salmonellosis* gastroenteritis (*Salmonella*), Scabies Infestation (Scabies), Scombroid, Severe Acute Respiratory Syndrome (SARS), Shigellosis gastroenteritis (*Shigella*), Smallpox, Staphyloccal Infection, Methicillin-resistant (MRSA), Staphylococcal Food Poisoning, Enterotoxin-B Poisoning (Staph Food Poisoning), Staphylococcal Infection, Vancomycin Intermediate (VISA), Staphylococcal Infection, Vancomycin Resistant (VRSA), Streptococcal Disease, Group A (invasive) (Strep A), Streptococcal Disease, Group B (Strep-B), Streptococcal Toxic-Shock Syndrome, STSS, Toxic Shock (STSS, TSS), Syphilis, primary, secondary, early latent, late latent, congenital, Tetanus Infection, tetani (Lock Jaw), Trichonosis Infection (Trichinosis), Tuberculosis (TB), Tuberculosis (Latent) (LTBI), Tularemia (Rabbit fever), Typhoid Fever, Group D, Typhus, Vaginosis, bacterial (Yeast Infection), Varicella (Chickenpox), *Vibrio cholerae* (Cholera), Vibriosis (*Vibrio*), Viral Hemorrhagic Fever (Ebola, Lassa, Marburg), West Nile Virus, Yellow Fever, Yersenia (*Yersinia*) and Zika Virus Infection (Zika).

The first allele of the SNP may be a biomarker for the infectious disease. SNPs which are biomarkers for infectious diseases are known.

The invention further provides a method for point-of-care diagnosis of an infectious disease by detecting a first allele of a single nucleotide polymorphism (SNP) in a nucleic acid sequence, wherein the method comprises (a) amplifying under isothermal conditions and stringent conditions a nucleic acid sequence from a sample, in a reaction mixture comprising
   (i) the nucleic acid sequence,
   (ii) a nucleic acid polymerase,
   (iii) a nucleoside triphosphate mixture,
   (iv) a forward inner primer targeting the first allele (FIPa1), comprising a F1c region which anneals to a F1 region of the nucleic acid sequence in the presence of the first allele and a F2 region which anneals to a F2c region of the nucleic acid sequence,
   (v) region which anneals to a B1 region of the nucleic acid sequence in the presence of the first allele and a B2 region which anneals to a B2c region of the nucleic acid sequence,
   (vi) a forward blocking primer targeting a second allele of the SNP (FBa2), comprising a B1c region which anneals to a B1 region of the nucleic acid sequence in the presence of the second allele, and
   (vii) a backward blocking primer targeting the second allele (BBa2), comprising a F1c region which anneals to a F1 region of the nucleic acid sequence in the presence of the second allele,
   wherein the F1 region of the nucleic acid sequence and the B1 region of the nucleic acid sequence both contain the SNP, and
(b) detecting an amplified nucleic acid sequence, wherein the detection of an amplified nucleic acid sequence indicates the presence the first allele of the SNP.

The method for point-of-care diagnosis of an infectious disease may optionally further comprise diagnosing an infectious disease if the first allele of the SNP is present.

The method for point-of-care diagnosis of an infectious disease may therefore be defined as a method for point-of-care diagnosis of an infectious disease by detecting a first allele of a SNP in a nucleic acid sequence, comprising the method of the first aspect of the invention, further comprising diagnosing an infectious disease if the first allele of the SNP is present.

According to a fifth aspect, the invention provides a kit comprising (i) a forward inner primer targeting the first allele (FIPa1), comprising a F1c region which anneals to a F1 region of a nucleic acid sequence in the presence of the first allele of a single nucleotide polymorphism (SNP) in the nucleic acid sequence and a F2 region which anneals to a F2c region of the nucleic acid sequence,
(ii) a backward inner primer targeting the first allele (BIPa1), comprising a B1c region which anneals to a B1 region of the nucleic acid sequence in the presence of the first allele and a B2 region which anneals to a B2c region of the nucleic acid sequence,
(iii) a forward blocking primer targeting a second allele of the SNP (FBa2), comprising a B1c region which anneals to a B1 region of the nucleic acid sequence in the presence of the second allele, and
(iv) a backward blocking primer targeting the second allele (BBa2), comprising a F1c region which anneals to a F1 region of the nucleic acid sequence in the presence of the second allele, wherein the F1 region of the nucleic acid sequence and the B1 region of the nucleic acid sequence both contain the SNP.

As used herein, a “kit” is a packaged combination optionally including instructions for use of the combination and/or other reactions and components for such use.

The kit may further comprise a forward outer primer (F3) and/or a backward outer primer (B3).

The kit may further comprise a forward loop primer (LF) and/or a backward loop primer (LB).

The kit may further comprise:

(v) a forward inner primer targeting the second allele (FIPa2), comprising a F1c region which anneals to a F1 region of the nucleic acid sequence in the presence of the second allele and a F2 region which anneals to a F2c region of the nucleic acid sequence,
(vi) a backward inner primer targeting the second allele (BIPa2), comprising a B1c region which anneals to a B1 region of the nucleic acid sequence in the presence of the second allele and a B2 region which anneals to a B2c region of the nucleic acid sequence,
(vii) a forward blocking primer targeting the first allele of the SNP (FBa1), comprising a B1c region which anneals to a B1 region of the nucleic acid sequence in the presence of the first allele, and (viii) a backward blocking primer targeting the first allele (BBa1).

FIPa2, BIPa2, BBa1, FBa1, F3, B3, LF, LB, FIPa1, BIPa1, BBa2 and/or FBa2 may be as defined elsewhere herein.

The kit may further comprise a nucleic acid polymerase and/or a nucleoside triphosphate mixture.

Any of the kit components defined above may be combined in any combination.

According to a seventh aspect, the invention provides a reaction mixture comprising the components of the kit according to the sixth aspect of the invention in a liquid medium.

The invention also provides a use of the kit according to the sixth aspect of the invention or of the reaction mixture according to the seventh aspect of the invention in the detection of a pathogen.

Preferred features for the second and subsequent aspects of the invention are as for the first aspect of the invention mutatis mutandis.

EXAMPLES

The present invention will now be described by way of reference to the following Examples and accompanying Drawings which are present for the purposes of illustration only and are not to be construed as being limiting on the invention.

Example 1—USS-sbLAMP Specific to SNP C580Y and SNP Y493H Primer Design of USS-sbLAMP Specific to SNP C580Y and SNP Y493H The USS-sbLAMP method consists of a total of eight primers targeting ten distinct regions of the DNA template. The sbLAMP primer set is composed of two outer primers (F3 and B3), two loop primers (LF and LB) and two inner primers (sbFIP and sbBIP), where F1c and B1c locate the SNP at their 5' end. The USS primer set consists of a forward blocking competitive primer (FB) and a backward blocking competitive primer (BB).

The USS-sbLAMP primer sets for the specific detection of C580Y and Y493H were designed based on the gene K13 of *P. falciparum*. Consensus reference genomic sequences from all human-infective *Plasmodium* species (PF3D7_1343700.1, PFIT_1342900, PKNH_1257700, PKNOH_S09541100, PVP01_1211100, PVX_083080, PmUG01_12021200, POcGH01_12019400) were retrieved from *Plasmodium* Genomic Resource (PlasmoDB and aligned using MUSCLE algorithm (Edgar et al. *Nucleic Acids Res.* 32, 1792-1797 (2004)) in Geneious 10.0.5 software (Kearse et al. *Bioinformatics* 28, 1647-1649 (2012)).[35]. The sbLAMP primer set was designed using Primer Explorer V5 (Eiken Chemical Co. Ltd., Tokyo, Japan; Line 20: primerexplorer.jp/lampv5e/index and optimized manually to locate the SNP at the 5' end of F1c and B1c following the method described by Eiken Chemical Co., Ltd. (Eiken Genome Site. (2005). Available at: Line 23: loopamp.eiken-.co.jp/e/lamp/snpsindex.) with the novelty of considering the local GC % composition for the design of FIP and BIP primers, named as sbFIP and sbBIP. Different lengths of F1c and B1c were designed for the SNP C580Y (17 bp, 19 bp, 21 bp and 25 bp for F1c, and 21 bp, 25 bp, 27 bp and 29 bp for B1c) and for the SNP Y493H (21 bp for F1c and 17 bp for B1c). The USS primer sets were designed based on the most suitable pair of F1c and B1c for allele-specific amplification based on experimental data (see Results and Discussion). FB and BB primers of different lengths were manually designed, always equal 5 or longer than the selected F1c and B1c. They were between 0-6 bp longer at the 3' end, and locate the SNP within the 3 bp closer to their 5' end (FB0, FB1, FB2 and BB0, BB1 and BB2) where the number indicates the position of the SNP from the 5' end. In order to investigate the performance of the self-stabilizing primers, reverse-complementary primers to FB/BB, named FA/BA, were designed, and 3' end modifications (/3AmMo/) were added to each primer set, named FA*/BA* and FB*/BB*. Sequences of final USS-sbLAMP primer sets are provided in Table 3.

TABLE 3

USS-sbLAMP primer sequences for allele-specific amplification of SNP C580Y and SNP Y493H. Amplicon length (between F3 and B3) of SNP C580Y is 230 bp and of SNP Y493H is 208 bp.

| Primer ID | Sequence (5'-3') | Primer ID | Sequence (5'-3') |
|---|---|---|---|
| C580Y_F3 | CTATTATACCGAATGTAGAAGCA (SEQ ID NO: 61) | Y493H_F3 | GGTGTAGAATATTTAAATTCGATGG (SEQ ID NO: 73) |
| C580Y_B3 | TGCTCCTGAACTTCTAGC (SEQ ID NO: 62) | Y493H_B3 | TTGAAACATACCATACATCTCTT (SEQ ID NO: 74) |
| C580Y_LF | TCAAAGGTGCCACCTCTACC (SEQ ID NO: 63) | Y493H_LF | TGGTAGACATAGGTGTACACATACG (SEQ ID NO: 75) |
| C580Y_LB | GGTGGAACTAATGGTGAGAGATTAA (SEQ ID NO: 64) | Y493H_LB | ATTATAAGGCTTTATTTGA (SEQ ID NO: 76) |
| C580Y_sbFIP17_WT | CACATAGCTGATGATCTTATGATCATCGTA TGAAAGCATG (SEQ ID NO: 65) | Y493H_sbF1P21_WT | ATAAGAAATTATTCAATACAGATTAGATA TTAGTCAACAATGCTGG (SEQ ID NO: 77) |
| C580Y_sbBIP27_WT | GTGTTGCTTTTGATAATAAAATTTATG CTAATAAGGCATATGGAAATTG (SEQ ID NO: 66) | Y493H_sbB1P17_WT | TACGTTTTTGGTGGTAAAAACGATCATAC ACCTCAGTT (SEQ ID NO: 78) |
| C580Y_sbFIP17_MT | TACATAGCTGATGATCTTATGATCATCGTAT GAAAGCATG (SEQ ID NO: 67) | Y493H_sbF1P21_MT | GTAAGAAATTATTCAATACAGATTAGATA TTAGTCAACAATGCTGG (SEQ ID NO: 79) |

TABLE 3-continued

USS-sbLAMP primer sequences for allele-specific amplification of SNP C580Y and SNP Y493H. Amplicon length (between F3 and B3) of SNP C580Y is 230 bp and of SNP Y493H is 208 bp.

| Primer ID | Sequence (5'-3') | Primer ID | Sequence (5'-3') |
|---|---|---|---|
| C580Y_sbBIP27_MT | ATGTTGCTTTTGATAATAAAATTTATG CTAATAAGGCATATGGAAATTG (SEQ ID NO: 68) | Y493H_sbB1P17_MT | CACGTTTTTGGTGGTAAAAACGATCATA CACCTCAGTT (SEQ ID NO: 80) |
| C580Y_FB233_MT | GTATGTTGCTTTTGATAATAAAATTTATGTC ATTG (SEQ ID NO: 69) | Y493H_FB224_MT | TACACGTTTTTGGTGGTAATAACTAT (SEQ ID NO: 81) |
| C580Y_BB121_MT | ATACATAGCTGATGATCTAGGG (SEQ ID NO: 70) | Y493H_BB126_MT | TGTAAGAAATTATTCAATACAGCACTT (SEQ ID NO: 82) |
| C580Y_FB127_WT | TGTGTTGCTTTTGATAATAAAATTTATG (SEQ ID NO: 71) | Y493H_FB124_WT | ATACGTTTTTGGTGGTAATAACTAT (SEQ ID NO: 83) |
| C580Y_BB221_WT | CACACATAGCTGATGATCTAGGG (SEQ ID NO: 72) | Y493H_BB026_WT | ATAAGAAATTATTCAATACAGCACTT (SEQ ID NO: 84) |

USS-sbLAMP Mechanism.

The incorporation of USS primers in the sbLAMP reaction enhance allele discrimination by preventing unspecific sbLAMP amplification, through thermodynamically favored hybridization. USS primers and sbFIP/sbBIP primers (within sbLAMP) are in the same reaction mixture but always targeting different alleles, one set specific to the WT allele and the other to the MT allele. Allelic discrimination is possible by comparing the outcome of two independent reactions: WT specific reaction ($sbLAMP_{WT}$ and $USS_{MT}$ primers) and MT specific reaction ($sbLAMP_{MT}$ and $USS_{WT}$ primers) as shown in FIG. 1. sbLAMP follows the LAMP method described by Notomi et al. (Notomi, T. et al. *Nucleic Acids Res.* 28, E63 (2000)) It is initiated by the binding of two inner primers sbFIP (F1c-F2) and sbBIP (B1c-B2), which bind to F2c and B2c regions respectively, leaving F1c and B1c free. Two outer primers F3 and B3 displace the strands releasing single stranded DNA (ssDNA). The free F1c and B1c form a dumbbell-like structure by annealing to their complementary sequences F1 and B1 respectively. It is rapidly linearized from its 3' end, and the binding of sbFIP and sbBIP initiate the cyclic amplification step. During this step, LF and LB primers bind their complementary sequences which are in between B1c-B2c and F1-F2 further accelerating the reaction Nagamine et al. *Mol. Cell. Probes* 16, 223-229 (2002). In the end, stem-loop DNA and cauliflower-like structures are obtained. The complementarity of the USS primers to the target template (with SNP specificity) suggests their possible hybridization during the initiation stage of sbLAMP, causing a general delay in specific and unspecific reactions until USS primers are displaced by F3/B3 and sbFIP/sbBIP (F2 and B2 specifically). At the end of the initiation stage, the annealing of the USS primers to the template, and the formation of the dumbbell-like structure with the binding of sbFIP and sbBIP cannot occur simultaneously. Consequently, there will be a competition and the most energetically favorable reaction, the specific reaction, will occur at a first stage. In case the DNA template is specific to the sequence of the USS primers, a second stage will take place. The association between the USS primers and the template (FB will anneal to the B1 region of the dumbbell-like structure preventing the annealing between B1 and B1c regions of this structure and the annealing of B2 of the BIP primer to the B2c region of the dumbbell-like structure: BB will anneal to the F1 region of the dumbbell-like structure preventing the annealing between F1 and F1c regions of this structure and the annealing of F2 of the FIP primer to the F2c region of the dumbbell-like structure) is not transient and a highly stable primer-template complex is formed as nucleotides are incorporated by the DNA polymerase. This self-stabilizing behavior will create by-products that do not prime amplification and, therefore, will inhibit the formation of dumbbell-like structures preventing unspecific amplification. The hybridization energies of specific FB/BB must be favorable with respect to the energies of unspecific F1c/B1c, $\Delta G^{\circ}_{(F1c/B1c)} > \Delta G^{\circ}_{(FB/BB)}$. To achieve that, the design of USS primers followed two principles: primer elongation along the 3' end, and displacement of the position of the SNP from their 5' end. Regarding the first principle, FB/BB primers should be equal or longer than F1c/B1c. Some overlapping with the 5' end of LF and LB is tolerated since their annealing do not interfere with the binding of FB/BB. Due to the fact that USS primers should not delay the time to positive (TTP), their free energy values should not exceed in more than 10 kcal mol-1 the free energy values of F1c/B1c. Regarding the second principle, placing the SNP slightly away from the 5' end of USS primers might enhance their specificity due to the fact that a local region around the SNP will be opened or closed based on their complementarity at the SNP position. Depending on the sequence of the target, placing the SNP at their 5' end could be the most optimum configuration.

Thermodynamic Calculations of USS-sbLAMP Primers.

Possible secondary structures, primer dimer formation and hybridization stability were checked using NUPACK and NetPrimer (Premier Biosoft, NetPrimer; premierbiosoft.com/netprimer). The stability of the primers at the corresponding temperature (63° C.=336.15 K) was calculated by the Gibbs free energy (ΔG°) equation (Equation 1) using the thermodynamic nearest neighbor parameters for Watson-Crick base pairs:

$$\Delta G^{\circ}_{T} = \Delta H^{\circ} - T\Delta S^{\circ} \quad (1)$$

where T is in Kelvin, ΔG° in kcal $mol^{-1}$, ΔH° in kcal $mol^{-1}$ and ΔS° in kcal $K^{-1}$ $mol^{-1}$. ΔG° of the hybridization between primer and template was calculated using the software NetPrimer introducing the primer of interest, and the template as $DNA_{TEMPLATE} = CDNA_{primer} + 1_{5'} + 1_{3'}$ where $1_{5'}$ and $1_{3'}$ mean the addition of one complementary nucleotide at the 3' end and at the 5' end of the $cDNA_{primer}$, respectively. In order to adjust the entropy (ΔS°) to the corresponding salt conditions Equation 2 was used, where $Na^+$ is the concentration of monovalent cations in M and N is the number of nucleotide pairs in the primer. $T_m$ in ° C. was calculated by Equation 3, applying the conversion factor −273.15. R is the gas constant $1.9872\times10^{-3}$ kcal $K^{-1}$ $mol^{-1}$, $C_T$ is the total molar concentration of the strands in M and x is considered 4 for nonself-complementary duplexes.

$$\Delta S°[Na^+] = \Delta S° = [1\ M_{NaCl}] + 0.368\ N\ln[Na^+] \quad (2)$$

$$T_m = \frac{\Delta H}{\Delta S° + R\ln\left(\frac{C_T}{x}\right)} - 273.15 \quad (3)$$

Samples and DNA Extraction Methods.

Two gBlock Gene fragments of 607 bp were purchased from Integrated DNA Technologies and resuspended in TE buffer to 10 ng/μL stock solutions (stored at −20° C.). The WT synthetic DNA template (named here as WT template) contained SNPs 580C and 493Y: the MT synthetic DNA template (named here as MT template) contained the corresponding drug-resistant mutations, 580Y and 493H. *P. falciparum* genomic DNA (gDNA) was isolated using the PureLink Genomic DNA Mini Kit (ThermoFisher Scientific) from asexual cultures of Cambodian and Thai culture adapted parasites harboring the WT K13 allele (ANL1 and ARN1G, respectively), a Thai isolate harbouring K13 539T mutation (APS2G) and a Cambodian isolate harboring K13 580Y (ANL5G). *P. ovale* curtisi, *P. ovale* wallikeri, *P. vivax, P. malariae* and *P. knowlesi* clinical isolates (gDNA) were kindly provided by Prof. Colin Sutherland. The samples were stored at −20° C. until experiments were performed.

USS-sbLAMP Reaction Conditions.

Two independent reactions, WT specific reaction and MT specific reaction, were performed with each target. Each reaction mixture contained the following: 1.5 μL of 10× isothermal buffer, 0.9 μL of $MgSO_4$ (100 mM stock), 2.1 μL of dNTPs (10 mM stock), 0.375 μL of BSA (20 mg/mL stock), 2.4 μL of Betaine (5M stock), 0.375 μL of SYTO® 9 Green (20 μM stock), 0.6 μL of Bst 2.0 DNA polymerase (8,000 U/mL stock), 3 μL of different concentrations of synthetic DNA or gDNA, 1.5 μL of 10× sbLAMP primer mixture (20 μM of sbBIP/sbFIP, 10 μM of LF/LB, and 2.5 μM B3/F3) and enough nuclease-free water (ThermoFisher Scientific) to bring the volume to 15 μL. All reagents were purchased to New England BioLabs and all synthetic DNA to Integrated DNA Technologies. Reactions were performed at 63° C. for 50 min for screening purposes and 30-35 min for final assays. One melting cycle was performed at 95° C. for 10 s, 65° C. for 60 s and 97° C. for 1 s for validation of the specificity of the products. Experiments were performed twice and each condition was run in triplicates (5 μL each reaction) loading the reactions into LightCycler® 480 Multiwell Plates 96 (Roche Diagnostics) utilizing a LightCycler® 96 Real-Time PCR System (Roche Diagnostics). USS-sbLAMP was performed by incorporating into the sbLAMP 10× primer mixture, the USS primers (FA/BA, FA*/BA*, FB/BB or FB*/BB*) at different concentrations: 1 μM, 1.5 μM, 2 μM, 2.5 μM, 3 μM, 3.5 μM, 4 μM and 4.5 μM. Nuclease-free water was adjusted to bring the volume to 15 μL. sbLAMP and USS primers were purchased from Integrated DNA Technologies and resuspended in nuclease-free water to 100 μM and 400 μM stock solutions, respectively. The solutions were stored at 4° C.

Sensitivity of USS-sbLAMP Method.

Sensitivity was evaluated using ten-fold serial dilutions of synthetic DNA into nuclease-free water: $5\times10^4$, $5\times10^3$, $5\times10^2$ and $5\times10^1$ copies/μL. Standard curves were generated by plotting the TTP against copies/reaction with errors at one standard deviation.

Cross-Reactivity of USS-sbLAMP Method and Detection of Clinical Isolates.

Ten clinical isolates (gDNA) were used to evaluate the feasibility of USS-sbLAMP and to prove the absence of cross-reactivity with any other human-infective *Plasmodium* species. Samples included: *P. ovale* curtisi. *P. ovale* wallikeri. *P. vivax. P. malariae, P. knowlesi* (2 samples), *P. falciparum* harboring WT K13 alleles (2 samples), *P. falciparum* harboring the MT 580Y allele and *P. falciparum* harboring the MT 539T allele. Experiments were performed as described above.

Statistical Analysis.

Data is presented as mean TTP±standard deviation; p-values were calculated by Student's heteroscedastic t-Test, with a two-sided distribution. Statistically significant difference was considered as *p-value<0.05, p-value<0.01, *p-value<0.001, ****p-value<0.0001: k− means cluster analysis and ANOVA test was performed in Origin software (OriginLab, Northampton, MA).

sbLAMP Method.

Different lengths of F1c and B1c were designed in order to study the impact of local GC % content, $T_m$ and primer length in: (i) allele-specificity, and (ii) TTP. The design of overlapping primers for allele detection is not trivial, and the dissimilarity of the sequence in terms of ACTG composition upstream and downstream the position of the SNP should be taken into account. In general, primers are equal in length (23-24 bp) and are considered specific and stable as long as they present optimal % GC content and $T_m$ to anneal to the DNA template. Due to the fact that the GC % content and $T_m$ are different at local regions with respect to the position of the SNP, allele-specific primers sbFIP and sbBIP might be of different lengths. F1c and B1c of four different lengths each were designed with hybridisation hybridization energies considered between −10.00 kcal $mol^{-1}$ and −23.00 kcal $mol^{-1}$, increasing proportionally to the length of the primers and the GC %. Real-time amplification experiments of WT (FIG. 2A) and MT (FIG. 2B) templates were performed independently. Two independent reactions, WT specific ($sbLAMP_{WT}$), and MT specific ($sbLAMP_{MT}$) were tested with each template. A total of 16 combinations of F1c-B1c were performed: F1c of 17, 19, 21 and 25 bp, and B1c of 21, 25, 27 and 29 bp. For both DNA templates, the TTP of specific and unspecific reactions was reduced as B1c was elongated 0 from 21 bp to 29 bp, and allele-specific detection was enhanced as F1c was shortened from 25 bp to 17 bp.

The amplification time difference ($C_t$) between specific and unspecific reactions with each template is presented in Table 4. Average $C_t$ values of specific reactions below 20 min are single underlined. $\Delta C_t$ values above 2 min are in italics. Average of two experiments performed in triplicates using $5\times10^4$ cp/rxn of synthetic DNA. Selected sbLAMP primer sets are indicated with arrows in the plots and double underlined cells.

TABLE 4

| ($\Delta C_t$) between specific and unspecific reactions | | | | | |
|---|---|---|---|---|---|
| | | F1c | | | |
| Allele | B1c | 17 bp | 19 bp | 21 bp | 25 bp |
| WT 580C | 21 bp | 16.48 | 13.99 | 12.43 | 9.56 |
| | 25 bp | 10.66 | 9.32 | 6.82 | 5.48 |
| | 27 bp | 4.18 | 3.37 | 2.42 | 2.32 |
| | 29 bp | 3.34 | 2.77 | 1.96 | 1.71 |
| MT 580Y | 21 bp | 10.9 | 12.16 | 9.06 | 5.87 |
| | 25 bp | 14.15 | 9.14 | 5.14 | 4.98 |
| | 27 bp | 2.29 | 0.42 | 0.07 | 0.52 |
| | 29 bp | 1.07 | 0.38 | 0.14 | 0.08 |

Figure 2:
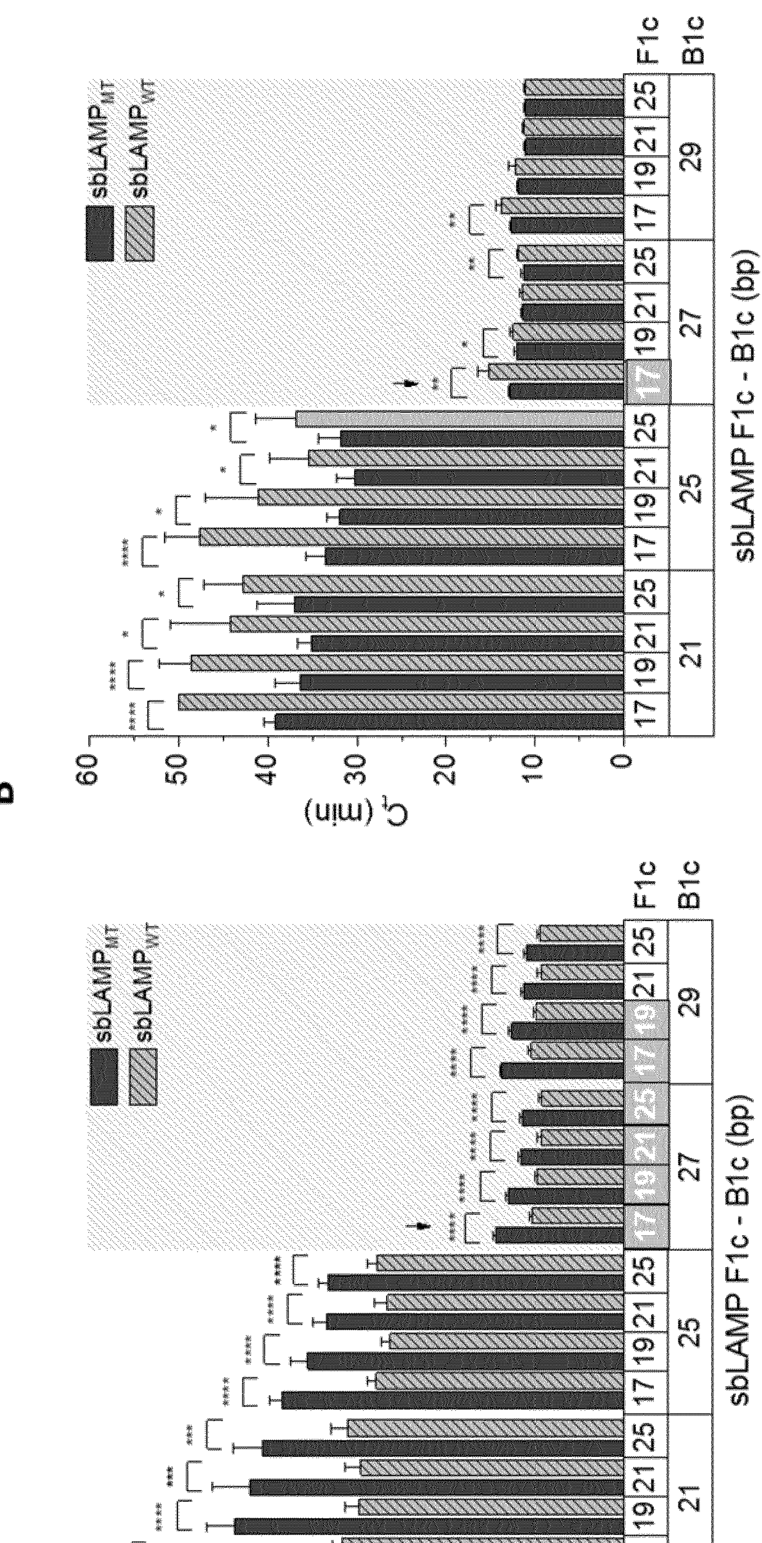
FIG. 2 are graphs of performance results of sbLAMP using different F1c-B1c primer lengths. Graph (A) illustrates a comparison of WT template (580C) amplification by WT specific ($sbLAMP_{WT}$) and MT specific ($sbLAMP_{MT}$) primer sets with different lengths of F1c and B1c. Graph (B) illustrates a comparison of MT template (580Y) amplification by WT specific ($sbLAMP_{WT}$) and MT specific ($sbLAMP_{MT}$) primer sets with different lengths of F1c and B1c). Table 4 shows the $\Delta C_t$ values between specific and unspecific primer sets. Average $C_t$ values of specific reactions below 20 min are light grey shadowed. $\Delta C_t$ values above 2 min are in white lettering. Average of two experiments performed in triplicates using $5\times10^4$ copies/reaction (cp/rxn) of synthetic DNA. Selected sbLAMP primer sets are indicated with arrows in the plots and double underlined cells in Table 4.

The results in FIG. 2 showed the existence of a critical length for B1c (>27 bp) at which the TTP was significantly reduced (highlighted in grey). Two highly significant clusters were obtained by performing k-means cluster analysis and ANOVA test of sbLAMP results of WT and MT templates ($P>F=4.44\times10^{-15}$ and $P>F=1.53\times10^{-14}$, respectively). The selected sbLAMP primer sets according to the highest $\Delta C_t$ were $F1c_{17}$-$B1c_{27}$ for both alleles (indicated by arrows in FIGS. 2A and 2B, and double underlined cells in Table 4).

Guideline 1: Allele-specificity and TTP were significantly enhanced by modifying the length of F1c and B1c with respect to the standard sizes. It is recommended to design allele-specific primers of different lengths depending on the GC % content at the local region. Shortening the primer that sits at the richer GC % region proved to enhance allele-specific amplification (preferably not less than 13 bp). Elongating the primer that sits at the richer AT % region with respect to the other primer equalized their free energy values and $T_m$ (even favoring the primer that sits at the richer AT % region) such that both primers performed properly (early TTP). For optimal performance (allele-specificity and early TTP) more than 15 bp difference between F1c and B1c should be avoided.

Incorporation of USS Primers for Enhancement of sbLAMP.

USS primers were incorporated into the sbLAMP reaction at 2 μM to prevent unspecific sbLAMP amplification. FB and BB of different lengths (FB of 27, 29, 31 and 33 bp, and BB of 17, 19, 21 and 23 bp) were designed and a total of 15 different combinations were tested. Real-time amplification experiments of WT and MT templates were performed independently. Two independent reactions, WT specific reaction ($sbLAMP_{WT}$ and $USS_{MT}$), and MT specific reaction ($sbLAMP_{MT}$ and $USS_{WT}$), were tested with each template.

Figure 3:
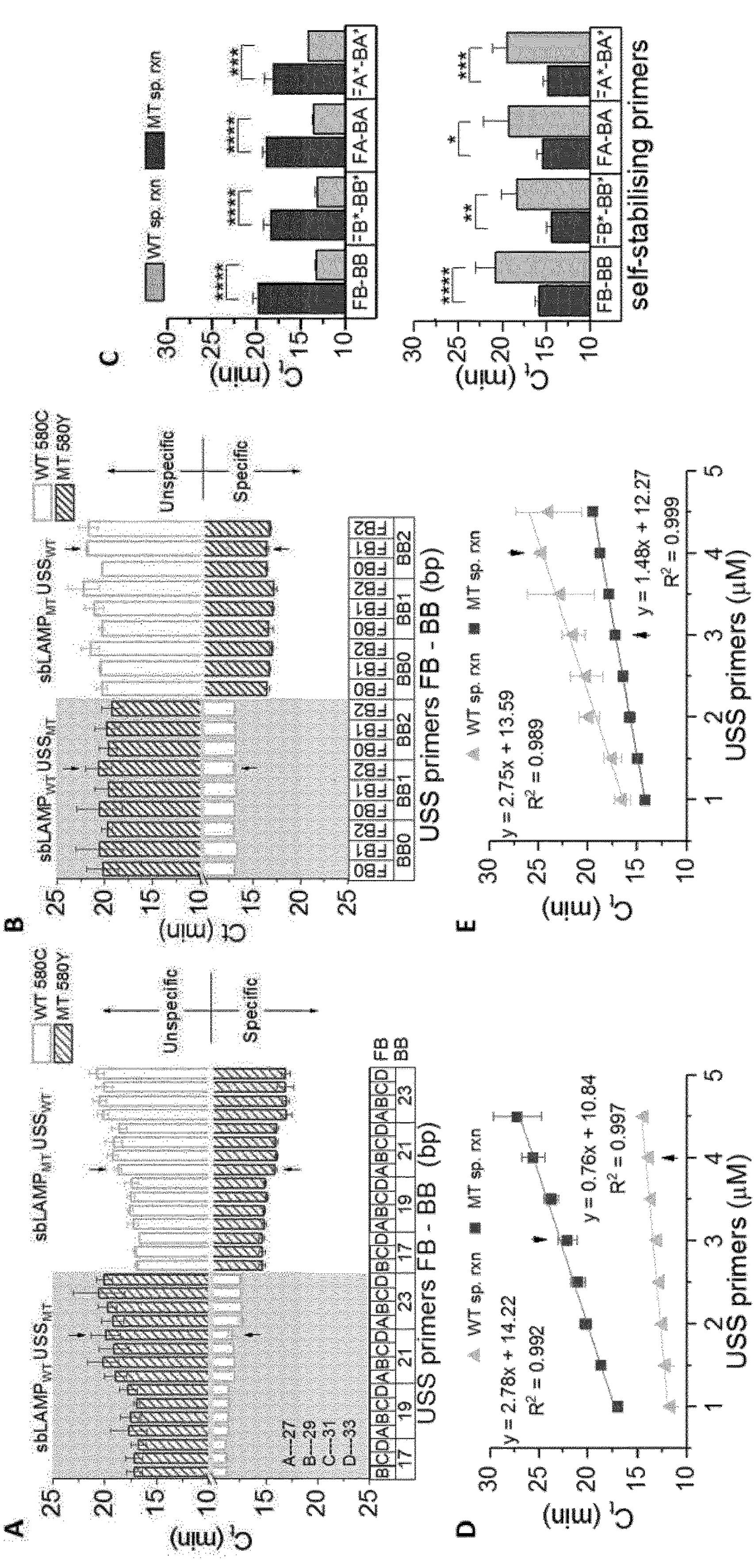
FIG. 3 illustrates an incorporation of USS primer for enhancement of sbLAMP. Graph (A) illustrates a performance comparison of USS primers with different lengths added to sbLAMP reaction at 2 μM/reaction for detecting SNP C580Y. A total of 15 different combinations were tested. Selected USS primers are indicated with arrows (**p-value). Graph (B) illustrates a performance comparison of redesigned USS primers added to sbLAMP reaction at 2 μM/reaction for detecting SNP C580Y. A total of 9 different combinations were tested. Selected USS primers are indicated by arrows (**p-value). Graph (C) illustrates that USS primers enhance allele-specific detection (WT allele in the upper section, and MT allele in the lower section) compared to modified and reverse competitive primers. Graphs (D) and (E) illustrate optimization of the concentration of USS primers (FB/BB). WT template (580C) in D and MT template (580Y) in E. Selected concentrations for the detection of SNP C580Y are labelled by arrows, $USS_{MT}$ at 4 μM and $USS_{WT}$ at 3 μM. Average of two experiments performed in triplicates using $5\times10^4$ copies/reaction of synthetic DNA.

The TTP of specific reactions are shown in the lower section of FIG. 3A and the TTP of unspecific reactions in the upper section. As the length of USS primers is increased unspecific reactions are significantly delayed, while specific reactions are slightly delayed. Consequently, there is a trade-off between allele-specificity and sensitivity. The length of BB had a higher impact on the delay of both reactions than the length of FB. This behavior might be attributed to the richer GC % content of the BB region and hence, the free energy hybridization values. In general, USS primers must be within an optimal length range, and results of both templates, WT and MT, must be interpreted as a whole in order to select the most suitable USS primer set. The criterion for the selection of the most optimal size of FB/BB was based on: (i) minimizing the TTP of the specific reactions, and (ii) maximizing the TTP of the unspecific reactions. Because both criteria cannot be fulfilled by any USS primer set, a balance is considered as the optimal. The selected lengths were $USS_{WT}$ FB27/BB21 and $USS_{MT}$ FB33/BB21. The $\Delta C_t$ between specific and unspecific reactions was statistically significant (****p-value) for both templates, WT and MT.

In order to enhance allele-specificity, the selected FB/BB primers were redesigned to locate the SNP at the $1^{st}$, $2^{nd}$ or $3^{rd}$ positions from their 5' end (FB0, FB1, FB2 and BB0, BB1 and BB2) by adding nucleotides totally complementary to the DNA template. A total of 9 different combinations were tested. According to the estimated free energy values calculated by the inventors, as far as the SNP is displaced away from the 5' end, the specific hybridization is favored. However, the risk of creating an internal bulge between unspecific USS primers and the DNA template prevents to locate the SNP far from the $3^{rd}$ position from the 5' end of FB/BB primers. TTPs of specific reactions were not significantly affected by the incorporation of the redesigned USS primers. However, unspecific reactions were further delayed, contributing to allele-specific detection. Based on the experimental results obtained in FIG. 3B the selected redesigned primers were $USS_{WT}$ $FB1_{27}/BB2_{21}$ and $USS_{MT}$ $FB2_{33}/BB1_{21}$. The $\Delta C_t$ between specific and unspecific reactions was statistically significant (****p-value) for both templates, WT and MT.

Guideline 2: The nucleotide sequence of FB/BB primers is restricted by the template, and their length is limited by the 5' end of LF and LB primers. It is recommended that USS primers are between 0 to 8 nucleotides longer than F1c/B1c primers with GC clamps at their 3' end, if possible, to favor their stability upon hybridization. Locating the SNP within the three base pairs closer to their 5' end (preferably at the $2^{nd}$ or $3^{rd}$ positions, i.e. XB1 XB2 where X=F or B) favor specific hybridization to their target template. It is suggested to avoid placing the SNP more than 4 bp away the 5' end due to the high risk of formation of internal bulges and unspecific amplification.

Comparison of Modified, Unmodified and Reverse Competitive Primers.

Based on the selected $USS_{WT}$ FB127/BB221 and $USS_{MT}$ FB233/BB121 primers, their reverse-complement and the addition of 3' end modifications were studied. Reverse-complement primers to FB/BB, named FA/BA, located the SNP at the 3' end in contrast to FB/BB which located the SNP at the 5' end. The 3' end modified versions of FB/BB and FA/BA, named FA*/BA* and FB*/BB*, included an amino modification which prevented the elongation of the primers by the DNA polymerase. The results presented in FIG. 3C showed the similar behavior of the four primers in combination with sbLAMP. This data proved for the first time that unmodified primers can perform better for allele-specific detection. Between the two sets of unmodified primers, FB/BB outperformed FA/BA based on the higher $\Delta C_t$ between specific and unspecific reactions. Compared to other strategies based on 3' end chemical modifications, and the addition of mismatches at 3' or 5' end of FIP or BIP, the methodology described herein relies on total complementary unmodified primers. The easier design and the lack of chemical modifications reduce the cost of the assay and position this method as a promising molecular-based technique for SNP discrimination to be used at PoC.

Guideline 3: Unmodified primers performed better than 3' end chemically modified primers to prevent unspecific amplification by sbLAMP. It is recommended the use of FB/BB (SNP placed closed to the 5' end) due to the higher $\Delta C_t$ between specific and unspecific reactions.

Study of Different Concentrations of USS Primers.

The selected $USS_{WT}$ $FB1_{27}/BB2_{21}$ and $USS_{MT}$ $FB2_{33}/BB1_{21}$ primers were added to the sbLAMP reaction mix at different concentrations: 1 μM, 1.5 μM, 2 μM, 2.5 μM, 3 μM, 3.5 μM, 4 μM and 4.5 μM. Real-time amplification experiments of WT and MT templates were performed independently. For each template, WT and MT specific reactions were tested (FIGS. 3D and 3E). Specific reactions were slightly delayed as the concentration of the USS primers was increased. The TTP values followed a linear fit with slopes of 0.76 and 1.48 for the WT and the MT template, respectively. Although the unspecific reactions also followed a linear fit, their slopes were sharper, denoting the significance of the concentration of FB/BB on delaying unspecific amplification. The TTP of specific and unspecific reactions were evaluated as a whole in order to discern the optimum concentration of USS primers for allele discrimination. In the case of $USS_{WT}$, 3 μM was chosen as the most suitable concentration while for $USS_{MT}$, 4 μM was selected as the optimum.

Guideline 4: The concentration of USS primers in the reaction mixture should be higher than the concentrations of sbFIP and sbBIP, but not exceeding them by more than 3 μM to not compromise the limit of the detection.

Sensitivity of USS-sbLAMP Method.

Figure 4:
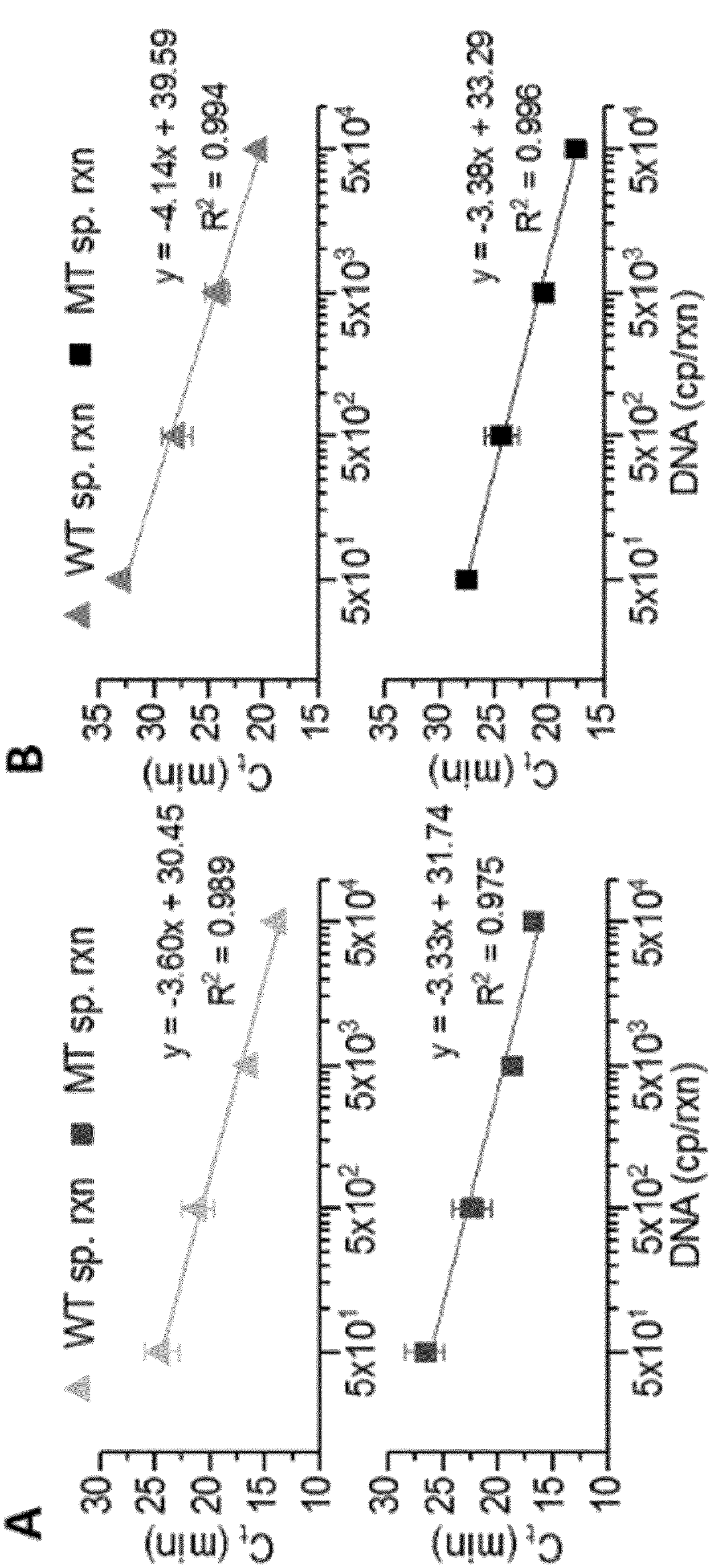
FIG. 4 shows standard curves of specific USS-sbLAMP reactions for detection of SNP C580Y and SNP Y493H. Graph (A) illustrates that USS-sbLAMP amplification of serially diluted WT template (580C) and MT template (580Y), in the upper and lower section respectively. Graph (B) illustrates USS-sbLAMP amplification of serially diluted WT template (+93Y) and MT template (493H), in the upper and lower section respectively. Table 5 shows the $C_t$ values of WT and MT specific reactions with WT or MT template independently. Reactions were considered negative above 30 min for C580Y and above 35 min for Y493H. Average of two experiments performed in triplicates.

Sensitivity was tested using ten-fold serial dilutions ($5\times10^4$, $5\times10^3$, $5\times10^2$ and $5\times10^1$ copies/reaction) of WT and MT templates independently (FIG. 4A, 4B and Table 5). Table 5 shows the $C_t$ values of WT and MT specific reactions with WT or MT template independently. Reactions were considered negative above 30 min for C580Y and above 35 min for Y493H. Average of two experiments performed in triplicates. The detection limit was $5\times10^1$ copies/reaction within 30 min. Standard curves were generated with R2 values of 0.989 and 0.975, for WT and MT template respectively, denoting the ability of the assay to robustly quantify samples. Pure WT and MT templates at concentrations below $5\times10^3$ copies/reaction 5 and $5\times10^4$ copies/reaction, respectively, were uniquely amplified by their corresponding specific reactions providing "yes/no" results.

TABLE 5

$C_t$ values of WT and MT specific reactions with WT or MT template independently

| | | WT template $C_t$ ± SD (min) | | MT template Ct ± SD (min) | |
|---|---|---|---|---|---|
| SNP | DNA (cp/rx) | $USS_{MT}$ $sbLAMP_{WT}$ | $USS_{WT}$ $sbLAMP_{MT}$ | $USS_{MT}$ $sbLAMP_{WT}$ | $USS_{WT}$ $sbLAMP_{MT}$ |
| SNP C580Y | 5 × 10^4 | 13.91 ± 0.19 | 22.84 ± 1.34 | 25.23 ± 1.14 | 16.71 ± 0.69 |
| | 5 × 10^3 | 16.47 ± 0.3 | 26.2 ± 2.12 | NEG | 18.66 ± 0.64 |
| | 5 × 10^2 | 21.02 ± 1.44 | NEG | NEG | 22.32 ± 1.75 |
| | 5 × 10^1 | 24.38 ± 1.57 | NEG | NEG | 26.60 ± 1.75 |
| SNP Y493H | 5 × 10^4 | 20.38 ± 0.4 | 29 ± 1.22 | NEG | 17.59 ± 0.39 |
| | 5 × 10^3 | 24.14 ± 1.15 | NEG | NEG | 20.38 ± 0.37 |
| | 5 × 10^2 | 27.89 ± 1.39 | NEG | NEG | 24.34 ± 1.52 |
| | 5 × 10^1 | 32.94 ± 0.36 | NEG | NEG | 27.55 ± 0.47 |

Sensitivity of sbLAMP was not disrupted by the incorporation of the USS primers, and amplification of the non-target template was successfully inhibited. Amplification was performed in less than 30 min at low DNA copies/reaction indicating the rapidness achieved utilizing the USS-sbLAMP method compared to other techniques based on PCR thermal cycling such as molecular beacons, TaqMan or FRET, which need more than 1h for finishing the assay.

Example 2—Artemisinin-Resistant SNP Y493H

Validation of the USS-sbLAMP method with the artemisinin-resistant SNP Y493H. Following the above created guidelines for the design of USS-sbLAMP primers, different sets of sbLAMP and USS primers were designed and tested to specifically detect a second K13 SNP Y439H (data not shown). $USS_{MT}$-$SbLAMP_{WT}$ primer set consisted of $F1c_{21}$-$B1c_{17}$+$FB2_{24}$/$BB1_{26}$ at 4.5 μM and $USS_{WT}$-$sbLAMP_{MT}$ primer set consisted of $F1c_{21}$-$B1c_{17}$+$FB1_{24}$/$BB0_{26}$ at 4.5 μM were selected for specific detection of WT and MT templates respectively.

Sensitivity was tested using ten-fold serial dilutions ($5\times10^4$, $5\times10^3$, $5\times10^2$ and $5\times10^1$ copies/reaction) of WT and MT templates independently (FIG. 4B and Table 5). For both alleles, the limit of detection was $5\times10^1$ copies/reaction within 35 min. Standard curves were generated with R2 values of 0.994 and 0.996, for WT and MT template respectively. Pure WT and MT templates at concentrations below $5\times10^4$ copies/reaction and $5\times10^5$ copies/reaction, respectively, were uniquely amplified by their corresponding specific reactions providing "yes/no" results.

Example 3—SNP C580Y and SNP Y493H Using Clinical Isolates Cross-Validation of USS-sbLAMP Method for Detection of SNP C580Y and SNP Y493H Using Clinical Isolates The specificity of USS-sbLAMP for detecting SNP C580Y and SNP Y493H was tested using gDNA samples from across human-infective *Plasmodium* species: *P. falciparum, P. ovale* curtisi, *P. ovale* wallikeri, *P. vivax, P. malariae* and *P. knowlesi*, to prove the absence of cross-reactivity with any of them. In addition, two *P. falciparum* samples harboring the mutations 539R and 580Y were tested. There was no cross-reactivity with any of the human-infective *Plasmodium* species (Table 6) and the sample harboring the 539R mutation was uniquely amplified by the WT specific reactions for 580C and 493Y, denoting the high specificity of the method.

TABLE 6. Cross-validation of the USS-sbLAMP method for detection of SNP C580Y and SNP Y493. No cross-reactivity with any human-infective *Plasmodium*. Published Pan-*Plasmodium* primer set[45] was used as positive control for amplification of all human-infective *Plasmodium* species. Samples tested were: Pf1-580C (*P. falciparum* WT SNP 580° C. sample 1), Pf2-580C (*P. falciparum* WT SNP 580Y sample 2), Pf3-580Y (*P. falciparum* MT SNP 580Y), Pf4-539R (*P. falciparum* MT SNP 539T), Poc (*P. ovale* curtisi), Pow (*P. ovale* wallikeri), Pv (*P. vivax*), Pm (*P. malariae*), Pk1 (*P. knowlesi* sample 1), Pk2 (*P. knowlesi* sample 2) and NTC (non-template control). Experiment was performed in triplicates.

| Sample | WT sp. rxn-580C $C_t$ ± SD (min) | MT sp. rxn 580Y $C_t$ ± SD (min) | WT sp. rxn 493Y $C_t$ ± SD (min) | MT sp. rxn 493H $C_t$ ± SD (min) | Pan-Plasmodium• $C_t$ ± SD (min) |
|---|---|---|---|---|---|
| Pf1-580C | 17.79 ± 0.20 | NEG | 26.26 ± 1.38 | NEG | 10.51 ± 0.66 |
| Pf2-580C | 16.74 ± 0.11 | NEG | 25.00 ± 1.56 | NEG | 9.21 ± 0.36 |
| Pf3-580Y | NEG | 18.47 ± 0.61 | 25.93 ± 1.82 | NEG | 8.14 ± 0.08 |
| Pf4-539R | 16.77 ± 0.43 | NEG | 26.13 ± 1.78 | NEG | 8.91 ± 0.20 |
| Poc | NEG | NEG | NEG | NEG | 9.23 ± 0.67 |
| Pow | NEG | NEG | NEG | NEG | 20.25 ± 9.68 |
| Pv | NEG | NEG | NEG | NEG | 9.34 ± 0.35 |
| Pm | NEG | NEG | NEG | NEG | 9.54 ± 0.68 |
| Pk1 | NEG | NEG | NEG | NEG | 5.54 ± 0.07 |
| Pk2 | NEG | NEG | NEG | NEG | 6.34 ± 0.33 |
| NTC | NEG | NEG | NEG | NEG | NEG |

Example 4-USS-sbLAMP Specific to SNP R539T

Primer Design of USS-sbLAMP Specific to R539T

As with Example 1, the USS-sbLAMP method consists of a total of eight primers targeting ten distinct regions of the DNA template. The sbLAMP primer set is composed of two outer primers (F3 and B3), two loop primers (LF and LB) and two inner primers (sbFIP and sbBIP), where F1c and B1c locate the SNP at their 5' end. The USS primer set consists of a forward blocking competitive primer (FB) and a backward blocking competitive primer (BB).

Figure 5:
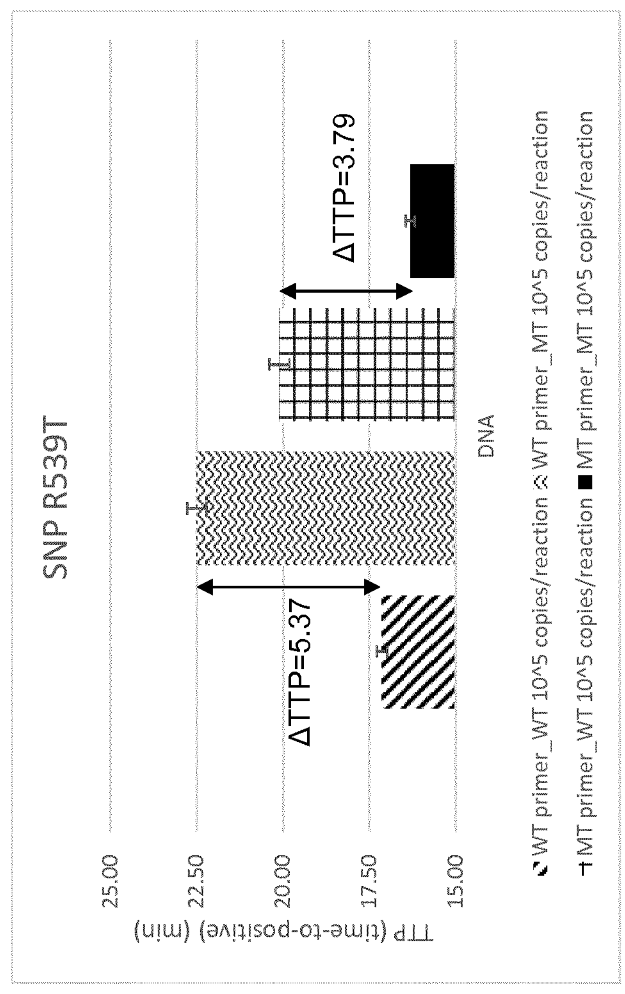
FIG. 5 illustrates a comparison of specific and unspecific primers for the detection of SNP R539T. SD values were represented as error bars

Primers were described as in Example 1. Sequences of final USS-sbLAMP primer sets are provided in Table 7. The results of the comparison are shown in FIG. 5.

TABLE 7

USS-sbLAMP primer sequences for allele-specific amplification of SNP R539T.

| Primer ID | Sequence (5'-3') |
|---|---|
| 539_F3 | AACTGAGGTGTATGATCGTT (SEQ ID NO: 85) |
| 539_B3 | ACCCATGCTTTCATACGA (SEQ ID NO: 86) |
| 539_LF | TTATTTCTTCTAGGTATATTT (SEQ ID NO: 87) |
| 539_LB | ATGATGGCTCTTCTATT (SEQ ID NO: 88) |
| 539_19bpFIP_WT | CTACCATTTGACGTAACACTAAGAGATGTATGGTATGTTTCAAG (SEQ ID NO: 89) |
| 539_20bpBIP_WT | GAATTTATTGTATTGGGGGATCATATGCTTCTACATTCGGTAT (SEQ ID NO: 90) |
| 539_20bpBIP-A_WT | AGAATTTATTGTATTGGGGGATCATATGCTTCTACATTCGGTAT (SEQ ID NO: 91) |
| 539_19bpFIP_MT | GTACCATTTGACGTAACACTAAGAGATGTATGGTATGTTTCAAG (SEQ ID NO: 92) |
| 539_20bpBIP_MT | CAATTTATTGTATTGGGGGATCATATGCTTCTACATTCGGTAT (SEQ ID NO: 93) |
| 539_20bpBIP-A_MT | ACAATTTATTGTATTGGGGGATCATATGCTTCTACATTCGGTAT (SEQ ID NO: 94) |
| 539_23_FB2_WT | TAGAATTTATTGTATTGGGGGATAT (SEQ ID NO: 95) |
| 539_23_FB3_WT | GTAGAATTTATTGTATTGGGGGATAT (SEQ ID NO: 96) |
| 539_23_FB2_MT | TACAATTTATTGTATTGGGGGATAT (SEQ ID NO: 97) |
| 539_23_FB3_MT | GTACAATTTATTGTATTGGGGGATAT (SEQ ID NO: 98) |
| 539_22_BB0_WT | CTACCATTTGACGTAACACCAC (SEQ ID NO: 99) |
| 539_22_BB1_WT | TCTACCATTTGACGTAACACCAC (SEQ ID NO: 100) |
| 539_22_BB1_MT | TGTACCATTTGACGTAACACCAC (SEQ ID NO: 101) |
| 539_17bpFIP_WT | CTACCATTTGACGTAACTAAGAGATGTATGGTATGTTTCAAG (SEQ ID NO: 102) |

Example 5—On-Chip Detection of C580Y Using ISFET-Based Sensing

In order to demonstrate on-chip detection of the C580Y SNP, the following experiment was carried out using an ion-sensitive field-effect transistor (ISFET) system to detect changes in pH caused by the release of a proton ($H^+$) During nucleic acid amplification (due to nucleotide incorporation by the action of a polymerase).

An array of 64×64 ISFET pixels of identical geometry was been fabricated in the AMS 0.35 μm process using silicon nitride ($Si_3N4$) as the passivation layer. Each pixel contains an ISFET configured in a source follower topology as shown in FIG. 6A with the pixel output buffered and sampled using an external 16-b ADC. This way changes in pH are linearly converted into changes in $V_{out}$ for active pixels in the linear input range i.e. excluding extreme cases of trapped charge. Each pixel spans approximately 96 $\mu m^2$ of silicon area with the total array of 4096 sensors spanning 0.56 $mm^2$.

Each LAMP reaction contained the following: 1.5 μL of 10× isothermal buffer (New England Biolabs) 3, 0.9 μL of $MgSO_4$ (100 mM stock), 2.1 μL of dNTPs (10 mM stock), 0.375 μL of BSA (20 mg/mL stock), 2.4 μL of Betaine (5M stock), 0.375 μL of SYTO 9 Green (20 μM stock), 0.6 μL of Bst 2.0 DNA polymerase (8,000U/mL stock), 3 μL of different concentrations of synthetic DNA or gDNA, 1.5 μL of 10× sbLAMP primer mixture (20 μM of sbBIP/sbFIP, 10 μM of LF/LB, 2.5 μM B3/F3 and 3 or 4 μM of FB/BB) and enough nuclease-free water (ThermoFisher Scientific) to bring the volume to 15 μL. Primers were as described in table 3 above.

Reactions were performed at 63° C. for 35-40 min. One melting cycle was performed at 95° C. for 10s, 65° C. for 60s and 97° C. for Is for validation of the specificity of the products. Experiments were carried out twice and each condition was run in triplicates (5 μL each reaction) loading the reactions into LightCycler 480 Multiwell Plates 96 (Roche Diagnostics) utilizing a LightCycler 96 Real-Time PCR System (Roche Diagnostics). In the case of pH-LAMP, the buffering conditions were modified such that pH changes could be measured. Each reaction contained the following: 3.0 μL of 10× isothermal customized buffer (pH 8.5-9), 1.8 μL of $MgSO_4$ (100 mM stock), 4.2 μL of dNTPs (10 mM stock) or 1.68 μL of dNTPs (25 mM stock), 1.8 μL of BSA (20 mg/mL stock), 4.8 μL of Betaine (5M stock), 1.88 μL of Bst 2.0 DNA polymerase (8,000U/mL stock) or 0.13 μL of Bst 2.0 DNA polymerase (120,000U/mL stock), 3 μL of different concentrations of synthetic DNA or gDNA, 0.75 μL of NaOH (0.2M stock), 3 μL of 10×LAMP primer mixture, 0.75 μL of SYTO 9 Green (20 μM stock) only for qPCR experiments, and enough nuclease-free water (ThermoFisher Scientific) to bring the volume to 30 μL. Experiments were conducted twice and each condition was ran in duplicates or triplicates (10 μL each). Reactions tested on chip were carried-out in duplicates (13 μL each). Synthetic DNA sequences used in this work were purchased from Integrated DNA Technologies (The Netherlands) and resuspended in TE buffer to 100 μM stock solutions. USS (Integrated DNA Technologies) were re-suspended in TE buffer to 400 μM

Figure 7:
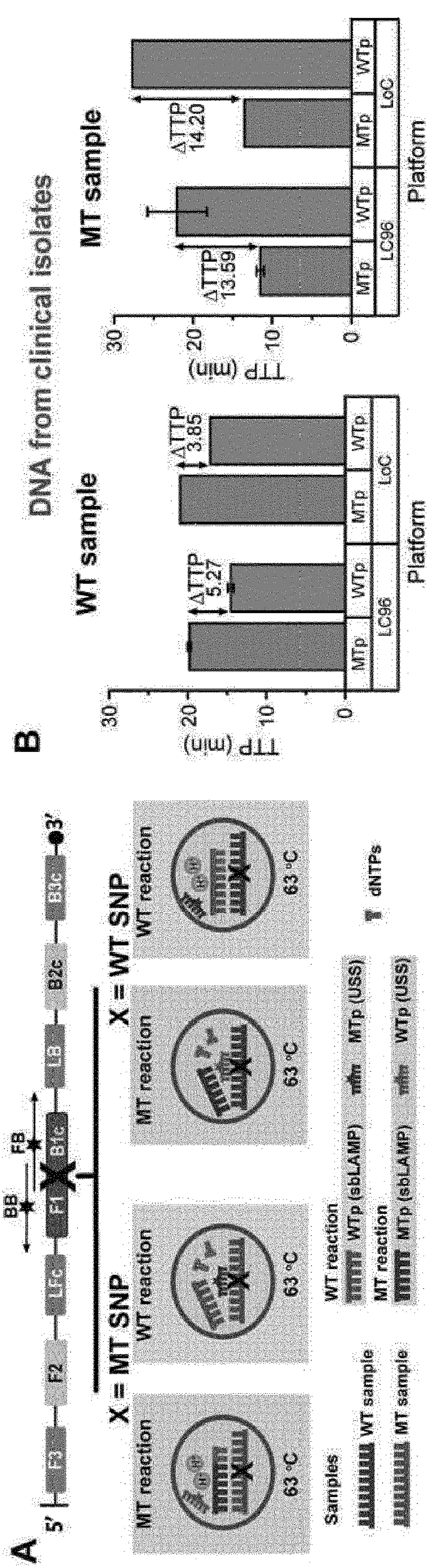
FIG. 7 is an illustration of a Lab-on-Chip detection of C580Y SNP associated to *P. falciparum* artemisinin-resistance. Schematic (A) is a workflow representation of the USS-sbLAMP method for allele-specific detection [44]. Specific reactions amplify in isothermal conditions whereas unspecific reactions are prevented or delayed. Schematic (B) shows a comparison of results obtained with the LoC platform and the LC96 qPCR instrument. TTP values are displayed, with ΔTTP values annotated, indicating that specific reactions always occur earlier.

*P. falciparum* DNA samples from clinical isolates known to be WT or MT were tested with the LoC platform and with a LC96 qPCR instrument as control. Results are presented in FIG. 7B, showing the TTP values obtained with each reaction. Overall, SNP discrimination is possible due to delayed amplification of unspecific targets leading to a difference in TTP values (A TTP). As a result, the capability of the LoC platform to discriminate alleles is illustrated in the same way as the commercial LC96 qPCR instrument.

The invention claimed is:

1. A method for detecting a first allele of a single nucleotide polymorphism (SNP) in a nucleic acid sequence, wherein the method comprises:

(a) amplifying a nucleic acid sequence from a sample using one of the group consisting of: Loop-Mediated Isothermal Amplification (LAMP), Helicase-Dependent Amplification (HDA), Recombinase Polymerase Amplification (RPA), and Nucleic Acid Sequences Based Amplification (NASBA), in a reaction mixture comprising:
   - (i) the nucleic acid sequence,
   - (ii) a nucleic acid polymerase,
   - (iii) a nucleoside triphosphate mixture,
   - (iv) a forward inner primer targeting the first allele (FIPa1), comprising a F1c region which anneals to a F1 region of the nucleic acid sequence in the presence of the first allele and a F2 region which anneals to a F2c region of the nucleic acid sequence,
   - (v) a backward inner primer targeting the first allele (BIPa1), comprising a B1c region which anneals to a B1 region of the nucleic acid sequence in the presence of the first allele and a B2 region which anneals to a B2c region of the nucleic acid sequence,
   - (vi) a forward blocking primer targeting a second allele of the SNP (FBa2), comprising a B1c region which anneals to a B1 region of the nucleic acid sequence in the presence of the second allele, and
   - (vii) a backward blocking primer targeting the second allele (BBa2), comprising a F1c region which anneals to a F1 region of the nucleic acid sequence in the presence of the second allele, wherein the F1 region of the nucleic acid sequence and the B1 region of the nucleic acid sequence both contain the SNP, wherein BBa2 primes extension from its 3' end and/or FBa2 primes extension from its 3' end; and (b) detecting an amplified nucleic acid sequence, wherein the detection of the amplified nucleic acid sequence indicates the presence of the first allele of the SNP.

2. The method of claim 1, wherein the SNP is located proximal to the 5' end of BBa2 and/or FBa2.

3. The method of claim 1, wherein BBa2 is equal to or longer than the F1c region of FIPa1 and/or FBa2 is equal to or longer than the B1c region of BIPa1.

4. The method of claim 1, wherein a concentration of BBa2 in the reaction mixture is higher than a concentration of FIPa1 and/or a concentration of FBa2 in the reaction mixture is higher than a concentration of BIPa1.

5. The method of claim 1, wherein the reaction mixture further comprises a forward outer primer (F3) and/or a backward outer primer (B3).

6. The method of claim 1, wherein the reaction mixture further comprises a forward loop primer (LF) and/or a backward loop primer (LB).

7. A method for detecting drug resistance in an organism, the method comprising detecting the first allele of the SNP in the nucleic acid sequence according to claim 1, the method further comprising diagnosing drug resistance in the organism based on the detection of the amplified acid sequence indicating the presence of the first allele of the SNP.

8. A method for the diagnosis of an infectious disease or a drug resistant infection, the method comprising detecting the first allele of the SNP in the nucleic acid sequence according to claim 1, the method further comprising diagnosing an infectious disease or a drug resistant infection in a subject based on the detection of the amplified sequence indicating the presence of the first allele of the SNP.

9. The method of claim 8, further comprising administering a drug to the subject to treat the infectious disease or the drug resistant infection in the subject.

10. The method of claim 1, wherein the method is performed extemporaneously.

11. The method of claim 1, wherein method steps (a) and (b) are a first reaction and the method further comprises a second reaction, the second reaction comprising:

(c) amplifying a nucleic acid sequence from the sample using one of the group consisting of: Loop-Mediated Isothermal Amplification (LAMP), Helicase-Dependent Amplification (HDA), Recombinase Polymerase Amplification (RPA), and Nucleic Acid Sequences Based Amplification (NASBA), in a reaction mixture comprising
   - (i) the nucleic acid sequence,
   - (ii) a nucleic acid polymerase,
   - (iii) a nucleoside triphosphate mixture,
   - (iv) a forward inner primer targeting the second allele (FIPa2), comprising a F1c region which anneals to a F1 region of the nucleic acid sequence in the presence of the second allele and a F2 region which anneals to a F2c region of the nucleic acid sequence,
   - (v) a backward inner primer targeting the second allele (BIPa2), comprising a B1c region which anneals to a B1 region of the nucleic acid sequence in the presence of the second allele and a B2 region which anneals to a B2c region of the nucleic acid sequence,
   - (vi) a forward blocking primer targeting a first allele of the SNP (FBa1), comprising a B1c region which anneals to a B1 region of the nucleic acid sequence in the presence of the first allele, and
   - (vii) a backward blocking primer targeting the first allele (BBa1), comprising a F1c region which anneals to a F1 region of the nucleic acid sequence in the presence of the first allele, wherein the F1 region of the nucleic acid sequence and the B1 region of the nucleic acid sequence both contain the SNP, and (d) detecting an amplified nucleic acid sequence in the reaction mixture, wherein the detection of an amplified nucleic acid sequence indicates the presence of the second allele of the SNP.

12. The method of claim 11 wherein, in the presence of the second allele, the annealing of the F1c region of FIPa2 and the B1c region of BIPa2 to the nucleic acid sequence is more energetically favorable than the annealing of FBa1 and BBa1 to the nucleic acid sequence.

13. The method of claim 11, wherein:

(a) the SNP is located proximal to the 5' end of BBa1 and/or FBa1;

(b) BBa1 is equal to or longer than the F1c region of FIPa2 and/or FBa1 is equal to or longer than the B1c region of BIPa2; and/or (c) the concentration of BBa1 in the reaction mixture is higher than the concentration of FIPa2 and/or the concentration of FBa1 in the reaction mixture is higher than the concentration of BIPa2.

14. The method of claim 11, wherein:

(a) the first reaction mixture and the second reaction mixture are the same reaction mixture, the detecting amplified nucleic acid sequences in the reaction mixture is by a single fluorescent channel and machine learning distinguishes the amplified nucleic acid sequence that indicates the presence of the first allele of the SNP from the amplified nucleic acid sequence that indicates the presence of the second allele of the SNP; or (b) the first reaction mixture and the second reaction mixture are separate reaction mixtures.

15. The method of claim 1, wherein (a) the nucleic acid sequence is DNA, the nucleic acid polymerase is a DNA polymerase and the nucleoside triphosphate mixture comprises dNTPs, or (b) the nucleic acid sequence containing the SNP is RNA, the method further comprises reverse transcription of the RNA to produce cDNA, the amplifying a nucleic acid sequence is amplifying the cDNA, the nucleic acid polymerase is a DNA polymerase and the nucleoside triphosphate mixture comprises dNTPs.

16. The method of claim 1, wherein the sample is an environmental sample or a clinical sample.

17. The method of claim 1, wherein the nucleic acid is a nucleic acid from a pathogen, a nucleic acid from a host or a synthetic nucleic acid.

18. The method of claim 17, wherein the SNP is selected from the group consisting of C580Y in the *Plasmodium falciparum* kelch 13 gene; F446I in the *Plasmodium falciparum* kelch 13 gene; Y493H in the *Plasmodium falciparum* kelch 13 gene; R539T in the *Plasmodium falciparum* kelch 13 gene; 1543T in the *Plasmodium falciparum* kelch 13 gene; or P553L in the *Plasmodium falciparum* kelch 13 gene.

19. The method of claim 1, wherein the detecting is colorimetric detection, pH-based detection and/or detecting by one or more ion sensors.

20. The method of claim 19, wherein the one or more ion sensors are one or more semiconductor-based ion sensors, optionally complementary metal-oxide-semiconductor (CMOS) based ion sensors.

* * * * *